(12) United States Patent
Longinotti-Buitoni et al.

(10) Patent No.: US 9,817,440 B2
(45) Date of Patent: Nov. 14, 2017

(54) GARMENTS HAVING STRETCHABLE AND CONDUCTIVE INK

(71) Applicant: L.I.F.E. CORPORATION S.A., Luxembourg (LU)

(72) Inventors: Gianluigi Longinotti-Buitoni, Haute-Nendaz (CH); Andrea Aliverti, Como (IT)

(73) Assignee: L.I.F.E. Corporation S.A., Luxembourg (LU)

( * ) Notice: Subject to any disclaimer, the term of this patent is extended or adjusted under 35 U.S.C. 154(b) by 0 days.

(21) Appl. No.: 15/324,152

(22) PCT Filed: Jul. 14, 2015

(86) PCT No.: PCT/IB2015/001802
§ 371 (c)(1),
(2) Date: Jan. 5, 2017

(87) PCT Pub. No.: WO2016/009277
PCT Pub. Date: Jan. 21, 2016

(65) Prior Publication Data
US 2017/0196513 A1 Jul. 13, 2017

Related U.S. Application Data

(63) Continuation-in-part of application No. 14/331,185, filed on Jul. 14, 2014, now Pat. No. 8,945,328, which
(Continued)

(51) Int. Cl.
*G06F 1/16* (2006.01)
*A41D 1/00* (2006.01)
(Continued)

(52) U.S. Cl.
CPC ............ *G06F 1/163* (2013.01); *A41D 1/002* (2013.01); *A41D 13/1281* (2013.01);
(Continued)

(58) Field of Classification Search
CPC ....... G06F 1/163; A41D 1/002; A61B 5/6804; A61B 5/7475; A61B 5/7455
See application file for complete search history.

(56) References Cited

U.S. PATENT DOCUMENTS

| | | | |
|---|---|---|---|
| 3,591,526 | A | 7/1971 | Kawashima |
| 3,793,716 | A | 2/1974 | Smith Johannsen |

(Continued)

FOREIGN PATENT DOCUMENTS

| | | |
|---|---|---|
| EP | 1057923 A1 | 12/2000 |
| EP | 1335831 A1 | 8/2003 |

(Continued)

OTHER PUBLICATIONS

Aliverti et al.; Compartmental analysis of breathing in the supine and prone positions by optoelectronic plethysmography; Ann Biomed Eng; 29(1):60-70; Jan. 2001.

(Continued)

*Primary Examiner* — Jeremy C Norris
(74) *Attorney, Agent, or Firm* — Shay Glenn LLP

(57) ABSTRACT

Methods of forming garments having one or more stretchable conductive ink patterns. Described herein are method of making garments (including compression garments) having one or more highly stretchable conductive ink pattern formed of a composite of an insulative adhesive, a conductive ink, and an intermediate gradient zone between the adhesive and conductive ink. The conductive ink typically includes between about 40-60% conductive particles, between about 30-50% binder; between about 3-7% solvent; and between about 3-7% thickener. The stretchable conductive ink patterns may be stretched more than twice their length without breaking or rupturing.

29 Claims, 31 Drawing Sheets

Related U.S. Application Data is a continuation-in-part of application No. 14/023,830, said application No. PCT/IB2015/001802 is a continuation-in-part of application No. 14/612,060, filed on Feb. 2, 2015, which is a continuation of application No. 14/331,185, filed on Jul. 14, 2014, now Pat. No. 8,945,328.

(60) Provisional application No. 61/699,440, filed on Sep. 11, 2012, provisional application No. 61/862,936, filed on Aug. 6, 2013, provisional application No. 61/950,782, filed on Mar. 10, 2014.

(51) Int. Cl.
*A61B 5/00* (2006.01)
*A41D 13/12* (2006.01)
*D06N 3/00* (2006.01)
*D06N 3/04* (2006.01)
*H05K 1/03* (2006.01)
*H05K 1/09* (2006.01)
*H05K 1/02* (2006.01)

(52) U.S. Cl.
CPC .......... *A61B 5/6804* (2013.01); *A61B 5/7455* (2013.01); *A61B 5/7475* (2013.01); *D06N 3/0063* (2013.01); *D06N 3/042* (2013.01); *H05K 1/0283* (2013.01); *H05K 1/038* (2013.01); *H05K 1/092* (2013.01); *D06N 2209/041* (2013.01); *D06N 2211/10* (2013.01); *D10B 2401/16* (2013.01); *D10B 2501/00* (2013.01); *H05K 2201/10151* (2013.01)

(56) References Cited

U.S. PATENT DOCUMENTS

| | | |
|---|---|---|
| 4,624,817 A | 11/1986 | Gusack et al. |
| 4,710,981 A | 12/1987 | Sanchez |
| 4,823,240 A | 4/1989 | Shenker |
| 4,867,166 A | 9/1989 | Axelgaard et al. |
| 5,036,865 A | 8/1991 | Keaton |
| 5,111,818 A | 5/1992 | Suzuki et al. |
| 5,148,002 A | 9/1992 | Kuo et al. |
| 5,163,006 A | 11/1992 | Deziel |
| 5,241,300 A | 8/1993 | Buschmann |
| 5,280,265 A | 1/1994 | Kramer et al. |
| 5,352,315 A | 10/1994 | Carrier et al. |
| 5,379,461 A | 1/1995 | Wilmers |
| 5,395,508 A | 3/1995 | Jolly et al. |
| 5,557,263 A | 9/1996 | Fisher et al. |
| 5,581,492 A | 12/1996 | Janik |
| 5,635,909 A | 6/1997 | Cole |
| 5,678,448 A | 10/1997 | Fullen et al. |
| 5,694,645 A | 12/1997 | Triplette |
| 5,749,365 A | 5/1998 | Magill |
| 5,802,607 A | 9/1998 | Triplette |
| 5,824,996 A | 10/1998 | Kochman et al. |
| 5,845,644 A | 12/1998 | Hughes et al. |
| 5,853,005 A | 12/1998 | Scanlon |
| 5,865,740 A | 2/1999 | Kelly et al. |
| 5,903,222 A | 5/1999 | Kawarizadeh et al. |
| 5,906,004 A | 5/1999 | Lebby et al. |
| 5,912,653 A | 6/1999 | Fitch |
| 5,921,674 A | 7/1999 | Koczi |
| 6,019,877 A | 2/2000 | Dupelle et al. |
| 6,024,575 A | 2/2000 | Ulrich |
| 6,047,203 A | 4/2000 | Sackner et al. |
| 6,080,690 A | 6/2000 | Lebby et al. |
| 6,097,297 A | 8/2000 | Fard |
| 6,136,127 A | 10/2000 | De Bastiani |
| 6,144,120 A | 11/2000 | Doi et al. |
| 6,210,771 B1 | 4/2001 | Post et al. |
| 6,232,879 B1 | 5/2001 | Tyren |
| 6,259,399 B1 | 7/2001 | Krasner |
| 6,319,015 B1 | 11/2001 | Faunce |
| 6,325,066 B1 | 12/2001 | Hughes et al. |
| 6,341,504 B1 | 1/2002 | Istook |
| 6,349,201 B1 | 2/2002 | Ford |
| 6,415,176 B1 | 7/2002 | Scheirer et al. |
| 6,436,064 B1 | 8/2002 | Kloecker |
| 6,561,814 B2 | 5/2003 | Tilbury et al. |
| 6,563,424 B1 | 5/2003 | Kaario |
| 6,642,467 B2 | 11/2003 | Farringdon |
| 6,668,380 B2 | 12/2003 | Marmaropolous et al. |
| 6,713,733 B2 | 3/2004 | Kochman et al. |
| 6,729,025 B2 | 5/2004 | Farrell et al. |
| 6,792,124 B2 | 9/2004 | Tilbury et al. |
| 6,801,140 B2 | 10/2004 | Mantyjarvi et al. |
| 6,830,344 B2 | 12/2004 | Reho et al. |
| 6,895,261 B1 | 5/2005 | Palamides |
| 6,930,608 B2 | 8/2005 | Grajales et al. |
| 6,970,731 B1 | 11/2005 | Jayaraman et al. |
| 6,982,115 B2 | 1/2006 | Poulos et al. |
| 7,020,508 B2 | 3/2006 | Stivoric et al. |
| 7,034,685 B2 | 4/2006 | Fabre et al. |
| 7,161,084 B2 | 1/2007 | Sandbach |
| 7,173,437 B2 | 2/2007 | Hervieux et al. |
| 7,191,803 B2 | 3/2007 | Orr et al. |
| 7,210,939 B2 | 5/2007 | Marmaropolous et al. |
| 7,211,053 B2 | 5/2007 | Marmaropolous et al. |
| 7,230,610 B2 | 6/2007 | Jung et al. |
| 7,248,756 B2 | 7/2007 | Ebbesen et al. |
| 7,250,547 B1 | 7/2007 | Hofmeister et al. |
| 7,299,034 B2 | 11/2007 | Kates |
| 7,299,964 B2 | 11/2007 | Jayaraman et al. |
| 7,319,895 B2 | 1/2008 | Klefstad-Sillonville et al. |
| 7,320,947 B2 | 1/2008 | Child et al. |
| 7,321,785 B2 | 1/2008 | Harris |
| 7,324,841 B2 | 1/2008 | Reho et al. |
| 7,344,379 B2 | 3/2008 | Marmaropolous et al. |
| 7,348,645 B2 | 3/2008 | Xu |
| 7,365,031 B2 | 4/2008 | Swallow et al. |
| 7,377,133 B2 | 5/2008 | Sandbach et al. |
| 7,388,166 B2 | 6/2008 | Marmaropolous et al. |
| 7,429,959 B2 | 9/2008 | Gerder et al. |
| 7,448,874 B2 | 11/2008 | Willis |
| 7,476,104 B2 | 1/2009 | Marmaropolous et al. |
| 7,559,768 B2 | 7/2009 | Marmaropolous et al. |
| 7,578,195 B2 | 8/2009 | Deangelis et al. |
| 7,616,112 B2 | 11/2009 | Miller, III |
| 7,645,220 B2 | 1/2010 | Hoffman et al. |
| 7,665,288 B2 | 2/2010 | Karayianni et al. |
| 7,683,643 B2 | 3/2010 | Qi et al. |
| 7,712,373 B2 | 5/2010 | Nagle et al. |
| 7,715,873 B1 | 5/2010 | Biere et al. |
| 7,719,007 B2 | 5/2010 | Thompkins et al. |
| 7,732,002 B2 | 6/2010 | Kodas et al. |
| 7,753,685 B2 | 7/2010 | Lee et al. |
| 7,753,845 B2 | 7/2010 | Gopinathan et al. |
| 7,760,082 B2 | 7/2010 | Wong et al. |
| 7,769,412 B1 | 8/2010 | Gailloux |
| 7,770,473 B2 | 8/2010 | Von Lilienfeld-Toal et al. |
| 7,779,656 B2 | 8/2010 | Dias et al. |
| 7,783,334 B2 | 8/2010 | Nam et al. |
| 7,787,726 B2 | 8/2010 | Ten Eyck et al. |
| 7,849,888 B2 | 12/2010 | Karayianni et al. |
| 7,862,624 B2 | 1/2011 | Tran |
| 7,870,761 B2 | 1/2011 | Valentine et al. |
| 7,872,557 B2 | 1/2011 | Seibert |
| 7,878,030 B2 | 2/2011 | Burr |
| 7,880,607 B2 | 2/2011 | Olson et al. |
| 7,891,020 B2 | 2/2011 | Von Bluecher |
| 7,914,108 B2 | 3/2011 | Konno et al. |
| 7,933,554 B2 | 4/2011 | Hoyt et al. |
| 7,955,696 B2 | 6/2011 | Baikerikar et al. |
| 7,976,480 B2 | 7/2011 | Grajales et al. |
| 7,982,613 B2 | 7/2011 | Zheng |
| 7,983,876 B2 | 7/2011 | Vock et al. |
| 8,008,606 B2 | 8/2011 | Kaiserman et al. |
| 8,024,023 B2 | 9/2011 | Tolvanen |
| 8,032,199 B2 | 10/2011 | Linti et al. |
| 8,063,307 B2 | 11/2011 | Bukshpun et al. |

(56) References Cited

U.S. PATENT DOCUMENTS

| | | |
|---|---|---|
| 8,099,258 B2 | 1/2012 | Alten et al. |
| 8,140,143 B2 | 3/2012 | Picard et al. |
| 8,146,171 B2 | 4/2012 | Chung et al. |
| 8,162,857 B2 | 4/2012 | Lanfermann et al. |
| 8,186,231 B2 | 5/2012 | Graumann et al. |
| 8,214,008 B2 | 7/2012 | Hassonjee et al. |
| 8,228,202 B2 | 7/2012 | Buchner et al. |
| 8,253,586 B1 | 8/2012 | Matak |
| 8,262,217 B2 | 9/2012 | Furukawa |
| 8,263,215 B2 | 9/2012 | Burr et al. |
| 8,267,862 B2 | 9/2012 | Jeong et al. |
| 8,308,489 B2 | 11/2012 | Lee et al. |
| 8,331,097 B2 | 12/2012 | Yang et al. |
| 8,340,740 B2 | 12/2012 | Holzer et al. |
| 8,348,841 B2 | 1/2013 | Varadan |
| 8,348,865 B2 | 1/2013 | Jeong et al. |
| 8,362,882 B2 | 1/2013 | Heubei et al. |
| 8,373,079 B2 | 2/2013 | Walkington |
| 8,398,546 B2 | 3/2013 | Pacione et al. |
| 8,403,845 B2 | 3/2013 | Stivoric et al. |
| 8,416,579 B2 | 4/2013 | Biesheuvel et al. |
| 8,475,371 B2 | 7/2013 | Derchak et al. |
| 8,739,397 B2 | 6/2014 | Nagata et al. |
| 8,862,431 B2 | 10/2014 | Hodge |
| 8,925,393 B2 | 1/2015 | Cannard et al. |
| 8,945,328 B2 | 2/2015 | Longinotti-Buitoni et al. |
| 8,948,839 B1 | 2/2015 | Longinotti-Buitoni et al. |
| 8,954,129 B1 | 2/2015 | Schlegel et al. |
| 9,282,893 B2 | 3/2016 | Longinotti-Buitoni et al. |
| 2002/0093515 A1 | 7/2002 | Fay et al. |
| 2003/0139692 A1 | 7/2003 | Barrey |
| 2004/0115430 A1 | 6/2004 | Leonard |
| 2004/0249242 A1 | 12/2004 | Lau et al. |
| 2005/0029680 A1 | 2/2005 | Jung et al. |
| 2005/0058744 A1 | 3/2005 | Steinberg et al. |
| 2005/0067816 A1 | 3/2005 | Buckman |
| 2005/0228234 A1 | 10/2005 | Yang |
| 2006/0007059 A1 | 1/2006 | Bell |
| 2006/0080182 A1 | 4/2006 | Thompson et al. |
| 2006/0124470 A1 | 6/2006 | Zama et al. |
| 2006/0139165 A1 | 6/2006 | Bader |
| 2006/0155182 A1 | 7/2006 | Mazzarolo |
| 2007/0000912 A1 | 1/2007 | Alsenbrey |
| 2007/0046720 A1 | 3/2007 | Konno et al. |
| 2007/0049842 A1 | 3/2007 | Hill et al. |
| 2007/0151312 A1 | 7/2007 | Bruce et al. |
| 2007/0153363 A1 | 7/2007 | Gruner |
| 2007/0178716 A1 | 8/2007 | Glaser et al. |
| 2007/0202765 A1 | 8/2007 | Krans et al. |
| 2007/0293781 A1 | 12/2007 | Sims et al. |
| 2008/0045815 A1 | 2/2008 | Derchak et al. |
| 2008/0058744 A1 | 3/2008 | Tippey et al. |
| 2008/0064964 A1 | 3/2008 | Nagata et al. |
| 2008/0083720 A1 | 4/2008 | Gentile et al. |
| 2008/0083721 A1 | 4/2008 | Kaiserman et al. |
| 2008/0083740 A1 | 4/2008 | Kaiserman et al. |
| 2008/0171914 A1 | 7/2008 | Ouwerkerk et al. |
| 2008/0177168 A1 | 7/2008 | Callahan et al. |
| 2008/0234561 A1 | 9/2008 | Roesicke et al. |
| 2008/0241391 A1 | 10/2008 | Kim et al. |
| 2008/0246629 A1 | 10/2008 | Tsui et al. |
| 2008/0255794 A1 | 10/2008 | Levine |
| 2008/0258921 A1 | 10/2008 | Woo et al. |
| 2008/0269629 A1 | 10/2008 | Reiner |
| 2008/0269652 A1 | 10/2008 | Reiner |
| 2008/0287769 A1 | 11/2008 | Kurzweil et al. |
| 2008/0287770 A1 | 11/2008 | Kurzweil et al. |
| 2008/0294019 A1 | 11/2008 | Tran |
| 2009/0012408 A1 | 1/2009 | Nagata et al. |
| 2009/0018410 A1 | 1/2009 | Coene et al. |
| 2009/0105795 A1 | 4/2009 | Minogue et al. |
| 2009/0112078 A1 | 4/2009 | Tabe |
| 2009/0157327 A1 | 6/2009 | Nissila |
| 2009/0227856 A1 | 9/2009 | Russell et al. |
| 2009/0281394 A1 | 11/2009 | Russell et al. |
| 2009/0286055 A1 | 11/2009 | Pourdeyhimi et al. |
| 2010/0004720 A1 | 1/2010 | Li et al. |
| 2010/0029598 A1 | 2/2010 | Kopitz et al. |
| 2010/0041974 A1 | 2/2010 | Ting et al. |
| 2010/0071205 A1 | 3/2010 | Graumann et al. |
| 2010/0077528 A1 | 4/2010 | Lind et al. |
| 2010/0112195 A1 | 5/2010 | Kodas et al. |
| 2010/0113910 A1 | 5/2010 | Brauers et al. |
| 2010/0149567 A1 | 6/2010 | Kanazawa et al. |
| 2010/0185062 A1 | 7/2010 | Salazar et al. |
| 2010/0185398 A1 | 7/2010 | Berns et al. |
| 2010/0194815 A1 | 8/2010 | Furukawa |
| 2010/0198038 A1 | 8/2010 | Nagata et al. |
| 2010/0234715 A1 | 9/2010 | Shin et al. |
| 2010/0274100 A1 | 10/2010 | Behar et al. |
| 2010/0292598 A1 | 11/2010 | Roschk et al. |
| 2010/0309209 A1 | 12/2010 | Hodgins et al. |
| 2010/0312071 A1 | 12/2010 | Schenk |
| 2010/0324405 A1 | 12/2010 | Niemi et al. |
| 2011/0000412 A1 | 1/2011 | Chung et al. |
| 2011/0015498 A1 | 1/2011 | Mestrovic et al. |
| 2011/0032103 A1 | 2/2011 | Bhat et al. |
| 2011/0042125 A1 | 2/2011 | Lee et al. |
| 2011/0087115 A1 | 4/2011 | Sackner et al. |
| 2011/0092795 A1 | 4/2011 | Derchak |
| 2011/0100683 A1 | 5/2011 | Bhattacharya et al. |
| 2011/0102304 A1 | 5/2011 | Nelson |
| 2011/0115624 A1 | 5/2011 | Tran |
| 2011/0125064 A1 | 5/2011 | Shyr |
| 2011/0130643 A1 | 6/2011 | Derchak et al. |
| 2011/0144457 A1 | 6/2011 | Coulon |
| 2011/0183068 A1 | 7/2011 | Yamakawa et al. |
| 2011/0184270 A1 | 7/2011 | Russell et al. |
| 2011/0259638 A1 | 10/2011 | Sherrill et al. |
| 2011/0267578 A1 | 11/2011 | Wilson |
| 2011/0277206 A1 | 11/2011 | Sokolowski |
| 2011/0288605 A1 | 11/2011 | Kaib et al. |
| 2012/0024833 A1 | 2/2012 | Klewer et al. |
| 2012/0029299 A1 | 2/2012 | Deremer et al. |
| 2012/0030935 A1 | 2/2012 | Slade et al. |
| 2012/0031431 A1 | 2/2012 | Carlson et al. |
| 2012/0035426 A1 | 2/2012 | Mielcarz et al. |
| 2012/0071039 A1 | 3/2012 | Debock et al. |
| 2012/0071793 A1 | 3/2012 | Gal |
| 2012/0078127 A1 | 3/2012 | McDonald et al. |
| 2012/0088986 A1 | 4/2012 | David et al. |
| 2012/0118427 A1 | 5/2012 | Brookstein et al. |
| 2012/0127687 A1 | 5/2012 | Allee et al. |
| 2012/0136231 A1 | 5/2012 | Markel |
| 2012/0143093 A1 | 6/2012 | Stirling et al. |
| 2012/0144551 A1 | 6/2012 | Guldalian |
| 2012/0144561 A1 | 6/2012 | Begriche et al. |
| 2012/0144934 A1 | 6/2012 | Russell et al. |
| 2012/0146797 A1 | 6/2012 | Oskin et al. |
| 2012/0158074 A1 | 6/2012 | Hall |
| 2012/0165645 A1 | 6/2012 | Russell et al. |
| 2012/0165717 A1 | 6/2012 | Al Khaburi |
| 2012/0184826 A1 | 7/2012 | Keenan et al. |
| 2012/0188158 A1 | 7/2012 | Tan et al. |
| 2012/0197224 A1 | 8/2012 | Chagger |
| 2012/0215076 A1 | 8/2012 | Yang et al. |
| 2012/0223833 A1 | 9/2012 | Thomas et al. |
| 2012/0233751 A1 | 9/2012 | Hexels |
| 2012/0238845 A1 | 9/2012 | Yang |
| 2012/0246795 A1 | 10/2012 | Scheffler et al. |
| 2012/0255166 A1 | 10/2012 | Kim et al. |
| 2012/0324616 A1 | 12/2012 | Hyde et al. |
| 2012/0330109 A1 | 12/2012 | Tran |
| 2013/0013331 A1 | 1/2013 | Horseman |
| 2013/0019372 A1 | 1/2013 | Esses |
| 2013/0019383 A1 | 1/2013 | Korkala et al. |
| 2013/0041272 A1 | 2/2013 | Guillen et al. |
| 2013/0053674 A1 | 2/2013 | Volker |
| 2013/0066168 A1 | 3/2013 | Yang et al. |
| 2013/0072777 A1 | 3/2013 | Tremblay |
| 2013/0077263 A1 | 3/2013 | Oleson et al. |
| 2013/0079860 A1 | 3/2013 | Besio |
| 2013/0179288 A1 | 7/2013 | Moses et al. |
| 2013/0212900 A1 | 8/2013 | Stewart |

(56) References Cited

U.S. PATENT DOCUMENTS

| | | |
|---|---|---|
| 2013/0244121 A1 | 9/2013 | Gogotsi et al. |
| 2013/0245423 A1 | 9/2013 | Derchak et al. |
| 2013/0281795 A1 | 10/2013 | Varadan |
| 2013/0314668 A1 | 11/2013 | Haddadi et al. |
| 2014/0061273 A1 | 3/2014 | Bullivant et al. |
| 2014/0100436 A1 | 4/2014 | Brunner et al. |
| 2014/0135593 A1 | 5/2014 | Jayalth et al. |
| 2014/0182880 A1 | 7/2014 | Simenhaus et al. |
| 2014/0206948 A1 | 7/2014 | Romem |
| 2014/0303470 A1 | 10/2014 | Tsukada et al. |
| 2014/0312027 A1 | 10/2014 | Augustine et al. |
| 2015/0143601 A1 | 5/2015 | Longinotti-Buitoni et al. |
| 2015/0250420 A1 | 9/2015 | Longinotti-Buitoni et al. |
| 2016/0314576 A1 | 10/2016 | Aliverti et al. |

FOREIGN PATENT DOCUMENTS

| | | |
|---|---|---|
| EP | 1478249 A1 | 11/2004 |
| EP | 1509128 A1 | 3/2005 |
| EP | 1622512 A2 | 2/2006 |
| EP | 1709903 A1 | 10/2006 |
| EP | 1905112 A2 | 4/2008 |
| EP | 1907075 A2 | 4/2008 |
| EP | 1925718 A2 | 5/2008 |
| EP | 2025369 A2 | 2/2009 |
| EP | 2191737 A1 | 6/2010 |
| EP | 2196142 A1 | 6/2010 |
| EP | 2217145 A1 | 8/2010 |
| EP | 2314744 A2 | 4/2011 |
| WO | WO90/06189 A1 | 6/1990 |
| WO | WO00/16493 A1 | 3/2000 |
| WO | WO01/01855 A1 | 1/2001 |
| WO | WO03/060449 A1 | 7/2003 |
| WO | WO2004/076731 A1 | 9/2004 |
| WO | WO2004/107831 A2 | 12/2004 |
| WO | WO2005/032447 A2 | 4/2005 |
| WO | WO2005/067796 A1 | 7/2005 |
| WO | WO2005/096133 A1 | 10/2005 |
| WO | WO2006/064447 A2 | 6/2006 |
| WO | WO2006/102538 A2 | 9/2006 |
| WO | WO2007/056557 A1 | 5/2007 |
| WO | WO2008/137046 A1 | 11/2008 |
| WO | WO2008/153786 A1 | 12/2008 |
| WO | WO2009/040696 A1 | 4/2009 |
| WO | WO2009/112281 A1 | 9/2009 |
| WO | WO2010/038176 A1 | 4/2010 |
| WO | WO2010/044018 A1 | 4/2010 |
| WO | WO2010/058346 A2 | 5/2010 |
| WO | WO2010/085671 A1 | 7/2010 |
| WO | WO2010/085688 A1 | 7/2010 |
| WO | WO2010/120945 A1 | 10/2010 |
| WO | WO2011/092620 A1 | 8/2011 |
| WO | WO2011/156095 A2 | 12/2011 |
| WO | WO2012/011068 A1 | 1/2012 |
| WO | WO2012/060524 A1 | 5/2012 |
| WO | WO2012/066056 A1 | 5/2012 |
| WO | WO2012/073076 A1 | 6/2012 |
| WO | WO2012/073230 A1 | 6/2012 |
| WO | WO2012/083066 A2 | 6/2012 |
| WO | WO2012/104484 A1 | 8/2012 |
| WO | WO2012/110954 A1 | 8/2012 |
| WO | WO2012/112186 A1 | 8/2012 |
| WO | WO2012/113014 A1 | 8/2012 |
| WO | WO2012/140079 A1 | 10/2012 |
| WO | WO2012/140522 A2 | 10/2012 |
| WO | WO2012/168836 A2 | 12/2012 |
| WO | WO2012/176193 A1 | 12/2012 |
| WO | WO2014/025430 A2 | 2/2014 |
| WO | WO2014/075682 A1 | 5/2014 |
| WO | WO2014/204323 A1 | 12/2014 |
| WO | WO2015/103620 A1 | 7/2015 |
| WO | WO2015/138515 A1 | 9/2015 |
| WO | WO2016/035350 A1 | 3/2016 |

OTHER PUBLICATIONS

Babchenko et al.; Fiber optic sensor for the measurement of respiratory chest circumference changes; J Biomed Opt; 4(2):224-229; Apr. 1999.

Cala et al.; Chest wall and lung vol. estimation by optical reflectance motion analysis; J Appl Physiol; 81(6):2680-2689; Dec. 1996.

Chadha et al.; Validation of respiratory inductive plethysmography using different calibration procedures; Am Rev Respir Dis; 125:644-649; Jun. 1982.

Chen et al.; Color structured light system of chest wall motion measurement for respiratory volume evaluation; J Biomed Opt; 15(2):026013; Mar.-Apr. 2010.

D'Angelo et al.; A system for respiratory motion detection using optical fibers embedded into textiles; Conf Proc IEEE Med Biol Soc; 3694-3697; Aug. 2008.

Dodgson; Variation and extrema of human interpupillary distance; Prod. of SPIE: Stereoscopic Displays and Virtual Reality Systems XI; vol. 5291; pp. 36-46; Jan. 2004.

Ferrigno et al.; Three-dimensional optical analysis of chest wall motion; J Appl Physiol; 77(3):1224-1231; Sep. 1994.

Gramse et al.; Novel concept for a noninvasive cardiopulmonary monitor for infants: a pair of pajamas with an integrated sensor module; Ann Biomed Eng; 31(2):152-158; Feb. 2003.

Heilman et al.; Accuracy of the LifeShirt (Vivometrics) in the detection of cardiac rhythms; Biol Psychol; 75(3):300-305; Jul. 2007.

Kenyon et al.; Rib cage mechanics during quiet breathing and exercise in humans; J Appl Physiol; 83(4):1242-1255; Oct. 1997.

Konno et al.; Measurement of the separate volume changes of rib cage and abdomen during breathing; J Appl Physiol; 22(3):407-422; Mar. 1967.

Lafortuna et al.; A new instrument for the measurement of rib cage and abdomen circumference variation in respiration at rest and during exercise; Eur J Appl Physiol Occup Physiol; 71(2-3):259-265; Mar. 1995.

Milledge et al.; Inductive plethysmography—a new respiratory transducer; J Physiol; 267(1):4P-5P; May 1977.

Peacock et al.; Optical mapping of the thoracoabdominal wall; Thorax; 39 (2):93-100; Feb. 1984.

Peacock et al.; Optical measurement of the change in trunk volume with breathing; Bull Eur Physiopathol Respir; 21(2):125-129; Mar.-Apr. 1985.

Pennock B.E.; Rib cage and abdominal piezoelectric film belts to measure ventilatory airflow; J Clin Monit; 6(4):276-283; Oct. 1990.

Sackner et al.; Calibration of respiratory inductive plethysmograph during natural breathing; J Appl Physiol; 66(1):410-420; Jan. 1989.

Saumarez; Automated optical measurements of human torso surface movements during freathing; J. Appl. Physiol.; 60(2); pp. 702-709; Feb. 1986.

Zimmerman et al.; Postural changes in rib cage and abdominal volume-motion coefficients and their effect on the calibration of a respiratory inductance plethysmograph; Am Rev Respir Dis; 127(2):209-214; Feb. 1983.

Mauri et al.; U.S. Appl. No. 15/335,403 entitled "Calibration packaging apparatuses for physiological monitoring garments," filed Oct. 26, 2016.

Longinotti-Buitoni et al.; U.S. Appl. No. 15/516,138 entitled "Devices and methods for use with physiological monitoring garments," filed Mar. 31, 2017.

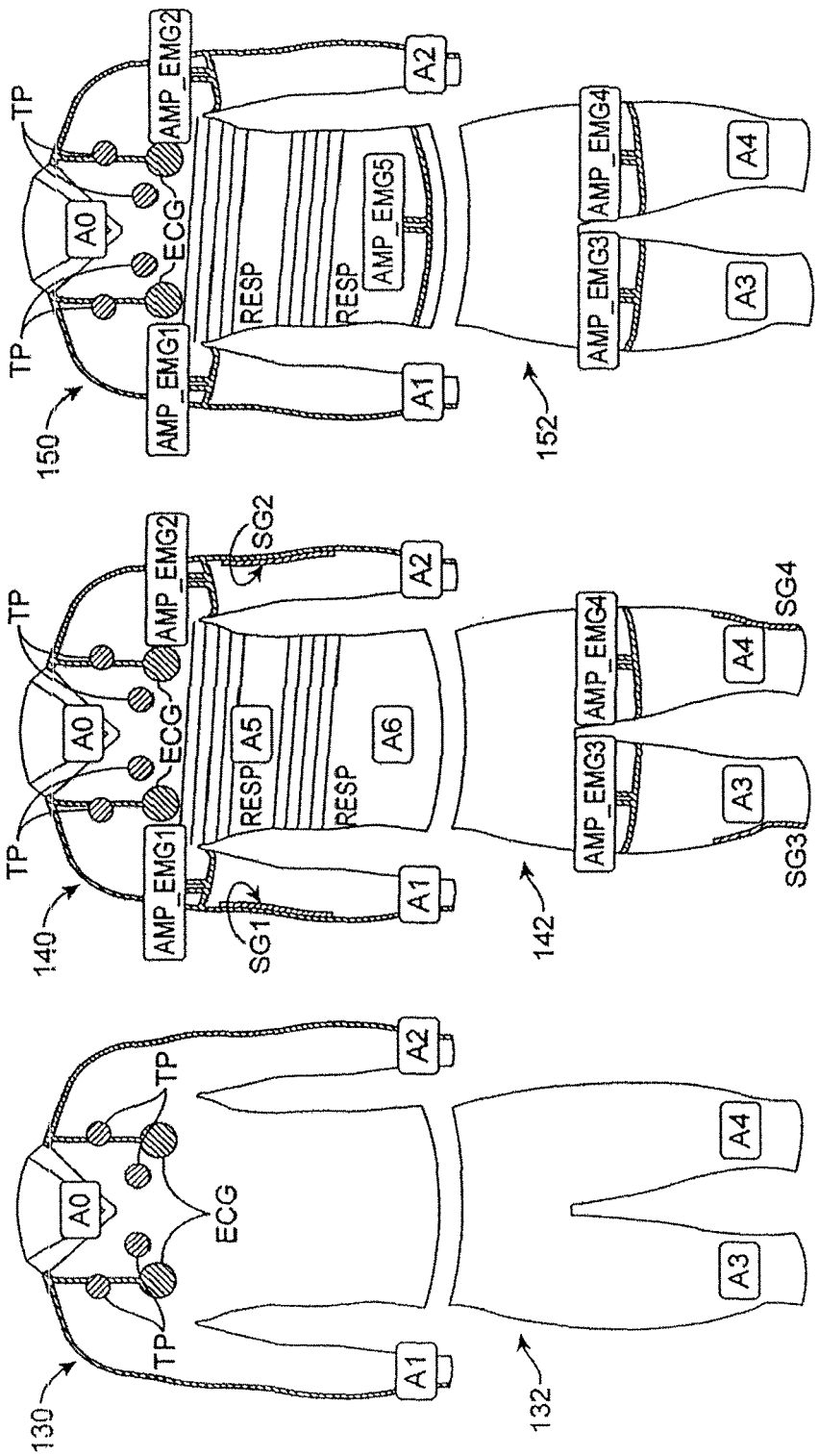

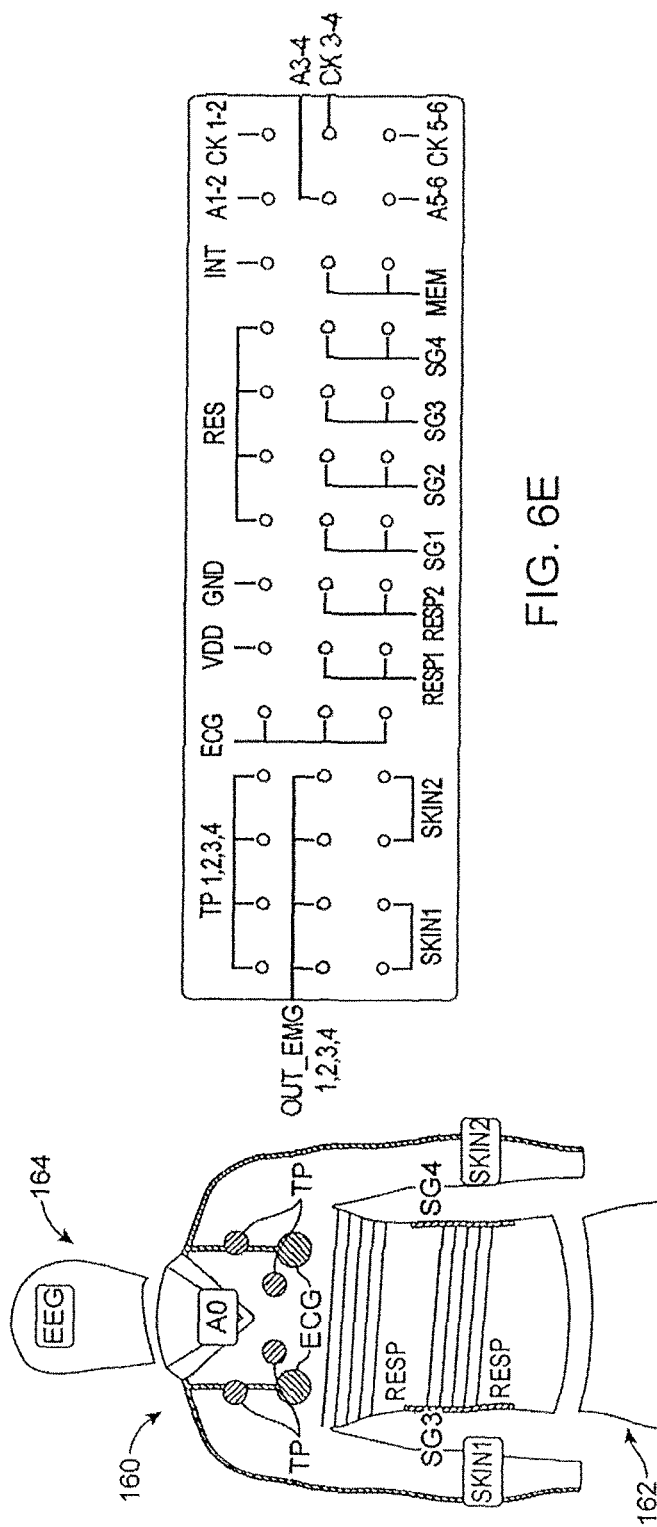

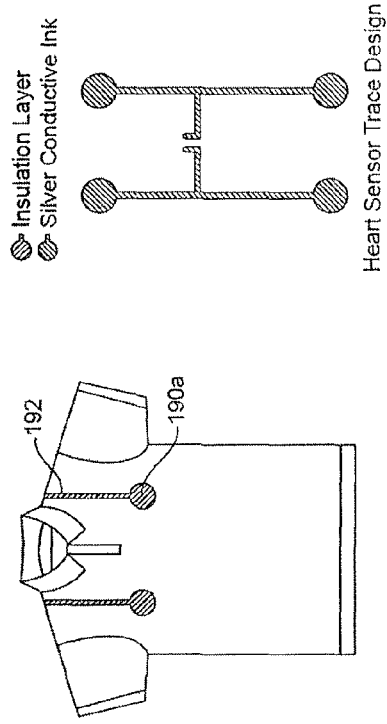
FIG. 8A
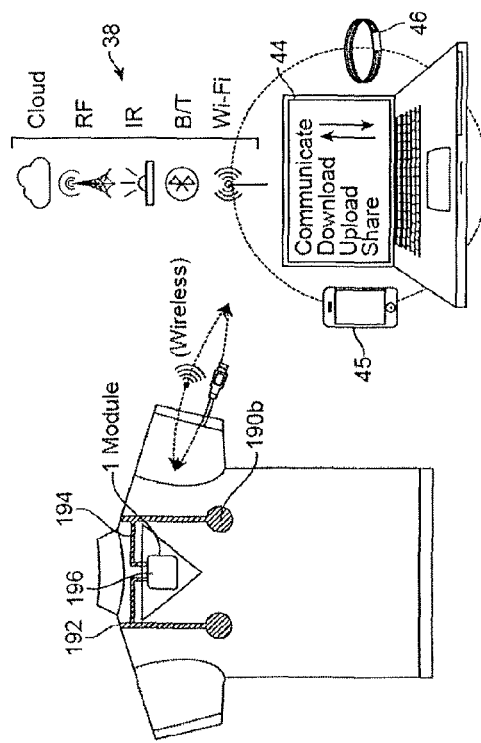
FIG. 8C
FIG. 8B
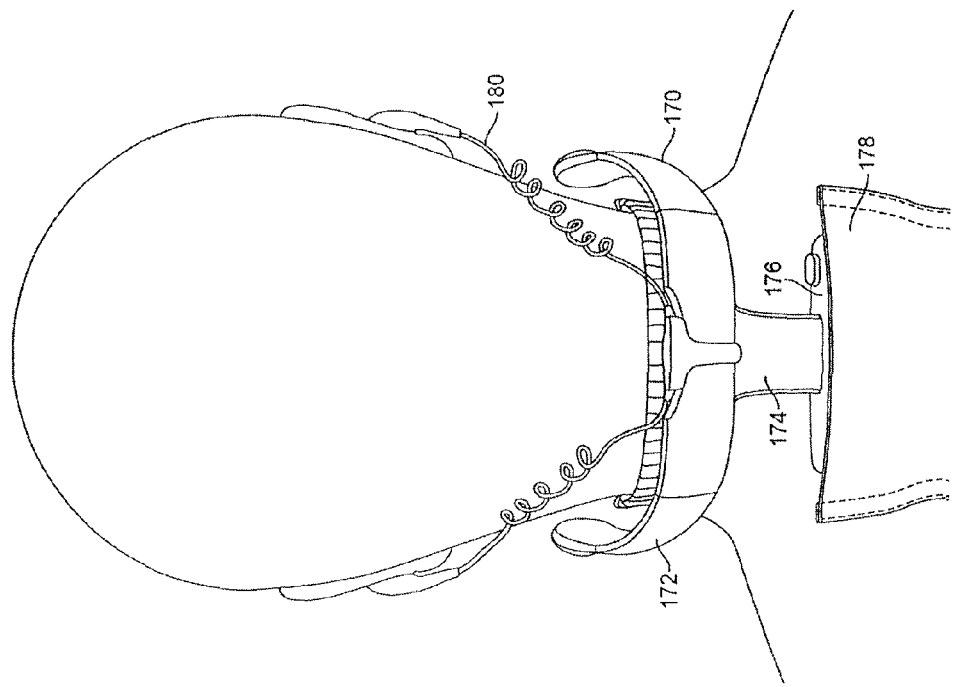
FIG. 7

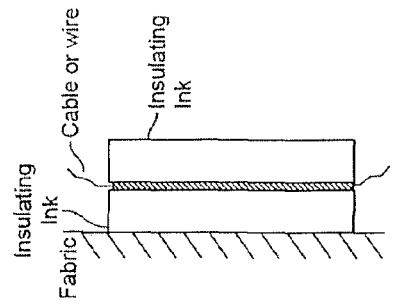
FIG. 10A
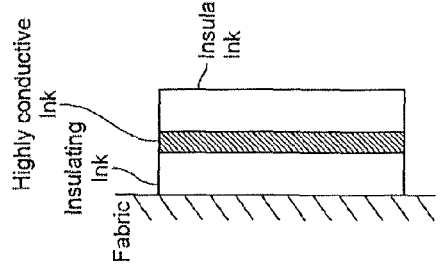
FIG. 10B
FIG. 10C
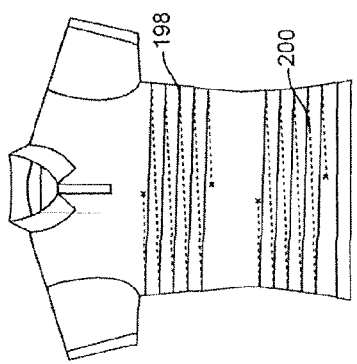
FIG. 9A
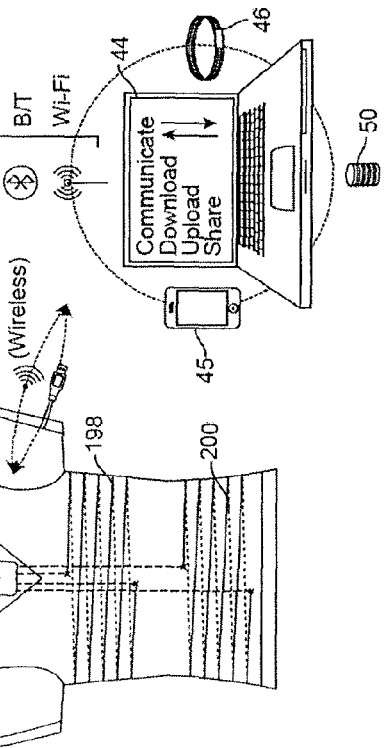
FIG. 9B

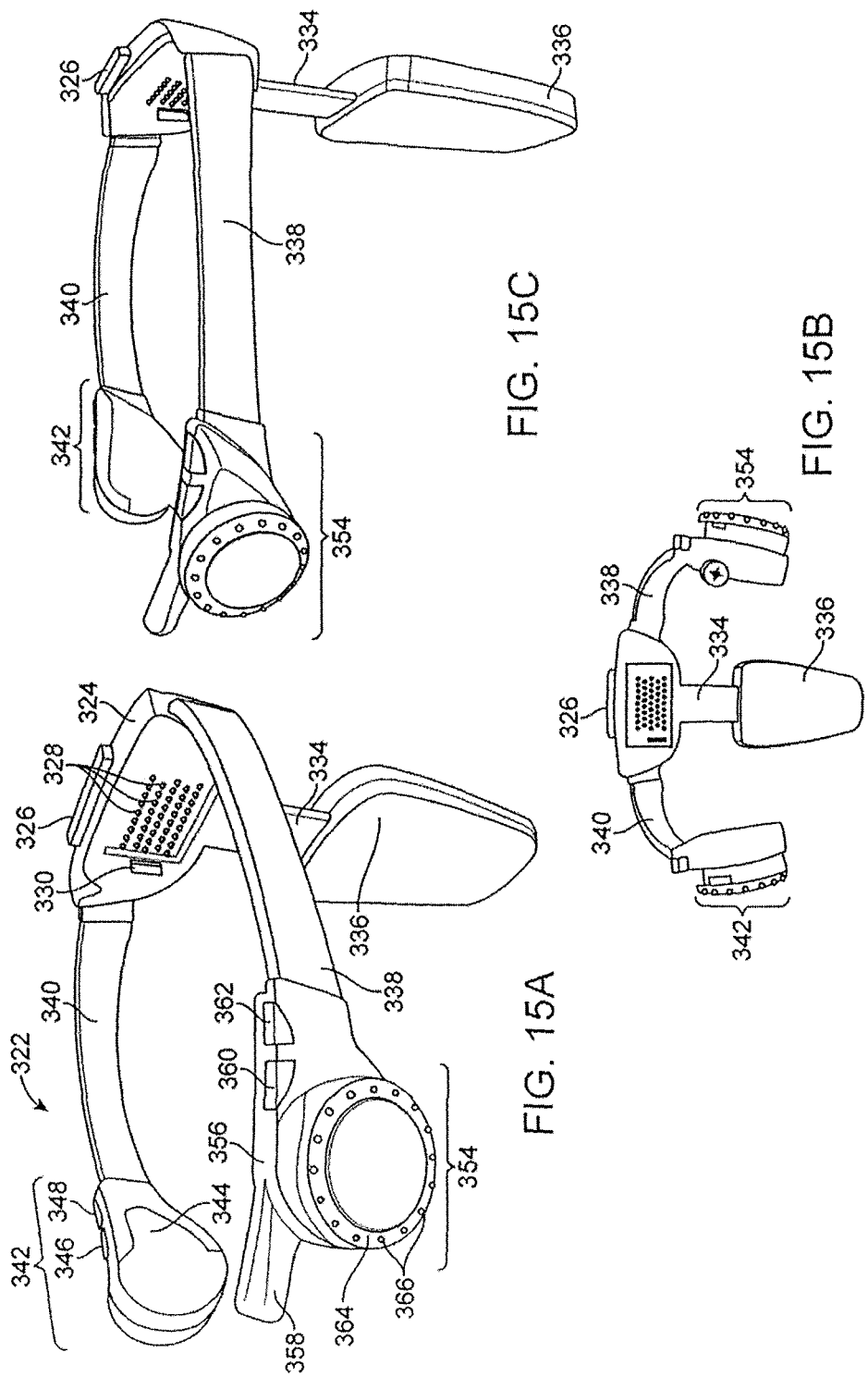

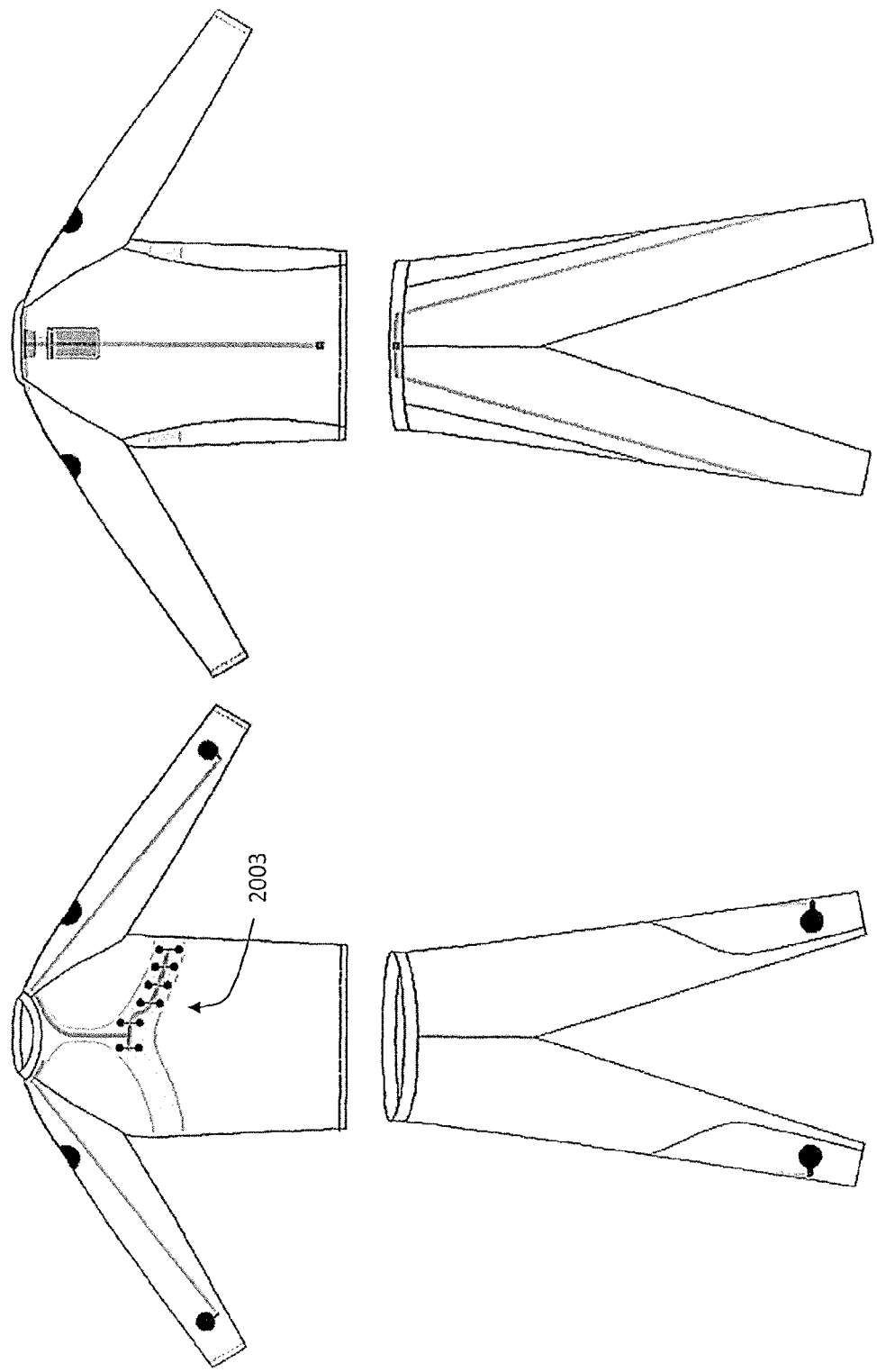

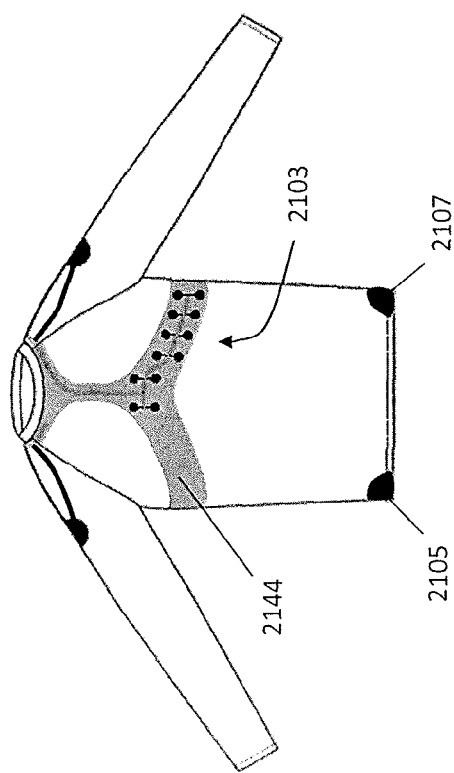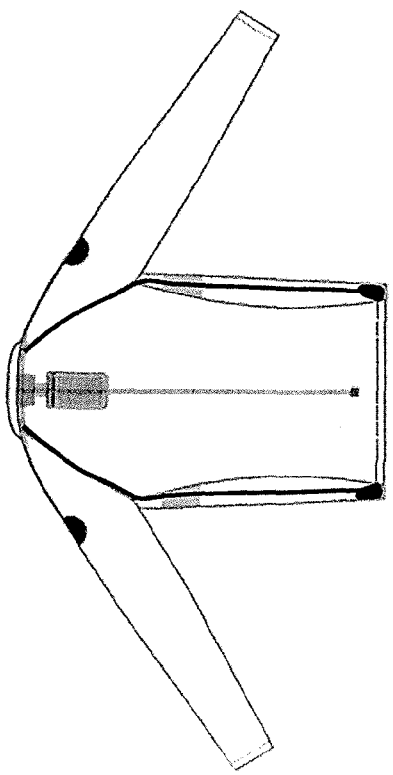
FIG. 21A
FIG. 21B

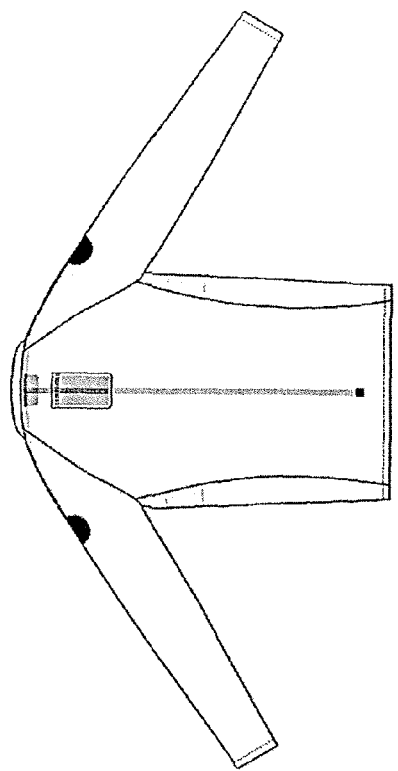
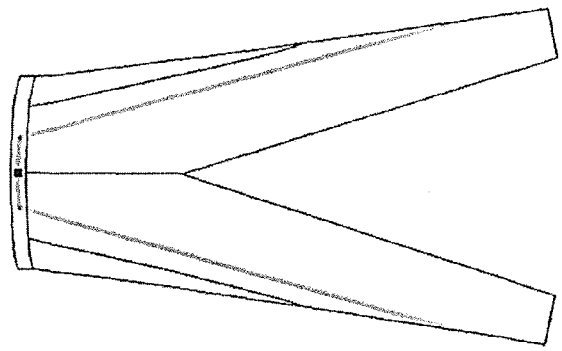
FIG. 21D
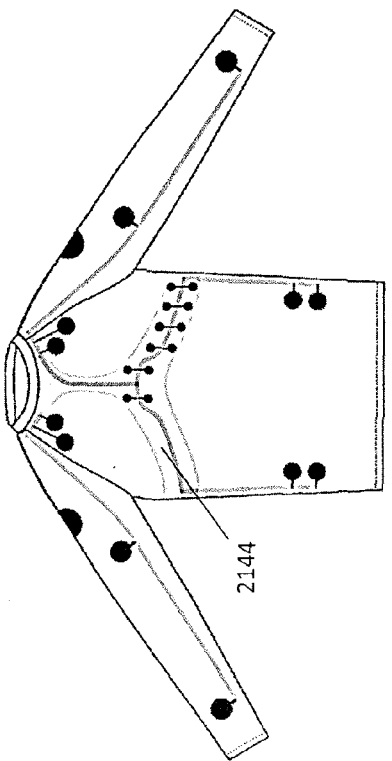
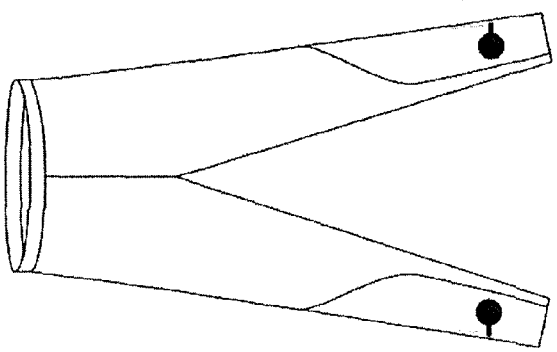
FIG. 21C

A – sensing device

B – 'smart' interpretation of the signals (interpreter)

THE WELLBEING CHART

THE FITNESS CHART

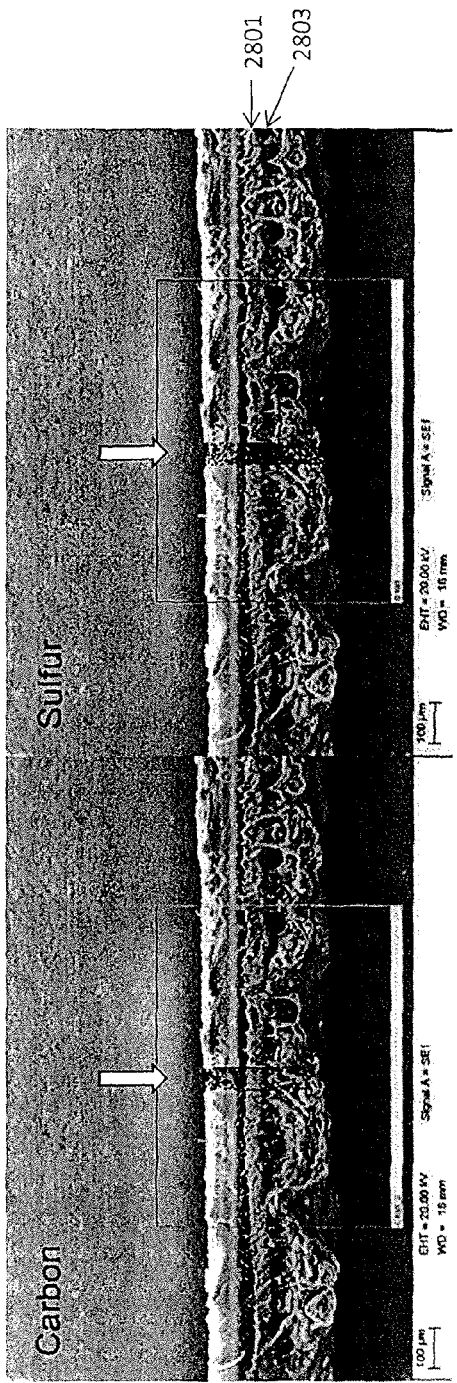
FIG. 29A
FIG. 29B
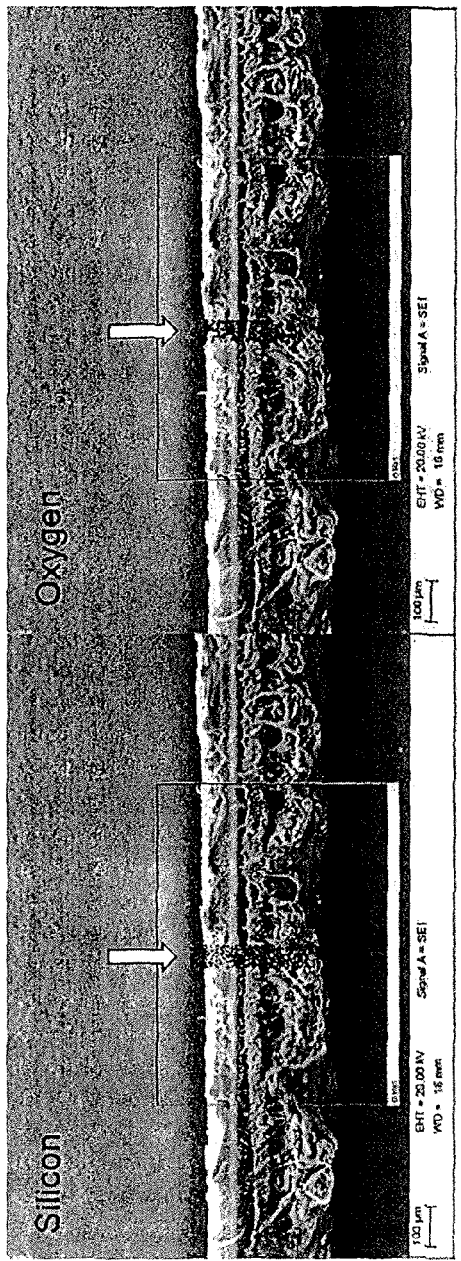
FIG. 29C
FIG. 29D

GARMENTS HAVING STRETCHABLE AND CONDUCTIVE INK

CROSS REFERENCE TO RELATED APPLICATIONS

This application claims priority to U.S. patent application Ser. No. 14/612,060, titled "GARMENTS HAVING STRETCHABLE AND CONDUCTIVE INK", filed on Feb. 2, 2015, and to U.S. patent application Ser. No. 14/331,185 (now U.S. Pat. No. 8,945,328), filed on Jul. 14, 2014. The disclosures of each of these applications are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are wearable electronics formed of compression garments onto which stretchable and conductive ink is patterned. In particular, described herein are structures having enhanced conductivity and stretchability in which the conductive ink forms a partially-mixed gradient with an insulative and adhesive base that can be applied directly or transferred onto a compression fabric, and used to form wearable electronics.

BACKGROUND

In the last twenty years, the development of mobile telecommunications devices have has dramatically expanded and modified the ways in which people communicate. Computers with ever-faster computer processors enabled faster communication with increased processing speed and improved analysis of vast quantities of data. In addition, sensor technology has also rapidly expanded how patients have been monitored, even by non-professionals. The development of various sensors enabled a variety of measurements to be taken and analyzed by a computer to generate useful information. In recent years, the use of medical sensing technology in combination with various communications platforms has provided new and interesting ways for people, including patients, to be monitored or to monitor themselves and communicate the results of the monitoring with their physician or caregiver. For example, mobile devices such as smart phones have enabled mobile device users to communicate remotely and provided some ability to obtain, analyze, use, and control information and data. For example, a mobile device user may be able to use application software (an "app") for various individualized tasks, such as recording their medical history in a defined format, playing a game, reading a book, etc. An app may work with a sensor in a mobile device to provide information that a user wants. For example, an app may work with an accelerometer in a smart phone and determine how far someone walked and how many calories were burned during the walk.

The use of a mobile communications platform such as a smartphone with one or more such biometric sensors have been described in various contexts. For example, US2010/0029598 to Roschk et al. describes a "Device for Monitoring Physical Fitness" that is equipped with a heart rate monitor component for detecting heart rate data and an evaluation device for providing fitness information that can be displayed by a display device and is derived by a processing unit, embodied for reading in and including supplementary personal data. US2009/0157327 to Nissila describes an "Electronic Device, Arrangement, and Method of Estimating Fluid Loss" that is equipped with "an electronic device comprising: a processing unit configured to receive skin temperature data generated by a measuring unit, to receive performance data from a measuring unit, and to determine a theoretical fluid loss value on the basis of the received performance data."

Similarly, clothing that-includes sensors have been previously suggested. See, e.g., US2007/0178716 to Glaser et al., which describes a "modular microelectronic-system" designed for use with wearable electronics. US2012/0071039 to Debock et al. describes interconnect and termination methodology fore-textiles that include a "conductive layer that includes conductors includes a terminal and a base separately provided from the terminal. The terminal has a mating end and a mounting end." US52005/0029680 to Jung et al. describes a method and apparatus for the integration of electronics in textiles.

For example, cardiovascular and other health-related problems, including respiratory problems may be detected by monitoring a patient. Monitoring may allow early and effective intervention, and medical assistance may be obtained based on monitored physiological characteristics before a particular health issue becomes fatal. Unfortunately, most currently available cardiovascular and other types of health monitoring systems are cumbersome and inconvenient (e.g., impractical for everyday use) and in particular, are difficult or impractical to use for long-term monitoring, particularly in an unobtrusive manner.

It has been proposed that patient health parameters, including vital signs (such as ECG, respiration, blood oxygenation, heart rate, etc.) could be actively monitoring using one or more wearable monitors, however, to date such monitors have proven difficult to use and relatively inaccurate. Ideally such monitors could be unobtrusively worn by the subject (e.g., as part of a garment, jewelry, or the like). Although such garments have been proposed, see, e.g., US 2012/0136231, these garments suffer from a number of deficits, including being uncomfortable, difficult to use, and providing inaccurate results. For example, in applications such as US 2012/0136231, a number of individual electrodes are positioned on the garment and connected to a processor by woven conductive fibers or the like; although such garments "require . . . consistent and firm conductive contact with the subject's skin," in order to provide accurate readings, such designs require that the garment be restrictive in order to prevent movement of the garment (and thus sensors) contacting these skin regions. Such a configuration rapidly becomes uncomfortable, particularly in a garment that would ideally be worn for many hours or even days. In addition, even such tightly worn garments often move relative to the wearer (e.g., slip or ride up). Further, devices/garments such as those described in the prior art are difficult and expensive to manufacture, and are often rather "fragile", preventing robust usage and washing. Finally, such devices/garments typically do not allow processing of manual user input directly on the garment, but either relay entirely on passive monitoring, or require an interface of some sort (including off-garment interfaces).

The use of garments including one or more sensors that may sense biometric data have not found widespread use. In part, this may be because such garments may be limited in the kinds and versatility of the inputs that they accept, as well as limits in the comfort, and form factor of the garment. For example, sensors, and the leads providing power to and receiving signals from the sensors have not been fully integrated with the garment in a way that allows the garment to be flexible, attractive, practical, and above all, comfortable. For example, most such proposed garments have not been sufficiently stretchable. Finally, such proposed garments are also limited in the kind of data that they can receive, and how they process the received information.

Thus, existing garments (e.g., devices and wearable sensing apparatuses) and processes for analyzing and communicating the physical and emotional status of an individual may be inaccurate, inadequate, limited in scope, unpleasant, and/or cumbersome.

What is needed are apparatuses (including garments) having one more sensors that may be comfortably worn, yet provide relatively accurate and movement-insensitive measurements over a sustained period of time. It would also be beneficial to provide garments that can be easily and inexpensively manufactured. Finally it may be beneficial to provide garments having a direct user interface that is on the garment, and particularly interfaces which are formed as part of the garment (including the fabric).

In particular, what is needed is a stretchable and conductive patterns (e.g., traces) formed of a conductive ink that can be applied onto a garment either directly or indirectly (e.g., by a transfer process). These stretchable, conductive patterns may be used even with the most stretchable of fabrics (such as compression fabrics/compression garments) and moved through numerous stretch/relaxation cycles with the underlying fabric without breaking and while maintaining a stable set of electrical properties such as conductance over time and use. The apparatuses, including wearable devices (e.g., garments) and systems including them described herein may address some or all of the problems identified above.

SUMMARY OF THE DISCLOSURE

Described herein are wearable devices (garments) that may detect and respond to signals from the user (e.g. from a wearable "intelligent" garment) and that can communicate with the user (and/or others) and may perform other useful functions. Also described herein are methods of making and using such a wearable communication platform. For example, such a communication platform may be configured to accurately detect, process, compare, transfer and communicate, in real time, physiological signals of the wearer (such as a person, an animal, etc.). A wearable communication platform may include an intelligent garment that is a wearable item that has one or more sensors (such as for sensing a condition of a user) and that is capable of interacting with another component(s) of an intelligent apparel platform to create a communication or other response or functionality based on the sense obtained by the sensor. Any of the garments described herein typically refer to an item that can clothe a user's body, but for purposes herein, a garment may, in some variations, be understood to include any item capable of including the same features described herein. Thus, a garment may include footwear, gloves, and the like. In some variations the garment is specified as a particular type of garment, such as an undergarment, and may be adapted for use in that context (e.g., operating through additional layers of clothing, etc.). A wearable communication platform may include a wearable intelligent garment; sensors on the garment; flexible conductive connectors on the garment, and optionally a sensor module for managing the sensors and an output, such as a haptic output or audio (e.g., music) output based on sensor input and which may be on the intelligent garment or may be separate from it. When the sensor module and/or output are separate from the garment, the garment may be specifically adapted for connection/communication or to secure to the sensor module and/or output. For example, the apparatus (garment) may include a holder, pocket, connector region, base, etc., for interfacing specifically with the sensor module and/or output (or input/output module).

In some variations the wearable devices refer to sartorial communications apparatuses. Such wearable communications apparatus may be referred to as continuously conforming to the wearer's body. As used herein "continuously conform" may mean conforming and contacting to the skin surface, at least over a region of a material that conforms. For example, a garment that is configured to continuously conform may include an inner surface (with sensors) that is held against the skin. Such a garment does not have to be tight or clinging, but may be biased against the skin over all or a majority of the garment. Continuously conforming may refer to the fact that the sensor-containing regions of the garment conforms to the skin even as the subject moves while wearing the garment. In a continuously conforming garment, a portion of the garment (e.g., less than 30%, less than 20%, less than 10%, etc.) may be more loosely conforming—e.g., underarms, lower back, joints (elbow, shoulders, etc.).

As used herein "physiological status" may refer to any parameter indicating the physiological status of the user. Typically relates to physiological characteristics including vital signs, autonomic response, and the like.

As used herein a "body sensor" generally determines information about the user without requiring the users conscious input. A body sensor may detect physiological status, including vital signs (pulse/heart rate, blood pressure, body temperature, galvanic skin response (e.g., sweat), etc.). A body sensor may detect user position (e.g., arm position, body position in space, posture, etc.). A body sensor may detect user movement (e.g., movement of individual body parts (arms, legs, etc.) and/or movement of the entire user (e.g., rate of motion, direction of motion, altitude, etc.).

As used herein, an interactive sensor may mean a sensor that is manually activated sensors that may be activated by touch. This may also be referred to herein as volitional touch. Examples of volitional touch include manually touching a sensor or sensor contact region with a hand, foot, or other body part to cause activation of the sensor. Examples of what is not meant by volitional touch may include incidental contact between the wearer's (users) body when wearing the garment. In some variations the interactive sensors are touch point triggers or touch point sensors. "Manually activated" may refer to a pushing, rubbing, touching, tapping, or otherwise contacting with the hand or (in some variations) other body part(s), such as the foot, arm, leg, face, jaw, nose, etc. In general volitional (manual) activation is performed consciously by the user, and may in some variations also or alternatively be referred to as conscious or intentional activation. For example, the user may touch an interactive sensor with his/her hand for a period of time (e.g., seconds) to send a signal from that touch point. The signal may be coordinated with one or more other volitional activations, from the same or additional interactive sensors. Combinations or patterns of manual activation may be used to communicate or signal.

A wearable communication platform may include an intelligent garment which may be any type of comfortable, conformable, and/or flexible garment. A wearable communication platform may include a garment configured to be a shirt, pants, shorts, hat, etc. As mentioned, a wearable communication platform may be configured to conform to a user's body. A wearable communication platform may hold or contain sensors which may be attached, for example, to an outside or to an inside of a garment or otherwise integrated into the garment. A wearable communication platform may include flexible conductive connectors that may carry a sensor signal from a sensor on the garment to a sensor module or to another connector, such as a Kapton® connector and/or conductive thread.

A wearable communication platform may include sensors on or formed as part of a garment which may be useful for providing signals to or from an intelligent communication platform. Such sensors may include body sensors, interactive (e.g., touchpoint or touch point) sensors, and/or haptic sensors. A body sensor may sense a user's aspect, such as a user's position, a user's movement, and/or a user's physiological status.

A wearable communication platform useful for producing/outputting signals may include a flexible conductive connector for transferring a signal between sensor and a sensor module or away from a sensor module. A conductive trace useful as a flexible conductive connector may include a conductive media (conductive ink) and an insulator.

A wearable communication platform may include a sensor module that is in proximity with, attached to, or within the rest of the garment and may be configured (either alone, or in conjunction with another component) to generate an output, such as a haptic output or an audio and/or visual output based on sensor input(s). The output, which may include a speaker, haptic output or the like, may be on the garment, integrated with the garment, or it may be separate from it.

A wearable communication platform may also include: specially designed apparel and/or accessories, an intelligent garment platform power distribution and conductive control system that controls the apparel/accessory and interfaces with a sensor module, an internet or other communication system for interacting directly with a cloud, an enabled intelligent device such as an smart phone (iPhone, Android, etc.) and that may be a separate device or built into the apparel, and may be running specially developed software applications for functional activity, data capturing and analysis, validation, programming, downloading and uploading, activations, social connectivity, sharing, and distribution, and/or a feedback mechanism for consumer, commercial, medical, and industrial applications. In some variations the sensor module is a smartphone adapted for use with the wearable communication platform, e.g., running a program (e.g., an app) that configures the smartphone to communicate (input and/or output) with the wearable communication platform, including receiving and/or processing inputs from the wearable communication platform.

One aspect of the invention provides a flexible garment configured to continuously conform to a user's body when the garment is worn by the user, the garment including a body sensor on the garment configured to sense one of a user's position, a user's movement, and a user's physiological status and thereby generate a body sensor signal; a conductive trace on the garment, connected with the sensor and configured to communicate the body sensor signal from the body sensor to a sensor module for analysis; and an interactive sensor on the garment configured to transmit an interactive sensor signal to the sensor module when the user's hand activates the interactive sensor to control an audio output and/or a visual output in response to the interactive sensor signal.

In general, a garment may include a shirt, pants, underwear, a hat, etc. It may be made of any comfortable material that can support components such as haptic actuators, sensors, and a sensor module. Such components may be flexible and/or conformable in one or more dimensions so as to maintain the comfort of the garment. A flexible garment may be worn under a user's regular street clothes or it may be worn on the outside where it may be visible to others. A conductive trace may be, for example, a conductive media (a conductive ink), a conductive cable, conductive metal particles, etc. An interactive sensor may, for example, be activated by a touch of a user's hand or by near proximity of a user's hand. An output may be any sort and may be on an intelligent garment such as a video screen, may be on a communication collar connected with the garment and configured to provide an audio signal to a user's ears, on a smart phone, on a separate speaker, etc.

As used herein a particle (e.g., a conductive metal particle) may refer to spherical and non-spherical particles, including in particular nanoparticles such as nano-wires, nano-flakes, nanotubes and the like. As will be described in greater detail below, the conductive particles described herein may correspond to conductive particles made of mica, carbon black, graphene, graphite, silver, silver metal powder, copper metal powder, or iron metal powder, etc. In particular, particles may be particles of mica, such as mica coated with antimony-doped tin dioxide.

In some embodiments, the flexible garment includes a compressive material. In some embodiments, the flexible garment is configured to expand and contract. In some embodiments, the flexible garment includes a first axis and a second axis perpendicular to the first axis wherein the garment is configured to change in size along the first axis and to substantially maintain a size along the second axis. In some embodiments, flexible garment includes at least one of pants, a shirt, or shorts. In some embodiments, the flexible garment includes a shirt having a front and a back, and further includes a pocket configured to hold a sensor module on the back of the shirt.

In some embodiments, the body sensor is in electrical contact with the skin of the individual. In some embodiments, the sensor includes one of an accelerometer, an electrocardiogram (ECG) sensor, an electroencephalography sensor (EEG), and a respiratory sensor. In some embodiments, the body sensor includes a first sensor, and the garment further includes a second sensor configured to sense one of a user's position, a user's movement, and a user's physiological status and thereby generate a second body sensor signal. In some embodiments, the conductive trace is configured to conform to the user's body when the flexible garment is worn by the user. In some embodiments, the conductive trace is on a surface of the garment. In some embodiments, the flexible garment further includes a seam enclosing the conductive trace.

In some embodiments, the interactive sensor is configured to transmit a first interactive sensor signal when the user's hand activates the interactive sensor once and to transmit a second interactive sensor signal when the user's hand activates the interactive sensor twice in succession wherein the first interactive sensor signal is different from the second interactive sensor signal. In some such embodiments, the flexible garment further includes a plurality of interactive sensors wherein the first interactive sensor is configured to send a first interactive sensor signal and the second interactive sensor is configured to send a second interactive sensor signal which is different from the first interactive sensor signal. In some of these embodiments, the interactive sensors are on a front of the garment.

In some embodiments, the sensor module is configured to control a microphone or a music playing device in response to the interactive sensor signal.

In some embodiments, the garment, the body sensor, the conductive trace, and the interactive sensor are configured to withstand immersion in water. Thus, in general, the wearable communication platforms described herein may be washed (e.g., washed in water).

The interactive sensor may be configured to be activated by a user's hand through an intervening layer of clothing.

A flexible, compressive garment may be configured to continuously conform to a user's body when worn by the user. A flexible, compressive garment (e.g., shirt) may be configured to move with a user's body. A body sensor may be, for example, a printed sensor or a physical sensor and may be sufficiently flexible or extensible in at least one direction in order to maintain the flexibility of the shirt. A body sensor may be, for example an accelerometer, a gyroscope, a magnetoscope, and may detect, for example, a user's respiratory rate, heart rate, skin conductivity, movement, position in space, inspiratory time, expiratory time, tidal volume, perspiration, pulse, moisture, humidity, elongation, stress, glucose level, pH, resistance, motion, temperature, impact, speed, cadence, proximity, flexibility, movement, velocity, acceleration, posture, relative motion between limbs and trunk, location, responses to transdermal activation, electrical activity of the brain, electrical activity of muscles, arterial oxygen saturation, muscle oxygenation, oxyhemoglobin concentration, deoxyhemoglobin concentration, etc. A sensor module may be configured for managing and controlling power, body sensors, memory, external data, interactive sensors, body "expressions", feedback, transdermal control processes, module enhancements, social media, software development, etc. An interactive sensor ("touchpoint") may be activated by touching or by relative proximity of a user's hand or other item (even though one or more layer of clothing).

A wearable, flexible garment may include: a body sensor on the garment configured to sense one of a wearer's position, a wearer's movement, and a wearer's physiological status and thereby generate a body sensor signal; a conductive trace on the garment, connected with the sensor and configured to communicate the body sensor signal from the sensor to a sensor module for analysis; an interactive sensor on the garment configured to transmit an interactive sensor signal to the sensor module when the wearer's hand activates the interactive sensor wherein the sensor module is configured to control an audio output and/or a visual output in response to the interactive sensor signal; a pocket on the garment configured to removably contain the sensor module; and a sensor module for receiving the body sensor signal from the body sensor, processing the signal to generate an output signal, and outputting the output signal to thereby provide a feedback output. The wearable flexible garment may be configured to continuously conform to a wearer's body when the flexible garment is worn by the wearer. In some embodiments, the garment is configured to be worn on the wearer's torso.

The flexible garment may include a plurality of body sensors for generating a plurality of body sensor signals, and the body sensors are connected with a plurality of conductive traces, wherein the sensor module is configured to receive the plurality of signals from the plurality of conductive traces and process the signals to generate a feedback output wherein the feedback output comprises one of an audio output, a visual output, and a tactile output. Some such embodiments further include one of a speaker and an earphone connected with the sensor module wherein the audio output comprises a music output configured to be sent to the earphone or speaker.

In some embodiments, the output signal is configured to be sent to another individual, a computer, or a website.

In some embodiments, the garment further includes a haptic actuator configured to provide a tactile sensation to the wearer based on the output signal. A second garment in electrical communication with the first garment may be used. The first garment may include a shirt and the second garment may include one of pants or shorts.

Some embodiments further include a communications device including: a collar comprising a microphone or a speaker and configured to wrap partially around a wearer's neck; and a base region connected with the collar and configured to connect with and provide electrical communication between the sensor module and at least one of a microphone, an earphone, and a speaker.

Also described herein are methods of manufacturing the garments described herein. For example, a method of manufacturing a flexible compressive garment including the steps of: placing a first insulating fluid media onto a substrate, the fluid comprising an adhesive; placing a conductive material on the first insulating fluid media to thereby create a conductive material electrical trace; solidifying the first insulating fluid media to create a first flexible insulator region and thereby generate a flexible transfer comprising a conductive material electrical trace wherein the transfer is configured to be removed intact from the substrate; removing the transfer from the substrate; placing the transfer on a flexible compressive garment; attaching the transfer to the flexible garment; electrically connecting the transfer to a sensor on the flexible garment wherein the transfer is configured to be connected with a sensor module.

A flexible transfer may be manufactured separately on a substrate and subsequently transferred to an intelligent garment. Such a trace may be place on the outside of the garment, on the inside of a garment, or in between two or more layers. A trace may be elongated, a plate or series of plates, a spiral, a zigzag etc.

In some embodiments, the solidifying step includes generating a conformable transfer. Some embodiments further include the step of placing a second insulating fluid media on the conductive material after the solidifying step, the method further comprising solidifying the second insulating fluid media to thereby create a second flexible insulator region. In some such embodiments, the first insulating fluid media and the second insulating media include the same material.

In some embodiments wherein the conductive material includes a conductive fluid media, the method further includes solidifying the conductive fluid media. In some embodiments placing a conductive material on the first insulating fluid includes placing conductive particles on the first insulating media. In some embodiments, placing a conductive material includes placing a conductive wire on the first insulating media.

In some embodiments, attaching the transfer to the flexible garment includes adhering the transfer with an adhesive. In some embodiments, attaching the transfer to the flexible garment includes sealing the transfer in a seam in the garment.

A method of manufacturing a garment may include: placing an insulating fluid media onto a transfer substrate, the fluid comprising an adhesive; placing a conductive material on the first insulating fluid media to create a conductive electrical pattern; solidifying the first insulating fluid media to create a flexible insulated connective pattern; and removing the insulated conductive pattern from the transfer substrate and attaching the insulated conductive trace on a flexible compressive garment.

Any of the methods of manufacturing the garments described herein (e.g., sartorial communications apparatuses) may include placing additional insulating fluid media on the conductive material and solidifying the second insulating fluid media. The conductive material may comprise a conductive fluid media, and any of the methods may further comprise solidifying the conductive fluid media. Placing a conductive material on the insulating fluid may comprise placing conductive particles on the insulating media. Placing a conductive material may comprise placing a conductive wire on the insulating media.

Attaching the transfer to the flexible garment may comprise adhering the insulated conductive trace to the garment with an adhesive. Attaching the transfer to the flexible garment may comprise sealing the insulated conductive trace in a seam in the garment. In general, removing the insulated conductive trace from the transfer substrate and attaching the insulated conductive trace on the flexible compressive garment may comprise applying heat to transfer the insulated conductive trace to the garment.

Another aspect of the invention provides a wearable communications device including: a collar configured to wrap at least partially around a user's neck and to hold a shape and including at least one of a speaker and a microphone; and a base region connected with the collar and configured to provide electrical communication between a sensor module and the collar wherein the sensor module is configured to connect with a conformable garment including a plurality of body sensors. A collar may be configured (and referred to as) an input/output collar.

For example, an output/input collar for a sartorial communications apparatus may include: a collar body configured to wrap at least partially around a user's neck; a microphone within a housing of the collar body; and a speaker output within the housing of the collar body; and a base region configured to connect the collar body to a garment and to provide electrical communication between a sensor module on the garment and the input/output collar when the sensor module is connected with a plurality of body sensors on the garment.

In some embodiments, the collar and/or communications device further includes an earphone. For example, the earphone (an audio output) may be connected with a base region of the collar. Some such embodiments further include a sensor module connected with the base region and configured to provide an audio output signal to the base region wherein the base region is configured to communicate the audio output signal to at least one of the collar and the earphone. In some such embodiments, the sensor module and the base region are rigidly connected together.

As mentioned, the apparatuses described herein may be washed. Thus, also described herein are methods of washing any of the wearable communications platform apparatus (sartorial communications apparatuses) described herein. A method of washing may include: placing the wearable communications apparatus (e.g. having one or more interactive sensors) into an aqueous solution (e.g., a washing machine) with a cleaning agent (e.g., detergent); and moving the garment through the aqueous solution and cleaning agent; rinsing (e.g., in water), and/or separating the conformable garment from the aqueous solution and cleaning agent; and drying the conformable garment. The method of washing may also include removing an input/output collar and/or removing the sensor module.

In some embodiments, the cleaning agent includes a detergent and the method further includes rinsing the conformable garment with an aqueous solution after the separating step.

Methods of using sartorial communications apparatuses are also described. In general, these devices may be worn by a user (e.g., subject, person, patient, etc.). The apparatus may be worn with a sensing module attached; in some variations this may include placing the sensing module in a pocket or other retainer on the apparatus. The apparatus maybe worn beneath clothing (as an undergarment). In use, the garment may sense/detect volitional inputs from the use on one or more touch points (e.g., an interactive sensor). The apparatus may detect one or more of a user's body position, movement, and physiological status with a body sensor. The sensed information may be passed to the sensor module through the conductive traces integrated into the garment. Once received by the sensor module, the sensor module may store, analyze and/or transmit the sensed information. In general the volitional contact signal(s) may be used to modify the operation and/or output of the sensor module and therefore the sartorial communications device. The sensor module may prepare an output based on the sensed signal(s). For example, the output may be related to the body sensor signal(s). Examples may include outputting an audio and/or visual output. The output may be a representation of the sensed signal (e.g., heartbeat, respiratory rate, etc.) or it may be determined or modified by the sensed signal. For example, the output may be a musical output that is correlated with the sensed signal.

Another aspect of the invention provides method of providing feedback for encouraging behavior modification. For example, a sartorial communications system may be configured to provide biofeedback. In one variation the system may be configured to help improve posture. For example, one method of using the apparatus may include a method of modifying a behavior of a person wearing a sartorial communications apparatus, wherein the sartorial communications apparatus comprises a compression garment including a haptic feedback and a plurality of body sensors integrated in the garment. The method may include: sensing one or more of the person's body position, movement, and physiological status with the plurality of body sensors; transmitting sensor signals from the body sensors to a sensor module attached to the garment; generating an output signal based on the senor signals; converting the output signal into a feedback for output by the haptic feedback on the garment; and delivering the haptic feedback to encourage the person to modify a behavior.

In some embodiments wherein plurality of signals comprises a body position signal, the step of delivering the haptic feedback includes delivering a vibration to the individual to encourage the individual to change a position. In some embodiments, communicating the feedback output includes providing a haptic feedback.

Also described herein are sartorial communications apparatuses that include one or more interactive sensors arranged on the garment that allow the user wearing the garment to provide input to the sartorial communications apparatus even through multiple layers of clothing. For example, a sartorial communications apparatus may include: a flexible garment comprising a fabric; a plurality of interactive sensors integrated into the garment, each configured to sense a volitional contact by the user and to generate a volitional contact signal when the user manually contacts one or the interactive sensors; a sensor module interface configured to connect to a sensor module for receiving and analyzing, transmitting or analyzing and transmitting the volitional contact signals; and a plurality of conductive traces on the garment connecting the interactive sensors to the sensor module interface.

In any of the sartorial communications apparatus described herein, the apparatus may also include a plurality of surface regions on the garment, wherein each surface region corresponds to a contact surface for one of the interactive sensors. Each of the plurality of surface regions may comprise a visual marker on the fabric of the garment indicating the location of the interactive sensor corresponding to the surface region. For example, each surface region corresponding to a touch point (interactive sensor) contact surface may be marked by a color, icon, or the like. In some variations, the contact surface include a tactile marker, such as a textured or raised region. The contact surface of an interactive sensor may be any appropriate size. For example, a contact surface for an interactive sensor may be between about 10 mm and about 150 mm in diameter. In general, an interactive sensor (also referred to as a touchpoint sensor) may be configured so that it can only be activated by contact with the outwardly-facing side of the sensor (e.g., the side of the sensor that faced away from the body when the garment is worn).

Any of the sartorial communication apparatus described herein may also include at least one body sensor on the garment configured to generate a body sensor signal describing one or more of the user's position, the user's movement, and the user's physiological status. The body sensor may include one (or more) of: an accelerometer, an electrocardiogram (ECG) sensor, an electroencephalography sensor (EEG), and a respiratory sensor.

In any of the variations of wearable communication platforms (sartorial communications apparatuses) described herein the flexible garment may comprise a compression garment that is configured to continuously conform to a user's body when the garment is worn by the user. In general, the flexible garment may include a first axis and a second axis perpendicular to the first axis wherein the garment is configured to stretch in size in the first axis but not to substantially stretch in the second axis. The conductive traces may extend substantially in one axis (e.g., in the second axis). Alternatively or additionally, the garment may be configured so that different regions of the garment are configured to stretch in a first direction but not in a second (substantially perpendicular) direction, or to not stretch in any direction; these different regions may be adjacent and the stretch vs. non-stretch regions may have different orientations, so that they do not all extend in the same axis relative to the garment. The conductive traces may extend substantially along the non-stretch directions of each region.

As mentioned, the garment may be configured as any garment type, including, but not limited to, undergarments. For example, the garment may be configured as an undershirt. Also in general, the garment of the apparatus may be configured to have a front and a back. The sensor module interface may include a pocket configured to hold the sensor module; the pocket may be on the back (e.g., the upper back region) of the garment.

In general, the conductive trace may include a conductive ink layer on an inner surface of the garment, an outer surface of the garment, or on the inner and outer surfaces of the garment. As mentioned, in some variations the conductive trace is flexible and/or stretchable. In some variations the conductive trace is flexible but not stretchable. Any of the variations of the apparatuses described herein may include a seam enclosing the conductive trace.

In any of the variations described herein, an interactive sensor may be configured to transmit a first interactive sensor signal when manually activated by a first pattern of contact and to transmit a second interactive sensor signal when manually activated by a second pattern of contact, wherein the first interactive sensor signal is different from the second interactive sensor signal. For example, the sensor may be configured so a single touch will send a first signal and a series of two touches within a certain time period may result in a second (distinct from the first) signal.

The interactive sensors may be placed anywhere on the garment. For example, the interactive sensors may be arranged on a front of the garment.

In general, the interactive sensor are configured to be manually activated by a user even through an intervening layer of clothing. This means that even when a user is wearing the sartorial communications apparatus underneath another garment or garments (e.g., a shirt), a volitional contact to the sensor (e.g., the region of the sensor over the contact surface) on the shirt over the garment forming the sartorial communications apparatus may result in activation of the touch point sensor.

The interactive (touch point) sensors described herein may comprise capacitive or inductive sensors.

A sartorial communications apparatus may include an undershirt comprising a fabric; a plurality of interactive sensors integrated into the undershirt, each configured to sense a volitional contact by the user through an intervening layer of clothing and to generate a volitional contact signal when the user manually contacts one or the interactive sensors, wherein the interactive sensors are capacitive or inductive sensors; a sensor module interface configured to connect to a sensor module for receiving and analyzing, transmitting or analyzing and transmitting the volitional contact signals; and a plurality of conductive traces on the garment connecting the interactive sensors to the sensor module interface.

Methods of communicating with sartorial communications apparatuses are also described. For example, a method of communicating with a sartorial communications apparatus, wherein the sartorial communications apparatus comprises a garment including an interactive sensor integrated in the garment and connected via an integrated conductive trace with a sensor module, may include the steps of: sensing one or more volitional contact signals with the interactive sensor when a user touches the interactive sensor through an intervening layer of clothing; transmitting the volitional contact signal from the interactive sensor to the sensor module; and generating or modifying an output from the sensor module in response to the volitional contact signal. The method may also include presenting the output from the sensor module in response to the volitional contact signals. For example, the output may comprise an audible signal, and/or a visible signal.

Specific examples of the kinds of apparatuses (e.g., devices and systems, including garments) that are described herein include physiological parameter monitoring garments having sensors formed of printed conductive ink on a compression garment that are arranged and configured for robust sensing and comfortable wear. In particular, the garments (e.g., shirts, pants, undergarments) described herein are configured to allow robust sensing of one or more physiological parameter using a conductive ink sensor printed directly onto the garment and connected by a conductive trace (which may or may not be reinforced on the garment) to an interface region of the garment which may connect to an analysis unit such as a microprocessor that is configured to measure, store, process and/or transmit the recorded parameter(s).

For example, described herein are shirts adapted to continuously monitor the regional respiration of a wearer. A shirt for monitoring respiration may include: a shirt body comprising a fabric, wherein the body is configured as a compression garment that expands and contracts to hold the shirt against the wearer's torso; a plurality of respiratory sensors arranged on different regions of the body, wherein each respiratory sensor comprises: a plurality of generally parallel conductive ink traces printed on an outer portion of the body; and a regional conductive connector, wherein each of the generally parallel conductive ink traces connect to the regional conductive connector; and an interface (e.g., module interface) located on the body, wherein the regional conductive connector for each respiratory sensor connects to the interface, further wherein the interface is configured to connect with a processor (e.g., sensor manager unit) to detect electrical resistance from each of the conductive connectors.

In general, the respiratory sensors regional. Different regions (e.g., quadrants) of the shirt body may be covered by different sensors, permitting detection and monitoring of "regional" respiration. As the shirt (which is fit snugly to the body) expands and contracts with a wearer's respiratory effort, region respiration (movement) is detected by a variation in the resistance of the conductive ink traces in each of the different regions. The plurality of generally parallel conductive ink traces comprise between three and 50 parallel traces. Sensing by the respiratory sensors may be particularly robust by arranging multiple (e.g., 2, 3, 4, 5, 6, 7, 8, 9, 10, 11, 12, 13, 14, 15, 16, 17, 18, 19, 20, 25, 30, 35, etc.) conductive ink traces in an approximately parallel fashion across the region of the shirt body; each of these parallel traces is connected (in parallel) to the region conductive connector (and on the other end to a reference, e.g., reference line), effectively determining the overall resistance from the parallel resistance, e.g., $R_{total}$=(product of all resistance for each trace)/(sum of each resistance for each trace).

In some variations the shirt is configured to detect the respiration off four regions (e.g., anterior/posterior and pectoral/abdominal regions; or pectoral/abdominal and left/right regions, etc.). In some variations the respiratory sensors comprise eight respiratory sensors, sensing eight regions (anterior/posterior, pectoral/abdominal and left/right regions). In general, the plurality of respiratory sensors may be separately arranged in anterior or posterior, upper or lower, right or left regions of the body. More than eight regions may be determined as well (e.g., dividing the body into further subdivisions); the regions do not need to be the same size.

The plurality of generally parallel conductive ink traces are each stretchable traces; stretching of the conductive ink typically changes the resistance (detecting stretch, and thereby respiration). The plurality of generally parallel conductive ink traces may be printed on the outer portion of the body in any pattern. For example, the traces may be printed as parallel straight lines, zig-zag lines, curved lines, e.g., for example, the traces may be printed in an undulating pattern. In general, the plurality of generally parallel conductive ink traces may be configured create varying electrical resistance through the traces as the subject breathes; for example, the lines may extend in a direction that will be transverse to the patient's body (across the chest) when the shirt is worn.

As mentioned, the plurality of respiratory sensors may comprise a reference line to which each of the generally parallel conductive ink traces connect at an opposite end of the generally parallel conductive ink trace from the regional conductive connector. The reference line may be a "ground". The reference line typically also connects to the interface (and ultimately the processor that is detecting the change in resistance of the lines due to respiration).

Each respiratory sensor may be configured to average the variable electrical resistance in the plurality of generally parallel conductive ink traces forming the respiratory sensor. Thus a very small current or voltage may be applied across the conductive traces to determine the change in resistance with respiration. The conductive traces may generally be insulated (e.g., prevented from contacting the wearer's skin directly and/or shorting due to sweat, etc.).

Any of the shirts described herein may also include a user input, such as a touchpoint sensor at a touchpoint location on the body, configured to sense when the wearer touches the shirt at the touchpoint location. The touchpoint sensor may be used as an input and/or control for the device. For example, the user may "mark" a time when something occurs, such as a shortness of breath, or other respiratory episode, or to indicate when activity is increasing (e.g., exercising, etc.) or decreasing, or to start/stop/pause, etc. the recording and/or analysis of respiration, or to save, transmit, process, etc. detected regional respiration. Multiple touchpoint sensors may be used.

The shirt may also include one or more additional sensors, such as a heart rate sensor. For example, the shirt may include a conductive ink electrode on an inner surface of the body configured to contact the wearer's skin, and an electrode conductive connector extending from the conductive ink electrode to the module interface. The electrode may be used to detect heart rate, or the like. Multiple electrodes may be used (e.g., an electrode pair). For example, the conductive ink electrode may be located on a sleeve of the shirt (or sleeves).

The shirt may also include a holder (e.g., pocket) on the body configured to hold a sensor manager unit in connection with the module interface.

Other sensors that may be used include any other activity/motion sensor (e.g., an accelerometer). The other sensors may be on the shirt and/or connected to the shirt of directly to or part of the processor receiving the signals from the sensors.

The regional conductive connectors typically comprise a conductive material on a substrate that is attached to the body. The substrate may support the conductive material and may interface with the garment so that the conductive ink is electrically coupled with the conductive material forming the connector. For example, the substrate may be a polymeric material. In some variations (e.g., see Appendix A) the substrate is Kapton.

Also described herein are methods of sensing regional respiration using shirts configured as described above. For example, a method of detecting region respiration may include wearing any of the shirts described herein, and receiving/transmitting/storing/analyzing the variations in resistance through the conductive ink traces arranged in parallel in different (typically non-overlapping) regions on the body of the search.

Also described herein are garments (e.g., shirts and/or pants) that are configured to continuously monitor a wearer's electrocardiogram (ECG). For example, a shirt may include: a body comprising a fabric, wherein the body is configured as a compression garment that expands and contracts to hold the shirt against the wearer's torso; a first set of six electrical sensors arranged on the body in a first curve extending across the left pectoral region of the wearer's chest when the shirt is worn, wherein each electrical sensor comprises a conductive ink electrode printed on an inner surface of the body; a second (redundant) set of six electrical sensors arranged on the body in a second curve that is adjacent to the second curve; a support harness region of the body extending from a neck region and overlying the first and second sets of electrical sensors; a right arm electrode formed from conductive ink printed on an inner surface of the body; and a left arm electrode formed from conductive ink printed on an inner surface of the body; wherein each electrical sensor is connected to an interface on the body by a conductive extending from the electrical sensor to the interface and further wherein the interface is configured to connect with a sensor manager unit to detect electrical activity from each of the electrical sensors, the right arm electrode and the left arm electrode.

In general such shirts may provide multiple electrodes on the chest (pectoral region) that may be connected (e.g., in parallel) to act as individual leads (e.g., V1-V6) for the chest electrodes of a 12-lead ECG. The apparatus may be configured to robustly detect the signal even if there is a shifting or movement of the electrodes as the garment moves on the body of the wearer. Further, the garment may be comfortably held in position, and the position of the electrodes held relatively fixedly, even where the curvature of the wearer's body may otherwise prevent good contact between the wearer and the electrodes, by the additional support region of the body of the garment (e.g., the yoke/harness support).

Any of the garments described herein may also be referred to as wearable electronics devices. As mentioned, these devices (garments) may typically include: a compression fabric and at least one stretchable and conductive ink pattern on the garment. The conductive ink pattern typically includes a layer of conductive ink and a layer of (insulating) adhesive, and an intermediate zone between the two where the conductive ink and the elastic adhesive are partially combined, for example in a gradient region. The intermediate zone may be approximately as thick as the conductive ink layer, while the adhesive layer maybe thicker.

For example, a conductive ink pattern may include: a layer of conductive ink having: between about 40-60% conductive particles, between about 30-50% binder; between about 3-7% solvent; and between about 3-7% thickener; a layer of an elastic adhesive on the garment; and a gradient region between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive.

In general, the compression garments described herein may be configured to exert a pressure of between about 3 mm Hg and about 70 mm Hg on a subject's body surface to allow a stable and continuous positioning of the garment onto the subject's body.

The composition of the conductive ink portion may typically include conductive particles in a binder, thickener and solvent, as mentioned. The conductive particles may comprise particles of carbon black, or of one or more of: mica, carbon black, graphene, graphite, silver metal powder, copper metal powder, or iron metal powder. The binder typically comprises formaldehyde-free binder, for example, acrylic binder. The solvent may be, for example, propylenyc glycol. An example of a thickener is polyurethanic thickener.

In general, any appropriate adhesive (e.g., elastic adhesive) may be used. For example, an elastic adhesive may include a thermo-adhesive water-based glue that is electrically insulative. In any of these variations, an insulating resin may be positioned at least partially over the layer of conductive ink.

The conductive ink pattern may include a plurality of layers of the conductive ink. These layers may be applied atop each other to form the final thickness of the conductive ink.

The thickness of the layer of the elastic adhesive may be greater than the thickness of the gradient region and the thickness of the gradient region may be approximately the same or greater than the thickness of the conductive ink. Alternatively, in some variations the thickness of the gradient region is approximately the same as or less than the thickness of the conductive ink. For example, the ratio of elastic adhesive to intermediate (gradient) region to conductive ink may be approximately 1.1 to 5 (adhesive):0.8 to 1.2 (intermediate region):0.5 to 3 (conductive ink). In one example, the thickness of the ink portion of the conductive ink pattern is between about 15-120 µm, the thickness of the transition zone (the gradient/intermediate region) is between about 20-100 µm (e.g., between about 30-90 µm), and the thickness of the adhesive (glue) region is between about 100 to 200 µm.

In general, the resistivity of the conductive trace may be less than about 10 Kohms/square. For example, the bulk resistivity may be between about 0.2 to about 20 ohms*cm, and the sheet resistivity may be between about 100 to 10,000 ohms/square (ohms per square). In one example the bulk resistivity was measured as 11.5 ohms*cm and sheet resistivity at 1913 ohms/square. The resistivity of the conductive pattern may vary with applied stretch.

In general, the resulting conductive ink patterns are extremely stretchable, while maintaining their electrical properties and without breaking. For example, the conductive ink pattern may be configured to stretch up to 500% of a resting length without breaking.

Any of the conductive ink patterns described herein may be formed as all or part of a sensor, a trace, and/or as an electrode. The conductive ink pattern may be connected to another (e.g., more rigid) conductive material. For example a conductive ink pattern may be connected to a sensor module or interface for a sensor module using a conductive ink pattern formed as a trace or by connecting to a conductive thread or wire that is also attached to the garment. For example, a device (garment) as described herein may include a conductive thread coupled to the garment and connected at one end to the conductive ink pattern.

A wearable electronics devices may include: a garment comprising a compression fabric; and at least one stretchable and conductive ink pattern on the garment having a sheet resistivity of less than about 10 Kohms/square, wherein the conductive ink pattern is stretchable up to at least about 100%, 120%, 150%, 170%, 180%, 190%, 200%, etc. without breaking, and comprises: a layer of conductive ink having: between about 40-60% conductive particles, between about 30-50% binder; between about 3-7% solvent; and between about 3-7% thickener; a layer of an elastic adhesive on the garment; a gradient region between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive; and an insulating resin over at least a portion of the layer of conductive ink.

In general, any of the conductive ink patterns described herein may configured as sensors that are positioned on the garment. For example, the sensors may be configured to contact the subject's skin (on one side) to allow detection of electrical signals from the wearer's body (e.g., ECG signals, skin conductance, etc.). The sensors may be configured to detect stretch or the like. As will be discussed in greater detail below, one of the principle advantages of these conductive ink patterns is that they may readily allow transfer of the conductive ink pattern onto the fabric (e.g., by silkscreening techniques and/or by heat transfer).

Any of the conducive ink patterns described herein may include a gradient region, as discussed herein. This gradient region is typically between the conductive ink and the adhesive. The gradient region may have a thickness of greater than about 10 µm (or greater than 15 µm, greater than 20 µm, greater than 25 µm, etc. and typically less than 200 µm). Any of these gradient regions may not specify the thickness of the conductive ink pattern. For example, any of the gradient regions between the conductive ink and the adhesive may be expressed as a gradient region comprising a nonhomogeneous mixture of the conductive ink and the adhesive wherein the concentration of conductive ink decreases from a region closer to the layer of conductive ink to the layer of elastic adhesive.

In addition to the conductive particles, binder, solvent and thickener, the composition of the conductive ink may include: primer, adhesive, defoamer, catalyst and/or additives. The conductive materials (e.g., conductive particles) typically ensure the conductivity of the ink. Examples of conductive materials may include carbon black, mica, graphene, and graphite. In particular, the conductive particles may include mica coated with antimony-doped tin dioxide. As mentioned, the conductive particles are typically (on average) between 30-70% of the conductive ink (e.g., between 40-60%). The distribution of the conductive particles in the conductive ink layer may be uniform or non-uniform. In particular, conductive ink particles may migrate during application to the fabric into the adhesive layer (and through any additional layers between the conductive ink and the adhesive), forming the intermediate layer.

The binder or base material in the conductive ink may comprise, e.g., an acrylic water base, a water based polyurethane, etc. The binder/base acts to bind permanently to the substrate (e.g., adhesive, fabric, etc.) all the solid components contained in the ink. In some variations the binder/base is an adhesive (e.g., the adhesive forming the adhesive layer). In some variations a separate adhesive (glue) is used in the conductive ink; for example the adhesive may be an acrylic, polyamide, etc. The adhesive may help ensure the transfer of the conductive product to the fabric. The conductive ink may be about 30-50% binder (wet and/or dry).

The conductive ink may also include one or more primers. A primer typically increase adhesion and compatibility between the various products applied; consequently increase the resistance to washing processes.

Any of the conductive inks described herein may also include one or more defoamers. For example, a defoamer may eliminate air and foam contained in the ink. Known defoamers may include insoluble oils, polydimethylsiloxanes and other silicones, certain alcohols, stearates and glycols.

Any of these conductive inks may also include a catalyst, to allow/ensure the complete crosslinking of the binder. The catalyst used may depend on the type of binder used.

Additional additives may also be used, typically to increase the printability and the stability of the ink. One or more thickener may be included, to thicken the liquid components contained in the ink so that it may be accurately applied to the substrate and/or fabric.

A wearable electronics device may include: a garment comprising a compression fabric; at least one stretchable and conductive ink pattern on the garment, wherein the conductive ink pattern comprises: a layer of conductive ink having: between about 40-60% conductive particles, between about 30-50% binder; between about 3-7% solvent; and between about 3-7% thickener; a layer of an elastic adhesive on the garment; and a gradient region between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive; and a conductive thread coupled to the compression fabric and electrically connected at one end region to the conductive ink, wherein the conductive thread extends along garment in a sinusoidal or zig-zag pattern. The conductive thread may be stitched onto the compression fabric, and/or glued onto the compression fabric.

As mentioned above, methods of forming any of the apparatuses (e.g., devices and systems, such as garments) described herein may include forming the stretchable conductive ink pattern either directly onto a fabric, or indirectly by forming a transfer and then transferring it. For example, a method of making a wearable electronics garment may include: placing a transfer substrate comprising a stretchable conductive ink pattern against a compression fabric, wherein the conductive ink pattern comprises: a layer of conductive ink having: between about 40-60% conductive particles; a layer of an elastic adhesive; and a gradient region between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive; and transferring the conductive ink pattern from the transfer substrate to the compression fabric.

As mentioned, the layer of conductive ink comprises between about 40-60% conductive particles, between about 30-50% binder; between about 3-7% solvent; and between about 3-7% thickener.

The method may also include peeling the transfer substrate off of the conductive ink pattern. The transfer substrate may comprises a paper or plastic (e.g., polyurethane) substrate. In variations using a conductive thread, the method may also include attaching a conductive thread to the compression fabric, wherein one end of the conductive thread is electrically connected to the conductive ink pattern. The transfer substrate may therefore include a conductive thread in electrical communication with the conductive ink pattern.

Transferring may be heat transferring, e.g., transferring may include applying heat to transfer the conductive ink pattern and/while placing it against the garment (e.g., ironing it on). Transferring may comprise applying heat from about 130° C. to about 300° C. to transfer the conductive ink pattern to the compression fabric. Transferring may include transferring the conductive ink pattern from the transfer substrate to the compression fabric.

Any of these methods may include printing the conductive ink pattern on the transfer substrate before placing on the compression fabric. The compression fabric may be in a relaxed (not stretched, e.g., flat/smooth but not stretched) before and/or during the transfer.

The conductive ink pattern may be printed on the transfer substrate by: printing the conductive ink onto the substrate in a first pattern; printing the adhesive onto the substrate over the first pattern; and forming the gradient region between the conductive ink and the adhesive.

A method of making a wearable electronics garment may include: printing a pattern of conductive ink and an elastic adhesive onto a substrate such that the conductive ink is substantially co-extensive with the adhesive, wherein the conductive ink comprises between about 40% and about 60% of conductive particles; and forming a gradient region between the conductive ink and the adhesive, the gradient region comprising a nonhomogeneous mixture of the conductive ink and the adhesive wherein the concentration of conductive ink in the gradient region decreases from a region closer to the layer of conductive ink to the layer of elastic adhesive. The substrate may comprise a transfer substrate (e.g., paper, plastic, etc.). The surface of the substrate may be 'non-stick' (e.g., waxed, sealed, etc.) or otherwise prepared to enhance the transfer (and removal) of the substrate. The substrate may comprise a compression fabric. As mentioned above, the conductive ink may comprise between about 40-60% conductive particles, between about 30-50% binder; between about 3-7% solvent; and between about 3-7% thickener.

In any of these variations, the pattern of adhesive and/or conductive ink may be screen printed. For example, printing may include placing a screen having openings configured as a first pattern onto the substrate and spreading the adhesive over the screen.

In general, the viscosity of the conductive ink and/or the adhesive may be selected so that it may be printed onto a substrate and/or the fabric. For example, the viscosity of the ink (uncured) may be between about 60 Poise and about 200 Poise, and the viscosity of the uncured adhesive may be similar. Viscosity decrease with temperature; in general the viscosity may be within the indicated range between a temperature of about 15° C. and about 38° C. (working range).

In some variations, printing comprises spraying the adhesive and/or conductive ink onto the compression fabric.

In general, the gradient (intermediate) region between the adhesive and the conductive ink may be formed during the printing process, either actively or passively. For example, forming the gradient region may include printing the conductive ink onto the adhesive while the adhesive is sufficiently fluid to allow diffusion of the conductive ink into an upper region of the adhesive. Diffusion of the ink and/or glue may be enhanced/inhibited by regulating the temperature (e.g., heating or cooling). In some variation a mixture of adhesive and conductive ink may be applied (e.g., mixture of 50/50 adhesive/ink, mixture of 60/40, mixture of 70/30, mixture of 40/60, mixture of 30/70, etc.).

A method of making a wearable electronics garment may include: printing an adhesive onto a compression fabric in a first pattern, wherein the adhesive is elastic when dry; printing a conductive ink onto the first pattern; and forming a gradient region between the conductive ink and the adhesive, the gradient region comprising a nonhomogeneous mixture of the conductive ink and the adhesive wherein the concentration of conductive ink in the gradient region decreases from a region closer to the layer of conductive ink to the layer of elastic adhesive.

In general, printing the conductive ink may include printing between 3 and 20 layers of conductive ink. The conductive ink may be printed so that the conductive ink does not directly contact the compression fabric. The method may also include printing an insulating resin over part of the conductive ink.

In any of the devices and methods described, the adhesive ("glue") may be a thermo-adhesive water-based glue that is electrically insulative and mechanically stretchable. For example, commercially available fabric adhesives that are water-based and electrically insulative may be used.

As mentioned above, printing the adhesive may comprises placing a screen having openings configured as the first pattern onto the compression fabric and spreading the adhesive over the screen. Similarly, printing the conductive ink may comprise placing a screen having openings matching at least a portion of the first pattern onto the compression fabric and spreading the conductive ink. As mentioned, printing the conductive ink may comprise printing a conductive ink having: between about 40-60% conductive particles, between about 30-50% binder; between about 3-7% solvent; and between about 3-7% thickener.

In general, printing the adhesive onto a compression fabric may comprise spraying the adhesive onto the compression fabric; printing the conductive ink may include spraying the conductive ink onto the first pattern. As also described above, forming the gradient region may include printing the conductive ink onto the adhesive while the adhesive is sufficiently fluid to allow diffusion of the conductive ink into an upper region of the adhesive.

BRIEF DESCRIPTION OF THE DRAWINGS

FIGS. 6A-6E show embodiments of wearable communications platforms useful for sensing and various types of communication, including physical communication and feedback.

FIG. 7 shows a collar for use with a wearable communications platform useful for providing communication.

FIGS. 8A-8C show an embodiment of a wearable communications platform for sending heart rate and for communicating. FIGS. 8A-8B show front and back views of a shirt configured as a sartorial communications apparatus including a body sensor configured as a heart rate sensor. FIG. 8C shows an embodiment of a body sensor configured as a heart rate sensor.

FIGS. 9A-9B show an embodiment of a wearable communications platform for detecting a user's respiration and for communicating.

FIGS. 10A-10B show embodiments of conductive media based systems useful for conducting power and data in a wearable communications platform.

FIG. 10C is another variation of a conductive ink pattern, including an adhesive, gradient region, and conductive ink, as described herein.

FIGS. 15A-15D show different views of a wearable communication device.

FIG. 20A is a front view of a garment (showing both a shirt and pants) for measuring an ECG.

FIG. 20B is a back view of the garment (shirt and pants) of FIG. 20A.

FIG. 21A is a front view of another variation of a garment for measuring ECG in which the limb leads are positioned on the shirt, e.g., not requiring leg leads. For example, when exercise stress tests are performed, limb leads are often placed on the trunk to avoid artifacts while ambulatory (arm leads moved subclavicularly, and leg leads medial to and above the iliac crest). FIG. 21B is a back view of the garment of FIG. 21A.

FIGS. 21C and 21D show front and back views, respectively, of a garment configured to detect ECGs.

FIG. 29A-29D are micrographs illustrating the distribution of chemical components (e.g., carbon in FIG. 29A, sulfur in FIG. 29B, silicon in FIG. 29C and oxygen in FIG. 29D) of a stretchable conductive ink composite (pattern). Large arrows on each micrograph indicate the visual display of chemical composition.

FIG. 31A shows different patterns of stitches, having different pitches and widths (angles); FIG. 31B shows an example of five parallel conductive threads that may connect to five different sensors. FIG. 31C shows an example of a single conductive thread.

DETAILED DESCRIPTION

Figure 1A:
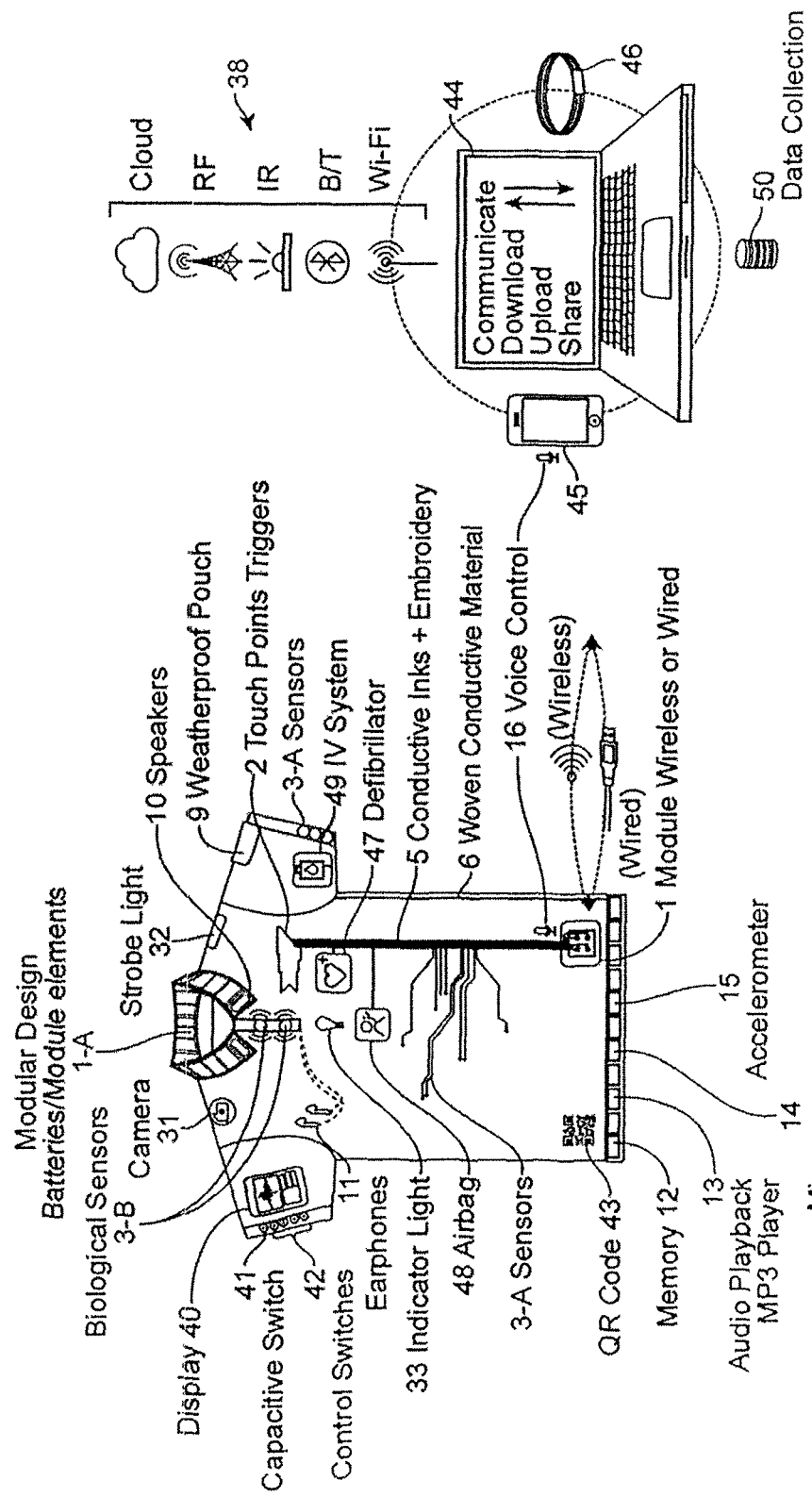
FIGS. 1A-1B show one variation of a wearable communications platform including front and back views of a shirt forming the sartorial communications apparatus.

Described herein are wearable electronic devices formed on a fabric (including compression garment fabrics) using a stretchable and conductive ink pattern. The stretchable ink patterns may be referred to herein as conductive ink composites, conductive ink structures and and/or conductive ink traces, electrodes or sensors. As used herein, a conductive ink pattern typically include a layer of an elastic adhesive, a layer of conductive ink (e.g., typically having between about 40-60% conductive particles, between about 30-50% binder; between about 3-7% solvent; and between about 3-7% thickener) and a gradient region between the adhesive and conductive ink layers. The combination of these three layers provides a stretchability (while remaining conductive and unbroken) that is typically greater than the conductive ink alone.

The apparatuses described herein, include devices and systems, such as the garments containing wearable electronics. In general, these garments may be compression garments, however, they may also be formed as garments that are not compression garments. These garments may be referred to as wearable communications platforms and/or sartorial communications apparatuses. Such devices may provide accurate and multi-faceted communication that improves an individual's sense of themselves and their interactions with the world around them. Such a wearable communication platform may be configured to detect and respond to signals from the user (e.g. from a wearable electronics based garment platform) and may communicate with the user and others and may perform other useful functions. Such a platform may measure and magnify our performance, monitor our health, expand our communication capabilities, enhance our social connectivity, entertain us and more. Wearing such electronics, sensors and communication devices/tools allows communication in a distinctive new way. For example, such a communication platform may be able to accurately detect, process, compare, transfer and communicate in real time physiological signals of the wearer (such as a person, an animal, a plant, etc.).

Such a communication platform may provide more freedom to an individual and may be considered to represent a new wave of intelligent, personal communication, after the first two "waves" which may include computers (first wave) and mobile telecommunications devices (second wave).

A wearable communications platform, as described herein, may provide the following advantages. It may be usable during any normal daily life, including spontaneous activities. It may redefine the meaning of accurate evaluations of the current physiological status of an individual (or nature or other things). It is generally known that a process of measuring—in which an individual knows he is being measured—may affect the parameter being measured and therefore cause a measurement to be less accurate. The process of measuring may generally cause constraints that limit an individual's freedom of movement due to limitations in the measuring devices themselves (e.g., cumbersome machines, hanging wires, spending time gluing or attaching sensors) or the conditions in which the measurements are taken (e.g., a laboratory, or a hospital or a medical facilities habituated by sick people that may generate stress, fear or apprehension in the individual being measured). A wearable communication platform may be accurate not only in terms of the correspondence of the measurement to the real value, but also in terms of correspondence of the detected physiological condition of the individual who is no longer affected by the taking of measurement. Using a wearable communication platform, accuracy of measurement may be directly related to the increased degree of freedom available while taking the measurements. Wearing such electronics, sensors and communication devices/tools allows communication in a distinctive new way. An advantage of the wearable communication platform described herein may be that it improves the way people communicate and live by a) providing accurate information from which they can optimize the way they live; b) providing instantaneous feed-back so that a user can improve while 'in action'; c) by communicating directly to the body and by bypassing mistaken interpretations of the mind (e.g. computers and mobile devices communicate to the mind). A wearable communication platform as described herein may enhance the learning process and the exactitude of what is learned. A wearable communication platform may not communicate just to the ears (through voice, sounds, music) and the eyes (images, photos, videos) of the receivers but may also communicate directly to their bodies (to their muscles, to their points of stress, to their sensitive points, etc.), for example, to improve movements in daily activities or sports, to correct postures and alignments, breathing, etc. and may optimize physical and mental efficiency (e.g. through haptic activators and sensors). An individual may better understands his emotions and feelings by attentively observing their manifestations in their bodies rather than by listening to an emotional mind that is unduly influence by doubt, fear, aversion, clinging, social pressure, media brain washing, etc. By listening to the body, an individual listens to the truth. A wearable communication platform as described herein may provide a real time (e.g. instantaneous) body part specific feedback so that a user can optimize their efficiency while in action and keep improving. A wearable communication platform may allow an individual to communicate and share messages, feelings, moods, actions, etc. through interactive sensors ('touch points'). A 'touch points' may be a more immediate, more natural and faster communication and sharing means then are computer typing or mobile dialing or texting. An enhanced accuracy, a capacity to communicate directly to an individual's body rather than just through the mind, the fact that a user may have instantaneous feedback may provide a wearable communication platform as described herein with a fundamental quality that further distinguishes it from the previous two platforms of communications: computers and mobiles communicate interpretations of the reality related by journalists, bloggers, users communicating what they personally believe is reality. A wearable communication platform as described herein communicates objective, free, scientifically quantifiable physiological data about people, nature and things. An enhanced accuracy of the wearable communication platform described herein may provide a substantial advantage to patients, athletes and others to maintain an active lifestyle, and improve their health, their performances and their efficiency. It may allow people at large to change the way they express themselves by enhancing and liberating their creativity: the platform may include algorithms that may help a user transform their movements into music, their physiological signals into melodies, messages, perfumes, colors, and may allow them to dance or execute exercises in coordination, generated instant events, etc. A wearable communication platform may automatically provide an accurate "dairy" of a user's life without them having to write or take notes. A wearable communications platform as described herein may connect friends, athletes or people with similar interests, activities or diseases and enhance their social bonds with more intimate communication and may help them organize events, have virtual competitions or share their most private information.

The wearable communications platforms described herein may also be referred to as intelligent platforms (intelligent garment platforms, intelligent wear, intelligent apparel, intelligent apparel platforms, intelligent module, smart wear, etc.) or, interchangeably, as "sartorial communications apparatuses".

A wearable communications platform may integrate apparel, a power control system(s), electronics, software, etc. to allow, for example, for on-demand access to new media down-loadable content, up-loadable content and/or instructions, sharing technology, and facilitating location based interaction and specific associated content for each location. An intelligent garment platform may be created with printed and physical sensors, conductive and elastic materials and media (inks), electronics, software, and advanced fabrics create and may measure, evaluate and improve a user's life. An intelligent garment platform may allow for the ongoing development of functional applications that can be added to the platform, such as on a digital download basis and/or a modular electronic basis. There is a long-felt need to create an integrated solution for an intelligent, lightweight, comfortable, and intelligent apparel platform and accessories.

One aspect of the invention comprises a wearable flexible garment platform for communicating a wearer's condition comprising: a wearable flexible garment comprising: a body sensor on the garment configured to sense one of a wearer's position, a wearer's movement, and a wearer's physiological status and thereby generate a body sensor signal; a conductive trace on the garment, connected with the sensor and configured to communicate the body sensor signal from the sensor to a sensor module for analysis; an interactive sensor on the garment configured to transmit an interactive sensor signal to the sensor module when the wearer's hand activates the interactive sensor wherein the sensor module is configured to control an audio output and/or a visual output in response to the interactive sensor signal; a pocket on the garment configured to contain the sensor module; and a sensor module for receiving the body sensor signal from the body sensor, processing the signal to generate an output signal, and outputting the output signal to thereby provide a feedback output. In some embodiments a pocket on the garment may be configured to removably contain the sensor module.

Figure 1B:
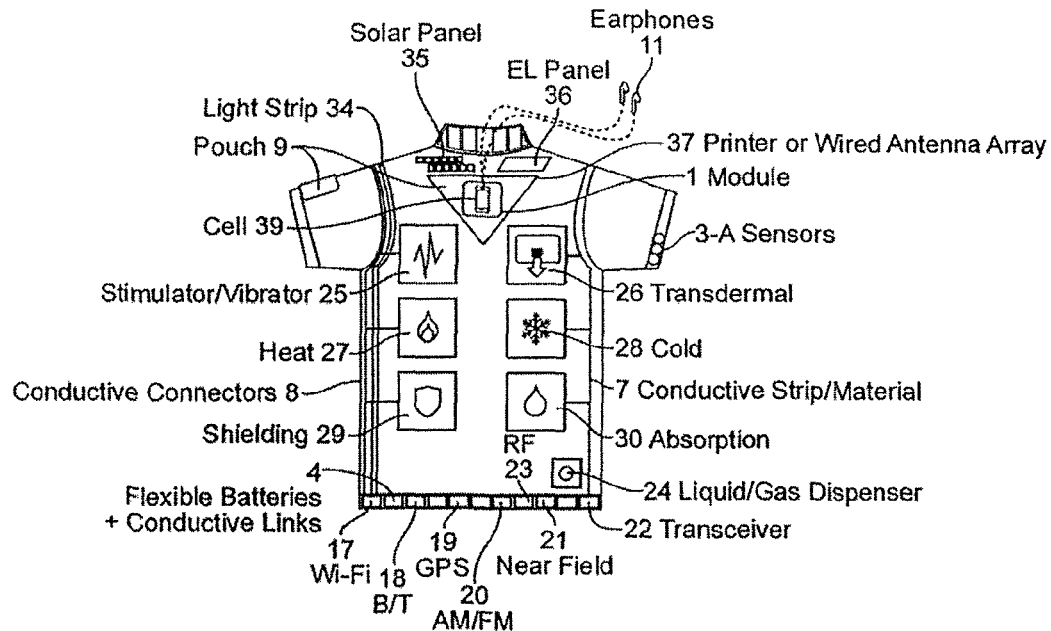

FIGS. 1A-B shows an overview of one variation of an intelligent wear platform. FIGS. 1A-1B show embodiments of a flexible garment in the form of front elevation views of a shirt to be worn on the wearer's torso. FIG. 1A shows a front view of an intelligent wear shirt system. FIGS. 1A-B show an intelligent wear module, which may be a core of an intelligent system that powers and controls all (or many) other elements, both printed and physical, in the apparel. Additionally, a smart module may facilitate some, most or all communications with a user's smart phone, computer, or other networking device (e.g. internet access device) or allow for the embedded capabilities of these functions within the garment. A module 1 can work alone as a self-contained powered unit, or may work in conjunction with additional modular elements. A smart module could work in conjunction with a battery such as an additional flexible battery and/or modular battery. Such a battery may be designed to be added to the intelligent wear in a hem, a seam(s), or (another) non-conspicuous location(s) on the apparel.

In general, the elements on the garments described herein may be formed or connected by one or more conductive ink pattern. In particular, a conductive ink pattern may be used as a sensor, described in greater detail below, and/or an electrode, and/or a connector (e.g., trace) electrically linking one or more devices.

As exhibited in reference numerals 12-15 and 17-23, an intelligent and flexible conductive belt can be, for example, be added to or embedded in an item of intelligent apparel. An intelligent and flexible belt can contain elements that include, but are not limited to, elements to further enhance module 1, including an additional memory, battery power, a microprocessor, an accelerometer, and/or Wi-Fi capability, Bluetooth capability, GPS, a transmitter, AM/FM capability, and a transceiver.

A rear surface image of the apparel, as shown in FIG. 1B, demonstrates reference numerals 24-30 that may offer a variety of user comfort functionality that can be utilized together or separately (individually), to supply the intelligent wear user electrical stimulation, vibration, heat, cold, shielding, absorption, etc. When a temperatures sensor senses a temperature drop below or above a particular (e.g. preset or chosen) level, a system sensor can (e.g. automatically) trigger a printed heat panel(s) or a cold panel(s) to activate, and they can be further controlled by the intelligent wear user via a thermostat, a direct temperature control, or via a variety of program options.

A front surface image of an intelligent-apparel garment demonstrates a camera 31 in the apparel, such as a still image camera and/or a video camera and/or another camera. The camera can be controlled by the user or can be controlled via remote control from another source that the intelligent wear user allows to control the camera, such as via a module communication system, via the internet, via a Wi-Fi connection, or via a Bluetooth connection(s).

FIGS. 1A-1B also demonstrate examples of different types of lighting effects that may be available on an intelligent apparel, such as a strobe light 32 that can also or instead remain on as a solid light, an indicator light 33, and/or a lighting strip(s) 34. Any lighting effect may be placed on or incorporated into a garment. Each of the lights may be controllable such as via a set-and-forget program(s), may be triggered on and off, may be set to respond to different sensor inputs such as time, daylight, absorb ambient light, and may be configured to radiate, glow, etc. Any or all lights may be controllable via a smart module 1, and/or may be powered via the smart module 1 and/or may be powered via a flexible battery 4.

A panel, as indicated in FIGS. 1A-1B, can create and/or store power, and/or may be powered by a (or more than one) solar panel 35.

An electroluminescent panel 36 (an EL panel) may be powered in any way, such as, for example, by a solar panel 35, from a flexible battery 4, or from a rechargeable battery (which may be located in the smart module 1). Such a panel may respond to a pre-programmed sensor, a transmitter, etc. Each panel can work alone or can work in conjunction with another feature(s).

FIGS. 1A-1B demonstrate a possible placement for an antenna array 37 that can work, for example, in both of (or in either of) a transmission mode and a receiving mode, and may extend the range of another sensor(s) and/or communication forms. In this case, the array may also act as a design element within a pouch 9 (such as in a created back panel shown in FIG. 1B) or for the pouch 9 (such as on the weatherproof pouch shown in the front view of FIG. 1A). Networking technology 38 can work alone or in conjunction with antenna array 37 for range extension. Additionally, the intelligent user can work in conjunction with a networking device 45 (e.g., such as, a computer, a smart phone (their own smart phone), a tablet) or another cell phone 39 to program, change, modify, or facilitate voice activation commands to control module 1.

A display 40 can provide the intelligent wear user a visual and audible device to see feedback, sent data, responses, etc. from any or all the sensors, electronics, inputs, etc. available to the intelligent wear user, such as alone, or in conjunction with the intelligent wear user's cell phone 39 and/or networking device 45, such as computer, smart phone or tablet.

An entire intelligent wear system can work alone or in conjunction with one or more of an enhancement accessory 46, such as, for example, a wristband or watch. An intelligent accessory (or accessories) can add an additional functionality to the intelligent system, and can be triggered to respond to a programmed element(s).

Smart module 1, shown in perspective view, may be wired or wireless, and may contain the main processing core of an intelligent system that facilitates some, most or all sensors, communication links (Bluetooth, cellphone, internet, Wi-Fi, etc.), control, and power distribution. Smart module 1 can be a self-contained unit, and or, be supported by modular connection elements with enhanced functionality. A module may be woven into, printed upon, attached to, or otherwise be in proximity with the apparel. A module can be used as a "hot spot" allowing for multiple internet or communication tethering access functionality.

FIG. 1A also shows a front view of an interactive sensor 2 (such as a conductive touch point) that can activate a routine in the smart module 1 such as via touch, proximity, voice activation, or via a variety of programmable or pre-programmed instructions. An interactive sensor (a touch point) can be located anywhere on the apparel. An interactive sensor (touch point) can, for example, be in a designated area, and may be printed or affixed on the apparel. An interactive sensor can be virtual in that a location may be projected or fixed on the apparel such as in the form of a projection or augmented reality format (for example via a camera or projector), and an interactive sensor may be, for example, triggered by proximity, touch, or voice. Such an interactive sensor may act as a user interface on a shirt (or other intelligent wear accessory, garment or item). Such an interactive sensor may be customizable for different uses (such as based on user preference). Different modes of activation of a single sensor (e.g. a single tap, a double tap; etc.) may lead to different actions. In some embodiments, an interactive sensor may be configured to transmit a first interactive sensor signal when the user's hand activates the interactive sensor once and to transmit a second interactive sensor signal when the user's hand activates the interactive sensor twice in succession wherein the first interactive sensor signal is different from the second interactive sensor signal. A plurality of interactive sensors may be present. Such sensors may all be activated by the same type of trigger (e.g. a single tap) but each may control a different action or activity (for example, one sensor may control a phone, another sensor may control messaging) such as through different interactive sensor signals. In some embodiments, the first interactive sensor is configured to send a first interactive sensor signal and the second interactive sensor is configured to send a second interactive sensor signal which signal is different from the first interactive sensor signal. Two (or more than two) sensors may be activated by the same type of trigger (e.g. a single tap) and may control the same action (for example, a sensor on a hem of a shirt and a sensor on a collar may both be configured to control music volume). Different modes of activation of a single sensor may result in different interactive sensor signals and different types of action (e.g., a single tap controls music volume and a double tap controls messaging). Using an interactive sensor(s), a user may control any element that is connected with it, including controlling any other elements on a connected intelligent garment item and/or any items connected wirelessly with it. For example, an interactive sensor may control a call (activate a call, answer a call, end a call, etc.), control music (bass, musical selection, volume, etc.), control a microphone, deliver a message, share content, perform a social check-in such as via a location based service, etc. For social sharing, a user may choose a delivery method (for example, a proprietary intelligent wear web platform, a call, an email, a Facebook connection, a short message service (SMS), Twitter, etc.). An interactive sensor (s) may allow a contact to be chosen from any library such as via an intelligent wear application, and control (open) a communication with a simple interaction with an interactive sensor (such as with a single tap, a double tap, a triple tap, a press and hold, a voice command, etc.). For example, by tapping on a touch point a climber can share his location and altitude with his intelligent wear application friends or Facebook friends. In another example, through a press and hold on a designated touch point on a shirt, a user can activate an emergency call (e.g. to 911) and immediately get help if in danger.

FIGS. 1A and 1B show a variety of different sensor applications 3A on, in, and around the intelligent apparel that may include, but are not limited to one or more sensors configured to measure respiration, heart rate, pulse, pressure, moisture, humidity, elongation, stress, glucose and/or pH, wear, resistance, DNA, nerves or nerve activity, muscle activity, bone stimulation, optics, chemical, motion, thermometer, sleep state, impact, proximity, flexibility, rotation, and/or any other (diagnostic) element. A piece of apparel may have none, one, or many sensors working separately or in unison. A sensor(s) in conjunction with a software application can be programmed to be both passive in data collection mode, and active; for example, in that a sensor data response may trigger a specific response such as data transmission, light activation cameras, stimulators, vibrators, defibrillators, transdermal activations, etc.

FIGS. 1A and 1B show a variety sensors 3B, such as biological sensors, that can be either passive and/or active, such as that they may collect, analyze, transmit and/or respond to a specific biological detection, and/or can trigger one or more of any apparel capability responses.

A flexible battery 4 (or batteries) and (an associated) conductive link may make for a primary power source or incremental power in support of a modular power system may be flexible, light weight, expandable, quick connecting, comfortable, shapeable, and/or otherwise consumer friendly. Power may be wired or wireless and may be fixed or may be rechargeable.

A printed conductive material 5 may, for example, include an ink (media), a dye for a thread and/or embroidery, a printed material that may be used to distribute power and communication requirements to all aspects of, and between, sensors, arrays, components, lights, electronics, panels, printed and wired elements in the intelligent wear, both internally and in conjunction with an added accessory.

A woven conductive material 6 may be used alone or in conjunction with a printed conductive material to be able to design the power points and distribution requirements in and around the apparel to create, for example, the most efficient look and/or consumer friendly design, while keeping a garment light, washable, and wearable without the need for heavy wired elements. A woven conductive may allow for placement or affixing of multiple elements onto the apparel.

A conductive strip material 7 and a conductive connector point 8 may allow for the attachment of modules, sensors, and electronic elements anywhere along a line of a conductive trace on the intelligent garment.

A weatherproof and/or waterproof pouch or pocket 9 may allow for the addition of a sensitive electronic or sensor elements and/or storage. A pockets or pouch may be situated in, on, and/or around any portion of the internal surface or external surface of an intelligent wear product.

In some embodiments of a wearable garment system, wherein the flexible garment comprises a plurality of body sensors for generating a plurality of body sensor signals, and the body sensors are connected with a plurality of conductive traces wherein the sensor module is configured to receive the plurality of signals from the plurality of conductive traces and process the signals to generate a feedback output wherein the feedback output comprises one of an audio output, a visual output, and a tactile output. In some embodiments of a wearable garment system, the wearable garment system further comprises one of a speaker and an earphone connected with the sensor module wherein the audio output comprises a music output configured to be sent to the earphone or speaker.

A speaker 10 may be embedded in, printed on, or attached to the apparel in any area, including but are not limited to a collar section of the intelligent wear, inside a back collar, or inside a collar. A speaker may provide for different sound effects. A speaker may include a base unit or a stimulator or a vibrator. A speaker may have, but is not limited to, the form of a printed, a physical, or a wireless speaker attached to the garment, etc.

An auditory receiver 11 (such as an earphone or an earbud) may be attached to the intelligent wear garment. Such forms include, but are not limited to, fixed, retractable, printed, or physical wire elements, with or without a housing.

A fixed or removable section of a modular element may work alone or together with a modular connection point such as added memory 12 or other content storage capacity.

A fixed or removable section of a modular element may work alone or together with a modular connection point such as an audio and/or video playback device 13 (e.g., an MP3 player or a video player). A piece of apparel may have such a device designed into it or affixed to it, or such a device may be in proximity to the apparel. Such a modular element may work alone, or may work in conjunction with another modular element, and may be of a plug-and-play design, with ease of use for connection and detachment, and may reside in the apparel, hems, etc.

In some embodiments of a wearable garment system, an output signal is configured to be sent away from the wearable garment, such as to another individual, to a computer, or to a website.

A fixed or removable section of a modular element may work alone or together with a modular connection point such as a microprocessor 14.

A fixed or removable section of a modular element may work alone or together with a modular connection point, such as an accelerometer 15.

An intelligent wear garment or system may be controllable using a voice control 16, including but not limited to commands either alone, or in conjunction with other buttons, switches, cell phones, computers, and internet systems.

A fixed or a removable section of a modular element may work alone or together with a modular connection point to facilitate the use of a Wi-Fi 17 or enable a Wi-Fi connection with another internal or an external element.

A fixed or removable section of modular element may work alone or together with a modular connection point to facilitate the use of Bluetooth 18 or enable a Bluetooth connection with another internal or external element.

A fixed or a removable section of a modular element may work alone or together with a modular connection points to facilitate the use of GPS 19 or enable a GPS connections with another internal or external element.

Either a fixed or a removable section of a modular element 20 may work alone or together with a modular connection points to facilitate the use of AM/FM/radio waves/frequencies 20 or enable a radio connection with another internal or external element.

Either a fixed or a removable section of a modular element may work alone or together with modular connection points to facilitate the use of near field technologies 21 or enable near field with another internal or external element.

Either a fixed or a removable section of a modular elements may work alone or together with a modular connection points to facilitate the use of a transceiver 22, a transmitter and/or receiver or to enable transmission or receiver connections with another internal or external element for an item, such as, for example a cell phone signals, a radio frequencies, a power waves, a diagnostic, etc.

Either a fixed or a removable section of a modular element may work alone or together with a modular connection point to facilitate the use of radiofrequency 23 or enable radiofrequency use with another internal or external element.

A dispenser unit 24 may be configured to dispense a gas and/or a liquid, such as in response to a programmed element or sensor stimulus, manual and automatic response scenarios.

In some embodiments of a wearable garment system, the wearable flexible garment further comprises a haptic actuator configured to provide a tactile sensation to the wearer based on the output signal.

In some embodiments, a garment may include a stimulator/vibrator 25 capability that may be activated, such as by a transcutaneous electrical nerve stimulator (TENS) electrical stimulator, that responds to a preprogrammed element or a bone stimulator for direct placement on a specific location on the body. An activation signal can, for example, be triggered from a sensor to send a pulse, vibration, or electrical stimulus in response to data to wake somebody up, prevent sleep such as in the case of a transportation environment such as aerospace or automotive environments to prevent accidents.

In some embodiments, a garment may include a transdermal delivery function 26. Such a delivery system may be triggered by a variety of inputs that include, but are not limited to voice activation, to sensor data, timing devices, communication, location, etc.

In some embodiments, a garment may include on-demand heating and treatment capability 27 that may be able to a respond to a preprogrammed element, voice activation, sensors, thermostat, and may be directly placed on a specific location on the body or all around the intelligent wear.

In some embodiments, a garment may include demand cooling and treatment 28 capability that may be a used in response to preprogrammed elements, voice activation, sensors, thermostat, and may be directly placed specific location on the body or all around the intelligent wear.

In some embodiments, a garment may include shielding capability 29 that may be configured to respond to a preprogrammed element, voice activation, sensors, thermostat, and may be directly placed on a specific location on the body or all around the intelligent wear.

In some embodiments, a garment may include an absorption capability 30 that may be configured to respond to a preprogrammed elements, voice activation, sensors, thermostat, and may be directly placed on a specific location on the body or all around the intelligent wear.

In some embodiments, a garment may include a camera/video recorder 31 and projector capability that may be configured to respond to a preprogrammed element, voice activation, sensors, thermostat, remote input, and for direct placement on a specific location on the body or all around the intelligent wear. There may be multiple cameras or projectors that may allow for the capture of multidimensional images such as 3-D, or the projection of images such as holographic, or infrared (IR), or radiofrequency (RF) or other images in variety of both visible with the naked eye, or in conjunction with glasses or other accessories that render the images visible.

In some embodiments, a garment may include strobe light capability 32 that may be a response to a preprogrammed element, voice activation, sensors, light meters, component identification, recognition software, GPS, and for direct placement on a specific location on the body or all around the intelligent wear.

In some embodiments, a garment may include light indicator capability 33 that may be a responds to include but not limited to input, output, stimulus, preprogrammed elements, voice activation, sensors, thermostat, and for direct placement on a specific location on the body or all around the intelligent wear.

In some embodiments, a garment may include light strip capability 34 that can made up of, but not limited to, phosphorescence inks, luminescence, power, bulb, etc. such as in specified areas that may configured to respond including but not limited to input, output, stimulus, preprogrammed elements, voice activation, sensors, time, and for direct placement on a specific location on the body or all around the intelligent wear.

In some embodiments, a garment may include a solar panel recharging/powering capability 35 for primary or supplemental power supply that be may configured to respond to include but not limited to input, output, stimulus, preprogrammed elements, voice activation, sensors, power levels, and for direct placement on a specific location on the body or all around the intelligent wear.

In some embodiments, a garment may include electroluminescence panels 36 that may be configured to respond to include but not limited to input, output, stimulus, preprogrammed elements, voice activation, sensors, thermostat, and for direct placement on a specific location on the body or all around the intelligent wear.

In some embodiments, a garment may include printed or wired antenna array 37 that may be configured to respond to including but not limited to input, output, stimulus, preprogrammed elements, voice activation, sensors, and for direct placement on a specific location on the body or all around the intelligent wear.

In some embodiments, a garment may include Wi-Fi capability and or indicator capability 38 that may be configured to respond to include but not limited to input, output, stimulus, preprogrammed elements, voice activation, sensors, and for direct placement on a specific location on the body or all around the intelligent wear.

In some embodiments, a garment may include cell phone type of communication device 39, allowing for the incorporation of a removable existing phone onto the garment and incorporation with the intelligent wear, or the inclusion of cell communication functionality hardwired into the garment.

In some embodiments, a garment may include a text, still image, and video display capability 40 that can work alone or in conjunction with all the sensors, electronics, or elements inherent in the intelligent wear. A display may work with all the communication, data, sensors, and programs or with a subset of the communication, data, sensors, and program. For example, an audio message can be converted to text and displayed, images from the cameras or projectors can be viewed, functional buttons can be incorporated, etc. users can upload or transfer images from internal intelligent ware shirt to the screen, or accept transfers from 3'd parties, or from software programs, add overlays or special effects, and project the image on the display.

In some embodiments, a garment may include capacitive switch capability 41, and other switching technologies that can trigger any or all activation points on, in, or around the intelligent wear.

In some embodiments, a garment may include a control switch 42 that can be incorporated into, on, around the intelligent wear, or be activated by individual elements added into the apparel.

In some embodiments, a garment may include a QR (quick response) code 43, QR code reader, and other mechanisms to convey data either on or within the apparel, or trigger additional interaction with the intelligent wear system, or drive data communication with a URL or a user's mobile communication device.

In some embodiments, a garment may include user known or hereafter devised smart phone 45, tablet, or such other device that may be necessary or useful to interface the intelligent wear with a user's data, information, or communication network.

In some embodiments, a garment may include a wristband/watch 46 or other accessories that may be developed to bring additional functional capabilities to the intelligent wear system to allow, for example a user to control an aspect of the intelligent wear system (e.g. any of those described herein as being part of the intelligent wear system) using a control function on the watch or wristband or to provide an audio display, a visual display, or a tactile sensation.

An intelligent apparel item may have any or all of the weather protection functionally of traditional clothing (such as being sun protective, water resistant, water proof, wind resistant, wind proof etc.). Intelligent apparel may also or instead have an optional transdermal delivery system. Additionally, the apparel may be infused with such items as vitamins, minerals, electrolytes, and any and all forms of medications, topical solutions, and may perform as transdermal delivery systems. In conjunction with the electronics and sensors, for example, the transdermal delivery system might not only deliver medications and like items, but the intelligent apparel may monitor the intelligent wear user before, during, and after delivery to insure proper dosage, and to monitor one or more vital signs and/or specific medical or safety criteria Intelligent apparel may also include a power and data collection and distribution system for the apparel. The system may supply the required power to operate one to a multitude of electronics and sensors and their associated accessories and/or to power the data communications. The apparel may house the electronics, sensors, and accessories in a user friendly, comfortable, and stylish design. Such power and data may be controlled by intuitive programming.

An intelligent apparel may house or host the smart module or the "brains" of the system. The module may be expandable and adaptable to include new electronics, sensors, and software upgrades, and manage compatibility with industry communications and data collection and distribution standards and security.

Figure 2:
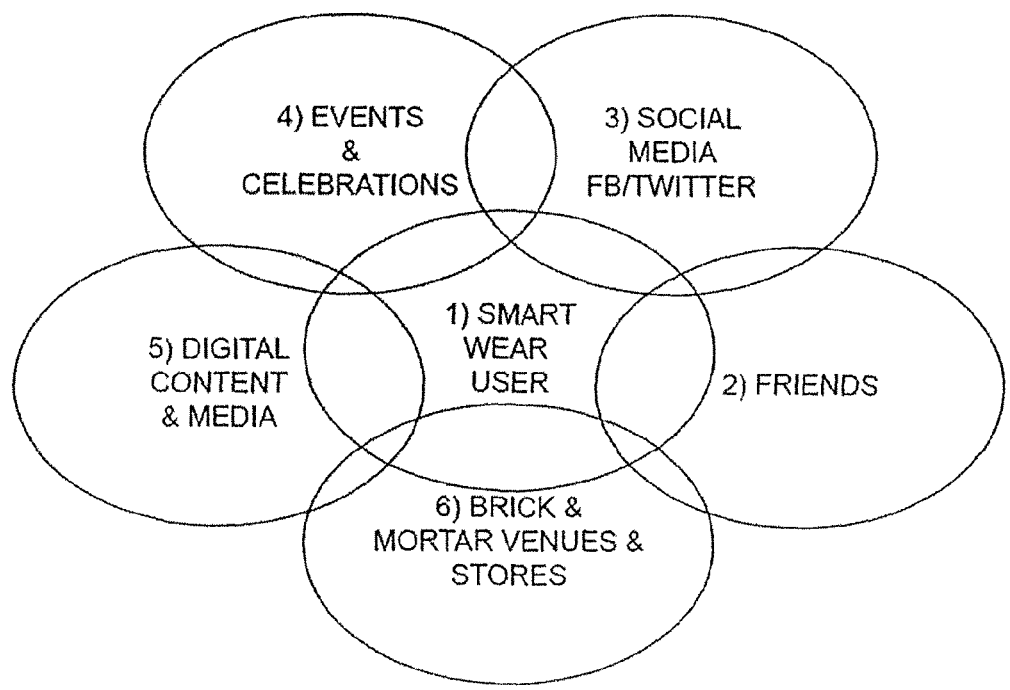
FIG. 2 is a diagram showing how a wearable communications platform can be used for various purposes such as communication.

FIG. 2 shows an embodiment of an intelligent wear system in which an intelligent wear user is #1 or at center of the social hub. With an intelligent wear system, a user may be able to identify and friend(s) user #2 (who is also wearing intelligent garment) the friend's location or proximity to the #1 user demonstrating a proximity and location based technology.

Social media integration: Further, a user (e.g. user #1 or user #2) can also sign into their personal social media site such as Facebook or Twitter, and could share their location with friends, and also allow a follow-me scenario. An intelligent wear user may allow an audio comment response that may automatically be played back via the intelligent wear within a specific location(s), or allow a "tweet(s)" or other responses to appear on an intelligent wear display panel(s).

In some embodiments, a textual social media such as a "tweet(s)" may also be converted to audio and played back via the intelligent wear, or an audio message may be converted to text for playback on a display.

In some embodiments, an intelligent wear user may create a follow-me message(s), and may respond to others who accept such opportunities, and may play back specific responses in either an audio or visual fashion.

In some embodiments, an interactive sensor (touch point) on the intelligent wear can be designated as a "Like" or a "Dislike" functional button, and may allow a third party to register opinions based upon tactile interaction, or vote, or respond to a question(s) in a similar or the same fashion individually or in groups, with the results being shared amongst the participants.

In some embodiments, an intelligent wear user can "check-in" by virtue of entering a location versus needing to actually initiate a check-in process. Doing so can initiate a couponing, advertising, or some other response. A similar reaction may be initiated upon the intelligent user exiting a location.

Location based technology: In some embodiments an intelligent wear user can identify if (that) another intelligent wear user is located within a specific venue or retail location. The user/system may have the ability to leave specific messages or downloadable content for an individual or group of intelligent wear users that have been identified, and such content alerts may be given to the users upon breaching the perimeter of the specified location in the form of audio, visual, or graphical information. An intelligent wear user may initiates the transfer process by sending a "ping" to the other intelligent wear users to initiate an invitation to share content or data (such as sharing a piece of audio content), manage the invitation acceptance/rejection process, encoding and sending that data to the approved recipient.

Additionally, a similar (or the same) concept holds true with regards to allowing the venue or store to leave a discounts and coupons for all or individuals that enter their locations, or as gifts with purchase upon exiting a specific location.

In some embodiments, when an intelligent wear user travels to, enters, or leaves an event that is not a fixed venue location, that user can send location information, data, likes/dislikes on or about the event, and/or even download content that can be played back via the intelligent wear based upon the type of event (e.g. a birthday party, a dance, a festival, etc.) or can send standardized messages representing moods and attitudes to friends who may have or not have an intelligent wear system garment (product).

In some embodiments, another sharing scenario allows an intelligent wear user to tag and leave specific content and messages for other intelligent wear users based upon a location or proximity, and then allow for and manage the acceptance/rejection, downloading, and playback of the approved content.

Another sharing scenario is similar to the scenario described above, but includes the ability to analyze the content and data, and return a response based upon the data result. For example, if an intelligent wear user is running in a race or triathlon, and can receive data or message upon reaching a specific location or way-point.

Intelligent wear location based services (SLBS) functions may include, but are not limited to: location (e.g. of a person, object, friend, business, or event); heading (direction or distance, or turn by turn directions); advertising (location based push or pull); request (nearest service or business); receiving (alerts, sales, warnings, traffic); recovery (assets based); games (where location is part of a game); proximity-based notifications ((push and pull) notification when something available); proximity-based actuation ((such as EZ pass payments, tolls, etc.) or download content); create (point of interest information about location or upcoming event); leave (point of interest information after an event); display (point of interest information on the intelligent wear users phone or intelligent apparel); upload photos with content, events, to be left for others; upload comments that can be displayed with uploaded photos at specific locations/events; zip code search (distance or from center or origin to an event or sale, etc.); permission (user must give opt-in permission by law to share and receive location based service information); geofencing concept (virtual perimeter around a location, and identify when it is being crossed, and push), etc.

Multi-party share and synchronization (venue examples): an intelligent wear user may offer content to one another, synch content with multiple parties with or without an invitation/acceptance concept, and simultaneously play back content on multiple intelligent wear users at the same time. Such a concept may be directed to sporting arenas such as soccer/football, and for music venues and concert halls. Content can be, amongst others, in the form of light programming, display content, graphical elements, and audio. A venues may be, for example: a stadium (connecting fans from the same team, coordinating fans activities through synchronization of speakers (chants, formation, player's name, booing referee), through vibration codes (1=waves, 2=chant, etc.) which may be specific to sport's cultural behavior, through intelligent synchronization of LEDs on fans' T-shirts to display stadium messages (ex. "Goooaaalll!") or images (flag), mapping the fans and using them as 'human pixels' in 'bleaches screens'.); concerts (coordinating fans through synchronization of speakers in a sole chorus, through synchronization of LEDs on shirts to celebrate a song/artist enhancing an existing behavior (turning on lighters); through intelligent synchronization of LEDs on fans' T-shirts to display a song titles or messages; connecting friends and detecting positioning, allowing easy communication); mass celebrations (coordinating masses to spread a unique social message in a sole voice; intelligent synchronization of speakers and LEDs to coordinate/display messages, wave audio and/or lighting effects); couple celebrations (intelligent wear salute (e.g. Valentine's day), 'override', synchronization of love songs); street or car encounters (intelligent wear users may be alerted when friends or intelligent wear system users are nearby, allowing easy exchange of messages or content); "Salute" (intelligent wear speaks or sings to a given person (friend, loved one, team fans, annoying one, wearing another intelligent wear product ("Hi George", "I Love", "We are the best", "loser"). Customers can share or choose official salutes and adapt them to occasions, moods.); "Override" (override a negative expression/conversation or foul/inappropriate language with a loving one by detecting the bad expression through profanity filters and voice recognition and programming the intelligent wear to respond appropriately.); etc.

Unknown intelligent wear users can share controllable "personal" data with others whom they pass or come into proximity to, including making or initiating a new "friend" connection.

Camera sharing functionality: With an additional enhanced feature such as the camera, facial recognition can identify other friends, locations, etc. and signal their appearance, or initiate an audio or visual response. Additional intelligent wear effects include the creation of a camouflage concept by having an image from the camera behind you displayed in front of an individual, creating the illusion that the individual is invisible. Alternatively, still images or moving images from the camera can be captured and played back on the intelligent wear display, shared with others, amended, and processed through a special effects generator creating everything from simple overlays to extensive graphical editing tools, and shared. With the intelligent wear Wi-Fi capabilities, others can simply send images to the intelligent wear shirt for display.

Through a camera (e.g. on a T-shirt), a user may share his view and/or location and post it (also, users may visualize and modify it on Instagram). With a video camera (e.g. on a T-shirt), a user may record his view while walking or doing sport activities (e.g. skateboarding, climbing, running, etc.) and (instantly) post a videos, such as on You-Tube channel through a hotspot on T-shirt: a 'subscribe' channel hotspot on T-shirt.

A camera auto may grab a QR code and/or other response technology and play back an audio response based upon program requirements. A QR code may be used to initiate shopping or product purchasing sequence.

Medical and safety concepts: With a basic GPS functionality, an intelligent wear user can, for example, such as in the case of an elderly parent, determine if such a person left a specified location, and can trigger a notification and response system in order to protect that individual.

Crowd-sharing and shopping concepts: An intelligent wear user and/or intelligent wear may facilitate crowd-shopping and crowd -flash-sales such as via an announcement of a specific location based sale of either/or physical intelligent user apparel systems, or the availability of specific downloadable content, or software upgrades or functionality.

Voice and audio command functionality: None, some or all social media and functions may be initiated by a vocal command or via an intelligent wear application.

Intelligent hot spot functionality: Further, an intelligent wear system may facilitate a social media sharing action in any of a number of different scenarios. One such scenario allows an intelligent wear user's apparel to act as an internet hot spot, allowing for multiple people in proximity to him to share his internet/communications connections.

Figure 3:
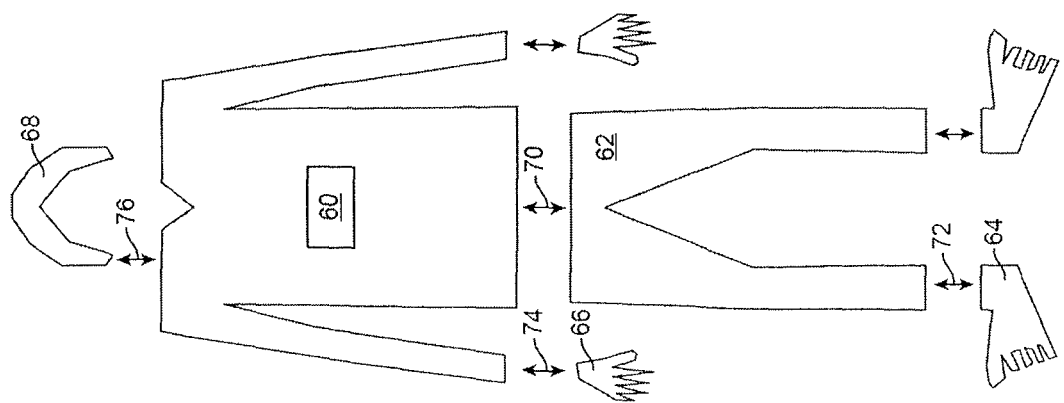
FIG. 3 shows an embodiment of a wearable communications platform with various interconnected apparel items.

In some embodiments, a flexible wearable garment system further comprises a second flexible wearable item (e.g. an accessory or garment) in electrical communication with the first flexible wearable item (e.g. an accessory or garment). Such an electrical connection may be configured to allow power and data to be transmitted. Such garments may be in electrical communication directly such as by a button, snap or another electrical connector or may be indirect communication (such as through a wireless communication). A second garment may be in electrical connection with a third (or fourth, fifth, etc.) flexible wearable garment or accessory. FIG. 3 shows a flexible wearable garment system (an intelligent garment system) with various garments in electrical communication with one another. An intelligent wear shirt 60 is electrically connected via an electrical connector 70 with intelligent wear pants 62. Such a connector may be a substantially rigid connector or may be a substantially flexible connector. Such an electrical connection may be, for example, though a button, a complementary magnetic connection, a snap, a strip (such as a fabric strip), a wire, or any other connection or may be made through a wireless connection. The intelligent wear shirt 60 is also electrically connected via electrical connector 74 with an intelligent wear glove and via electrical connector 76 with an intelligent wear hat 68. Intelligent wear socks 64 are electrically connected via electrical connector 72 with intelligent wear pants 62 which is in turn electrically connected via electrical connector 70 with intelligent wear shirt 60. Each garment or accessory may contain any element as described herein or as known in the art, such as a body sensor, an interactive sensor, a power trace, etc. An interactive sensor (or a body sensor or any other element) may be any color, any texture, or any design.

An intelligent garment item may be a stand-alone intelligent apparel item or it may be an item that works in conjunction with a second item. An intelligent garment may work with a user's other or existing wardrobe item or accessories, for example as an additional layer or as a component attached to another or existing wardrobe item or accessory. A first intelligent garment may have an element that can work with, enhance, and/or support a second intelligent apparel item such as one that houses an intelligent electronic module and activators, (other) electronics, microchips, and/or sensors such as included with an intelligent electronic module.

An intelligent garment item may be any type of clothing or may be any type of accessory and may be used for or configured for a specific purpose. An intelligent garment item may, for example, be a garment or an accessory that houses an intelligent electronic module or may be a garment or an accessory that works with an intelligent electronic module housed in another intelligent garment item. An intelligent garment may be, for example, a top such as a bra, a camisole, a compression shirt, a hoodie, a long-sleeved shirt, an over-shirt, a polo shirt, a shirt, a short-sleeved shirt, a T-shirt, a tank top, a turtleneck shirt, a V-neck shirt, an undershirt, etc.; a bottom such as capris, leggings, pants, shorts, etc.; a hand wear such as, a glove, a mitten, etc.; a headwear such as a balaclavas, a hat, a hood, etc.; a footwear such as, a boot, a foot glove, a shoe, a sock, etc.; or may be a coat, a full body outfit, a jacket, a leotard, a jumpsuit, pajamas, a robe, swimwear, underwear, and/or another specialized worker outfit, etc. An intelligent garment may include any type of accessory (such as an ankle-lace, a bracelet, a flexible screen, a hearing aid, a microphone, a necklace, a speaker, a tie, a watch, etc.) An intelligent garment may be used for any purpose, for example, for athletic wear, fire and safety use, military use, personal protection, patient use, recreation use, etc.

An intelligent garment may have or may allow the incorporation of one or more intelligent wear elements such as one or more body sensors, one or more interactive sensors, a power and data distribution service, a communication control and management system, etc. An intelligent garment may have any or all of the expected weather and environmental protection functionally of traditional clothing. A specific, functional intelligent garment may have a stand-alone design. It may contain printed, woven, wired, and/or wireless nodes, and/or other embedded or attached sensors and/or other associated electronics. It may contain a variety of printed and/or programmable/controllable sensors and activators as defined herein or known in the art or hereafter invented. An intelligent garment may be configured to work in conjunction with another item in an intelligent system in multiple modes, such as a real-time mode, or may be configured to work alone such as when not in a time sensitive mode. It may be managed via a data scheduling algorithm or programming.

An intelligent garment may include one or more than one electronic component or circuit which may include a conductive material. Such a conductive material may be adapted or configured to make a connection (e.g. an electrical connection) between two elements (e.g. devices, garments, items). A connection may be, for example, a conductive material electrical trace (such as a conductive media (conductive ink/conductive ink pattern) or a trace made from a conductive media or conductive ink and described in greater detail below), a conductive silicone, or another type of conductive material that can be deposited on fabric or incorporated into a fabric (e.g. by weaving or sewing or gluing onto/into the fabric). A conductive ink may be "cableless" and may possess greater flexibility than a cable. A conductive material on an intelligent wear garment item may be required to both conduct an electrical signal (including for example, providing sufficient power) and be configured to allow the garment to conform to a user's body. A conductive trace that is non-extendible in a vertical direction may be narrow in a horizontal dimension (i.e. going around an individual). Such a narrow trace that is placed with its long axis in a vertical orientation may allow a garment to substantially expand in a horizontal direction (such as when an individual is stretching a garment and placing it over his head). A plurality of traces (or all traces on a garment) may be oriented in a vertical direction in order to allow a garment to stretch in a horizontal direction. Such a trace may extend from a front of a garment to a back of a garment (such as by traveling over a shoulder area of a garment). In some embodiments, a conductive trace may be extendible in a vertical direction, a horizontal direction, in both a vertical direction and a horizontal direction or in neither direction. A conductive material may be flexible in a vertical direction, a horizontal direction, in both a vertical direction and a horizontal direction or in neither direction. An electronic component may be substantially flexible or may be configured to maintain a shape (e.g. be substantially rigid) when it is in place on a garment. A trace that is non-extendible in a vertical direction may be narrow in a horizontal dimension (i.e. going around an individual). Such a narrow trace may allow a garment to substantially expand in a horizontal direction (such as when an individual is stretching a garment and placing it on his body). A trace that is non-extendible in a vertical direction may be narrow in a horizontal dimension (i.e. going around an individual). Such a narrow trace may allow a garment to substantially expand in a horizontal direction (such as when an individual is stretching a garment and placing it on his body). In some embodiments, a garment may have a maximum extendibility (which may be incorporated into the garment size indication), such as based on the extendibility of a trace or the extendibility of the fabric. In some embodiments, an intelligent wear garment as described herein, does not include (does not have visible) any wires, cables, and/or traces on an outside of the garment.

An intelligent garment may include one or more than one body sensor. A body sensor may be configured, for example, to sense a user's position (e.g. a specific location or position on or of a user's finger, arm, leg, torso, etc.) and a plurality of sensors may be used to sense a plurality of positions or locations (e.g. a specific location or position on or of a user's finger, arm, leg, torso, etc.), a user's movement, a user's physiological status including but not limited to a capacitive strain sensor, a conductive media (conductive ink) capacitive sensor, a conductive media (conductive ink) electrode sensor, a conductive media (conductive ink) resistive sensor, a fiber optic sensor, a metal electrode sensor, an optical sensor such as an optical probe sensor or an optical source sensor (e.g., a laser, a light emitting diode (LED), etc.), a piezoresistive strain gauge sensor, a semiconductor sensor (e.g., a force sensor, a gyroscope, a magneto-resistor sensor, a photodiode sensor, a phototransistor sensor, a pressure sensor, and/or a tri-axis accelerometer). An intelligent garment may include 0, 1, 2, 3, 4, 5, 6, 7, 8, 9, 10-15, 16-20, 21-30, 31-40, 41-50 or more than 50 body sensors.

An intelligent garment may include one or more interactive sensor (touch point). An interactive sensor (touch point) may be made from any material that allows a user to activate it such as by a user's hand or proximity of a user's hand to activate the interactive sensor. An intelligent garment may include 0, 1, 2, 3, 4, 5, 6, 7, 8, 9, 10-15, 16-20, 21-30, 31-40, 41-50 or more than 50 interactive sensors. An interactive sensor may be made from, for example, a conductive silicone, a plate of conductive media (conductive ink), or another type of conductive material. An interactive sensor (touch point) may be deposited on a fabric or may be woven into a fabric or sewn or glued onto/into the fabric.

In some embodiments, an intelligent wear element (e.g. any element on or associated with an intelligent wear item such as a sensor, trace, power supply, etc.) may be flexible and/or conformable. In some embodiments, an intelligent wear element may be substantially rigid or may be configured to maintain a shape. Such an element may have a relatively small footprint so that the intelligent wear garment maintains its flexibility and/or is conformable to a user's body. In some embodiments, a substantially rigid element may be on a portion of a garment configured to contact a relatively inflexible portion of a user's body (e.g. a mid-back, a lower back, an upper back, along a femur, along a tibia, along a foot, along a skull, etc.). For example, an element may be in the back of a shirt and configured to line up with a user's relatively inflexible mid back region). In some embodiments, a substantially rigid element may be on a front of a garment. In some embodiments, the total garment surface area of an element (e.g. as measured by the surface area of the portion of the garment the element covers or) of one or all rigid elements is less than 1 $cm^2$, from 1 $cm^2$ to less than 2 $cm^2$, from 2 $cm^2$ to less than 3 $cm^2$, from 3 $cm^2$ to less than 4 $cm^2$, from 4 $cm^2$ to less than 5 $cm^2$, from 5 $cm^2$ to less than 10 $cm^2$ or from 10 $cm^2$ to less than 20 $cm^2$, on either a garment front or a garment back or both together.

An intelligent apparel item may be provided with motion detection sensors such as accelerometers, gyroscopes and magnetometers to detect the body position and movements and provide immediate feedback.

Another aspect of the invention provides a flexible, compressive shirt configured to continuously conform to a user's body when worn by the user, comprising; a plurality of body sensors on the front of the shirt each configured to sense a user's physiological status and thereby generate a plurality of physiological sensor signals; a plurality of body sensors on each sleeve of the shirt each configured to sense a user's motion and thereby generate a plurality of motion sensor signals; a plurality of elongated conductive traces on the garment each contained in a seam, the traces running from a plurality of body sensors in a substantially vertical direction to a sensor pocket and configured to communicate the sensor signal from the sensor to a sensor module for analysis; and an interactive sensor on the front of the garment configured to transmit an interactive sensor signal to the sensor module when the user's hand activates the sensor with a touch.

Another aspect of the invention provides a flexible garment configured to continuously conform to a user's body when the garment is worn by the user, the garment comprising: a body sensor on the garment configured to sense one of a user's position, a user's movement, and a user's physiological status and thereby generate a body sensor signal; a conductive trace on the garment, connected with the sensor and configured to communicate the body sensor signal from the sensor to a sensor module for analysis; an interactive sensor on the garment configured to transmit an interactive sensor signal to the sensor module when the user's hand activates the interactive sensor wherein the sensor module is configured to control an audio output and/or a visual output in response to the interactive sensor signal; and a pocket on the back of the garment configured to hold the sensor module.

An intelligent apparel item or intelligent apparel system (sartorial communications apparatus) may act as an independent body measuring mechanism. Such a mechanism may allow sensors to (automatically) register appropriate body baseline measurements, including but not limited to, arm and joint length, body mass, chest expansion, displacement, sizing/tailoring measurements, stretch measurements, and/or the deviation from a standard data set.

An intelligent garment item may include optical fibers or a bundle of optical fibers; an actuator (e.g. a vibrator, a pressure and/or trigger point device); a peripheral or accessory (e.g. a speaker, a microphone, a display, a keyboard, a switch, a camera, an illuminating system, etc.).

Additionally, an intelligent apparel item or intelligent apparel system may be infused locally or throughout with a desired substance, such as another aromatic element, a deodorant, an electrolyte, a gel, a medication, a mineral, an ointment, a lotion, a perfume, a topical solution, or a vitamin. In some embodiments, an intelligent apparel item may perform as a transdermal delivery system, including, for example, as an iontophoretic delivery system. In conjunction with the intelligent wear electronics and sensors, a transdermal delivery system connected with an intelligent garment item can not only deliver medications and other item to a user, but the intelligent garment item can monitor the intelligent wear user before, during, and after delivery to ensure proper dosage, and to monitor desired vital signs and/or specific medical or safety criteria. Such monitoring may also be done in the absence of a transdermal delivery system.

An intelligent apparel item may contain a reservoir of desired material. A material may be, for example, an aerosol, a gas, a gel, a liquid, a plasma, a solid, etc. Such materials may be delivered to the user or to an area near a user. For example, an intelligent apparel item may include a burst and leak resistant "release" pouches. Such a pouch may comprise an internationally approved (such as with certified hazard analysis) disbursement mechanisms for a non-flammable aerosol/gas/ and/or liquid dispenser (release pouch). Such a pouch may be triggered to release its contents via sensor feedback and invoked responses. Such a pouch may be used for any reason, such as for an emergency management application, firefighting, medical use, military use, personal safety, security, etc.

An intelligent apparel item may contain a temperature control application. Such an application may include a "heat zone" or "cold zone" application, either alone or in conjunction with each other. An intelligent apparel item may be configured to utilize or incorporate a phase change material. A "heat zone" or "cold zone" application may activate or adjust such a phase change material, such as in conjunction with other sensors (electromyography, goniometry, thermostat, temperature, skin galvanic, etc.)

An intelligent apparel item may contain . . . which may be activated based upon disability sensors indicating a reduced or over-extended range of motion or misaligned angular measurement. These sensors may work together or alone to immediately pinpoint areas of fallibility and evoke therapeutic responses.

An intelligent wear item may include a shielding property. Such a shielding property may include protection from digital hacking such as of a sensor, data, within a wide area human node (WAHN) on or near an intelligent wear item. An individual or a group may form such a shielding property such as a "digital barrier" zone. Forming such a zone may include forming jamming effects, forming transmission effects, or forming both types of effects. Such a zone may allow for the simultaneous receipt of allowable transmission/telemetry/data while simultaneously transmitting jamming signals.

An intelligent apparel item may include one or more elements configured to provide an action to a user, such as a defibrillator action, a stimulatory action, a vibratory action. For example, an intelligent apparel item may include a transcutaneous electrical nerve stimulation (TENS) unit, which may be useful, for example, for providing therapeutic nerve stimulation for healing and/or physical therapy. Any stimulator can work alone or conjunction with another sensor or function such as a heat zone or a cold zone for the activation of multi point therapeutic concentrations.

Various functions or functional components may be incorporated into an intelligent apparel, or may be left as stand-alone elements integrated into the system, such as follows. A WAHN may be integrated. Multiple intelligent apparel users may work in concert with the included intelligent apparel sensors, in addition to having the benefit of the data acquisition based upon their individual sensor readings, to create a wide area human node ("WAHN") by having multiple intelligent apparel users in proximity to one another. Such a WAHN may have amassed centralized or distributed data collection and mining. Such a WAHN may be utilized in conjunction with an intelligent system telemetry and data response system. A hot spot may be integrated. A group of intelligent apparel users may create a hot-spot, such as an internet hot-spot. Such a hot-spot may be private or public. Such a hot-spot may allow for a controllable access and consumption zone, such as for internet/Wi-Fi/cloud access. Such a hot-spot may be configured to act as a signal booster and/or repeater station, and may allow for the development of an instant wide area network shared via the intelligent apparel group. Such a hot-spot may provide an environment configured to be controllable as a one-to-one private access, or configured to be controllable as a one-to-many private/share experience. Such a hot-spot may be created on its own or conjunction with a WAHN. An intelligent system event manager may be integrated. An intelligent garment system may also be configured so that specific functional data points are assigned to different intelligent wear users in different or defined locations or environments, but when acting together in a WAHN evoke a response that is managed by the Intelligent System Event Manager. The Event Manager may have both predetermined conditional response elements, as well as Intelligent Apparel user programmability, or be managed or modified such as via a designated third party in conjunction with encrypted and password protected access. Such Event Managers can be machine learning based upon inputs, may be self-diagnostic and/or may be remotely programmable.

An intelligent apparel item may house or host a smart module (the "brain" of an intelligent apparel system). Such a smart module may be expandable and adaptable such as with a modular electronic element, sensor, and software and firmware upgrades, and may have manage compatibility with industry adopted communications protocols and data collection and distribution standards and security. An intelligent apparel system may comprise any or all of intelligent apparel item, smart module and an associated intelligent control software, a power and data distribution system and intelligent sensors.

An intelligent garment may be a foundation item or a layer added to an existing garment. It may be above, below, on, in, or extension of another (existing) garment or accessory, or any combination thereof. It may be positioned anywhere on, in proximity to, or in direct contact with the intelligent garment user's body or extremities, and may include specific and multiple sensors and activators locations, and may include or allow for the incorporation of elements such as mentioned elsewhere in the disclosure or as known to one of skill in the art, including, for example, a printed antenna, an identification tag, an RFID elements and/or other elements not already embedded within a sensor.

In some embodiments, an intelligent garment may be a stand-alone garment, such as a single-layer compression garment or any other type of form-fitting or adherent-to-the skin garment, as described elsewhere in the disclosure (e.g. such as a short-sleeved shirt, a long sleeved shirt, a V-neck shirt, a turtleneck shirt, a tank top, shorts, underwear, leggings, leotards, gloves, feet gloves, a balaclavas, a hoodie, etc.). An intelligent garment may include electronics and connections, sensors, touch points, optical fibers, actuators, and/or peripherals. Any such items may be located on an internal surface of the garment, an external surface of the garment, or may be contained (e.g. embedded or woven) within the garment. In some embodiments, an intelligent garment may include one or more body sensors and one or more interactive sensors (touch points). Such an intelligent garment may include a.) specific or multiple electrodes, conductive ink resistive sensors, conductive ink capacitive sensors that may use a direct skin contact placed on an internal surface of the garment for data gathering (e.g., brain electrical activity, heart rate, motion detection, muscle electrical activity, oxygen saturation, skin conductance, skin temperature, tissue oxygenation, etc.) and/or for haptic feedback, such as a vibrating activator or actuators and, b.) specific or multiple electrodes, conductive ink resistive sensors, and/or conductive ink capacitive sensors, which may be printed or incorporated on an external surface of the garment and useful as an interface for a user input (e.g. an interactive sensor or touch point). Such an interactive sensor may provide visual and audio feedback.

In some embodiments, an intelligent garment may have a single garment with a double layer (or may have more than two layers) and may allow for a differentiated collection of intelligent garments (such as, a buttoned-up shirt, a coat, gloves, a hoodies, pants, a polo shirt, shoes, shorts, a vest, etc.) each with an internal (compression) support layer. An external layer may be configured to conform to a user's body or may be configured to not conform to a user's body. Each layer may include a specific category of elements such as sensors, probes, electrodes, conductive ink resistive sensors, conductive ink capacitive sensors, and/or actuators. The internal layer (e.g. conformable or compression layer) may be configured to allow for direct skin contact when the garment is worn by a user, and the external layer may be configured as a user interface and/or feedback provider.

In some embodiments, an intelligent garment may be configured both to be used as a stand-alone item as well as be used in conjunction with one (or more than one) other intelligent wear item in an intelligent wear system (e.g., intelligent wear pants and an intelligent wear shirt worn with intelligent wear shoes, or an intelligent wear polo shirt worn with intelligent wear shorts or intelligent wear pants).

In some embodiments, a first intelligent garment, whether configured to be worn alone or worn in conjunction with a second intelligent garment (or configured for both), may have two layers or may have more than two layers. A first or internal layer, such as a flexible layer for example, may be configured to conform to a user's body. Such an internal layer may provide contact or close proximity between an element such as a body sensor on the layer and a user's body. A second or external layer may be configured to fit loosely over a user's body (as well as over an internal layer). Such a second layer may provide a looser-fitting, more comfortable, more fashionable and/or more socially acceptable looser outer garment. Such a system of two or more layers may provide a looser-fitting, more comfortable, more fashionable and/or more socially acceptable looser second (outer) layer while simultaneously providing a conforming first layer having a pathway for elements to function by contacting or coming in proximity to a user's body. Any of the layers of an intelligent garment may contain any of the elements described herein or as known to one of skill in the art. A garment may also have more than two layers. For example, a middle layer (or an outer layer) of a garment having multiple layers may provide a hidden interactive sensor (touch point) configured to transmit an interactive sensor signal when a user's hand activates the hidden interactive sensor or a user's hand comes into proximity to the interactive sensor. Two layers or more than two layers of an intelligent garment may be integral with one another (e.g. sewn or otherwise fixed together with one another) or may be configured to be temporarily attached with one another (e.g. using snaps or buttons) or may simply be separate items of apparel worn simultaneously. Separate or attached but separable layers of apparel may be advantageous, for example, by allowing the user flexibility to use each of the layers with another item of apparel (mix-and-match). For example, a user may be able to have a smaller number of relatively more complex or more expensive inner layers (including sensors, connectors, etc.) (which inner lay may not be generally visible to another person when worn) and a larger number of external layers that provide more choice and variety in the user's appearance. A user may have two (or more) internal layers that have different configurations of elements. Each internal layer can be used with a different external layer. An outer layer may be configured to cover an inner layer. An outer layer may be configured to only partially cover an internal layer. An outer garment or outer layer may be specifically designed to "match" or complement or otherwise be considered attractive or fashionable when worn with an internal or other intelligent garment.

Any system of two or more intelligent wear items (including but not limited to items described elsewhere in this disclosure) may be used together. Such an intelligent garment may have a single layer or may have two layers or have more than two layers. An internal layer, such as a flexible compression layer for example, may be configured to conform to a user's body. A stand-alone item, as well as the intelligent wear system as a whole, may have a power (and data) distribution system that supplies and routes the required power and data paths in order to operate the various elements, such as the multitude of electronics and sensors, actuators, conductive ink resistive sensors, conductive ink capacitive sensors, electrodes, and probes located in the various garments and to manage the data flow between the sensors and the smart module, and the communication ports and protocols that manage the system.

In some embodiments of an intelligent wear system (such as, for example, a shirt and shorts) an internal compression layer of a multi-layered top garment (such as a shirt) may act as a cross-connection component between the top garment and a bottom garment. An internal layer may extend in length lower than the external layer, such as down to the hips, and may be configured to support the power and data distribution system between the different pieces of garment. A proper connecting system may include but is not limited to a conductive glue, a snap, and a solder element and may allow or provide an electrical connection between different components of the intelligent apparel system and/or between an intelligent apparel component and an intelligent accessory.

As described, an intelligent garment may be flexible and/or configured to conform and/or configured to continuously conform to a user's body. An intelligent garment may comprise any material that is flexible and/or able to conform and/or able to continuously conform to a user's body, such as those known to a person having skill in the art. Such a flexible or conforming garment may be especially comfortable and/or attractive.

In some embodiments, an element, hardware, etc. on an intelligent garment may be flexible and/or configured to conform and/or configured continuously conform to a user's body. In some embodiments, an element, hardware, etc. may be hidden or out of view. In some embodiments, an element, hardware, etc. may be visible and may be attractively presented. Generally in the art, an element such as body sensor, an interactive sensor, a conductive material etc. is inflexible (rigid) and/or non-extensible. It may be inflexible and/or non-extensible (or may have an inflexible and/or non-extensible housing) to contain it, protect it from jarring, protect it from a stray signal, prevent it from shorting, protect it from sweat, protect it from a cleaning agent such as soap, protect it from water, etc. An element may be connected with another element or other item by a wire which may be protected by a bulky and/or relatively inflexible insulation. Such a material may be uncomfortable to a user due to their inflexibility (rigidity) and/or lack of extensibility when used by a user. Generating a conductive trace may require a balance between material qualities such as conductivity, flexibility, smoothness, and washability. For example, a sensor or wire connected to a music player such as an iPod or phone worn by a user cannot extend when a user moves. Instead, the user is constricted in movement by the wire, or allows an "extra" loop of wire to hang down so that the individual can move without constriction by the wire. Such a rigid or inextensible element may be annoying, clumsy, dangerous, and/or unattractive to a user or others. For example, a hanging wire connecting a music player may easily get in a user's way or caught by a user's hand. The wire may then pull the music player to the floor, pull on the speaker, entangle the user, etc. An inflexible (rigid) and/or non-extensible element worn by a user may be constrictive and uncomfortable because it cannot extend to conform to the user when he moves or bends.

In particular, the intelligent apparel and systems described herein may overcome problems inherent in trying to connect an element such as a sensor to another element such as module while maintaining an attractive appearance, conformability, comfort, and/or extensibility of the apparel. An intelligent apparel may be specifically designed to overcome problems inherent in trying to bridge seams with conductive materials with elongation issues, while maintaining comfort and performance. Any or all of these functional components may be incorporated into the intelligent apparel, or may be left as standalone elements integrated into the system.

In some embodiments, an element, hardware, etc. integral to, contained on an intelligent garment may be inflexible and/or inextensible. Such an element or hardware may be placed, for example, on a region of the garment configured to contact a portion of a user's body that is relatively unmoving or inflexible. Such an element or hardware may be connected with a flexible or extendible element. For example, an inflexible smart module may be placed on the back of garment and may be connected by flexible and/or extendible traces to a front of a garment. Such a trace (or other element such as electronic element or device) may be placed or contained within a seam, such as a welded seam. Such a seam may enclose the trace to prevent the trace from contacting the body which may be uncomfortable or to prevent the trace from being visible, which may be unattractive to the user or to another.

An intelligent apparel system may comprise any or all of one or more intelligent apparel items, accessories, or garments (and associated elements), a smart module, an associated intelligent control software, a power and data distribution system and one or more actuators, conductive ink capacitive sensors, conductive ink resistive sensors, electrodes, fiber optic sensors, optical probes, other probes, and/or intelligent sensors.

Figure 4:
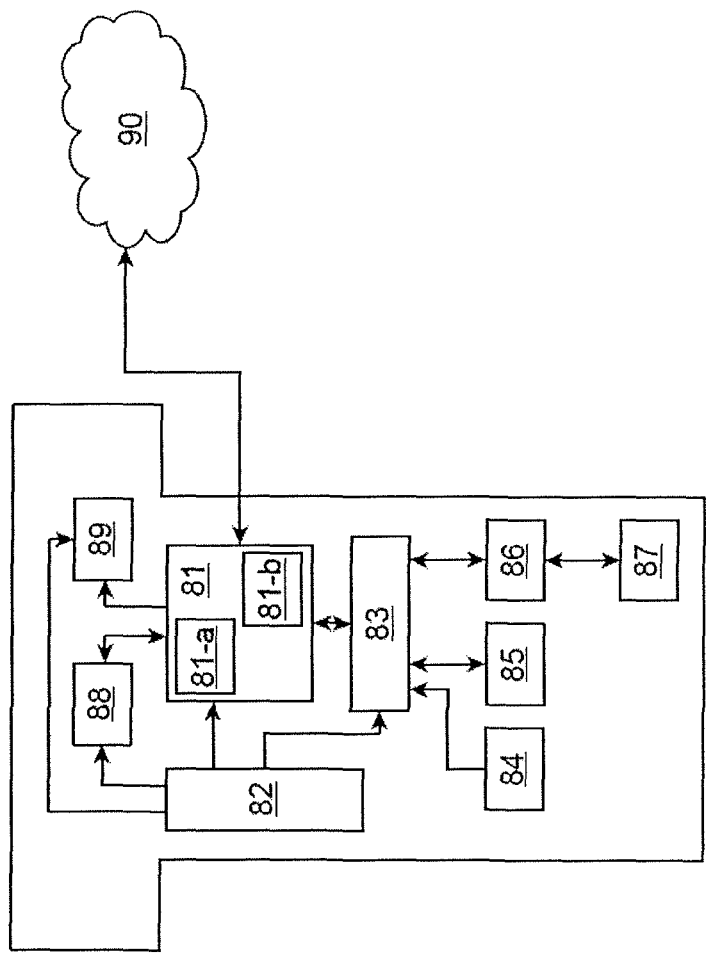
FIG. 4 shows an embodiment of a wearable communications platform configured as a shirt in a wearable communications platform with various elements for sensing and communicating.

FIG. 4 shows an embodiment of an intelligent wear shirt platform. Such a wearable intelligent platform includes a wearable intelligent garment; sensors on the wearable intelligent garment such as body sensors and interactive sensors; a flexible conductive connector on the wearable intelligent garment in the form of an ink trace for connecting sensors to the sensor module; a sensor module for managing the sensors; and an output in the form of an actuator. The shirt includes a communication platform 81 configured to control communications, such as internal communication (e.g. integral to or within any garment or accessory) and external communication to an external communication system 90 (e.g. with a computer, the cloud, etc.). A communication platform may be an electronic system, such as a phone that may be embedded in a garment or may be removable. A communication system may include an application (app) configured to process data and a sensor, such as an inertial measurement unit (IMU). FIG. 4 also shows a sensor manager 83 in electronic communication with communications platform 81. FIG. 4 further shows an interactive sensor 84, a body sensor 85 such as a conductive media trace (conductive ink) trace used as an EKG sensor in electronic communication with the sensor manager 83. FIG. 4 also shows a peripheral element 88 such as a speaker or microphone electrically connected with the sensor manager 83 via a (flexible) electrical trace. An intelligent wear module (module, SWM) may house electronics and a microprocessor(s) configured to operate an intelligent wear garment or intelligent wear system (including any intelligent accessories) may include a communication system 81, a sensor manager 83 and optionally a sensor 85. In some embodiments, such a module may comprise a housing configured to be easily removed (e.g. in one piece). FIG. 4 also shows power supply 82, which may be useful for supplying power to the communication system, sensor manager, sensors, peripherals, etc. Such a power supply may be part of the module or may be separate from it and may supply power through a trace 86.

A sensor manager may be configured to provide one or more than one the following principal functions. A sensor manager may be configured to receive and synchronize various analog and/or digital signals and/or data (e.g. samples of signals measured at a given programmable sampling rate, which may be, for example continuously or intermittent or may be binary (on/off) such as in the case of an interactive sensor). A sensor manager may be configured to provide front-end functions for an analog signal, that include but are not limited to amplification of a signal from a peripheral sensor located elsewhere on an intelligent wear item, such as an accelerometers and photodiodes, a printed sensor, and/or printed electrodes and/or touch point signals, filter an analog signal such as from an analog low-pass filter, high-pass filter or band-pass filter or stop-pass filtering a signal from a printed sensor and/or an interactive sensor (touch point), and/or multiplexing of different signals, such as, for example those coming from various printed sensors, interactive sensors (touch points), etc. A sensor manager may be configured to convert an analog signal into a digital signal, such as a digital signal coming from any peripheral sensor such as an accelerometer, a photodiode, a printed sensor, an interactive sensor (touch point), etc. A sensor manager may be configured to provide a power supply to one or more elements in or on an intelligent wear system item such as in or on a garment or an accessory. A sensor manager may provide a power supply, for example, by interfacing with a power source (e.g. a battery) and sending electrical power from it to a peripheral sensor, such as to an accelerometer, a photodiode, a printed sensor, a physical sensor, and/or an interactive sensor (touch point), etc. on an intelligent wear item. A sensor manager may be configured to pre-process data by implementing functions that include but are not limited to digital filtering of analog and/or digital signals, coding of interactive sensor (touch point) signals, conversion of continuous data into time series data, etc. sensor manager may be configured to communicate by specific data communication protocols. A sensor manager may be configured to transmit and/or control a signal and to send appropriate feedback to the user based on the signal, such as via a haptic activator or actuator or touch pad on an intelligent wear item an audio output, a visual interface, etc. Such an actuator may be connected with the module, for example, by a vertical trace. A haptic actuator may transduce an electrical signal (e.g. from a module) into a mechanical force. A haptic actuator may provide a feedback such as a force, a vibration, or a motion to a user's body such as an arm, a face, a finger, a foot, a hand, a head, a leg, a neck, a thumb, a toe, and a torso. A haptic actuator may be an electroactive polymer, an electrostatic actuator, a piezo actuator, etc. Haptic feedback may be sent to a single actuator or to a plurality of actuators and may be based on sensor signals from one or from more than one sensors. Haptic feedback may be provided to 1, 2, 3, 4, 5, 6, 7, 8, 9, 10 or more than 10 haptic actuators. For example, a sensor module may process sensor signals from a plurality of position-based sensor on an arm of a user, such as a user performing yoga, and may send signals to a plurality of haptic actuators to encourage the user to move the arm to a different position.

An intelligent wear item or intelligent wear system may include an intelligent wear manager. A sensor manager may be part of an intelligent wear module or may be separate from it. Such an electronic module may manage actuators, conductive media (conductive ink) resistive sensors, conductive media (conductive ink) capacitive sensors, electrodes, probes, sensors, and any other components and activities. An intelligent wear module may be configured to run on, for example, a rechargeable battery and/or a disposable battery.

An intelligent wear module may be configured to have one or more of the following functions: An intelligent wear module may be configured to facilitate communication between items within an intelligent wear system and/or from/to an intelligent wear system to/from outside an intelligent wear system (e.g. the cloud, a computer, a phone, a tablet, etc.). An intelligent wear module may be configured to facilitate communication, for example via one or more standard protocols and/or one or more novel or proprietary protocols, such as via Bluetooth, infrared (IR), a mobile phone equipped with a SIM card reader (such as for immediate connection to the cloud via a global system for mobile communications using any carrier or subscription such as global system for mobile communications (GSM); general packet radio service (GPRS); enhanced data for GSM evolution (EDGE); universal mobile telecommunications system (UMTS); any other advanced mobile system network); radio frequency (RF), sonic signature, Wi-Fi, etc., or any other protocols as appropriate. An intelligent wear module may be attached to, be in proximity to, or manufactured within, an intelligent garment, an intelligent wear accessory, Wi-Fi, etc. An intelligent wear module may contact or be in proximity to other elements or components of an intelligent wear system, such as, a power and data distribution system (PDDS), associated power traces, intelligent sensors, etc.

An intelligent wear module may be configured for integrating, storing, playing back, managing (uploading, downloading, distributing, accessing, comparing, analyzing, etc.), and controlling one or more of: 1.) activators, capacitors, 'power traces' and any associated power and sensors, probes, transmission and receptions points, such as two ways communication, etc. 2.) any intelligent sensors and any of their various (and numerous) data collection and transmission points via SM, 3.) local data and content storage (memory), 4.) transmission and receipt of external data and content, 5.) programming of the content assignment with the intelligent apparel interactive sensors (touch points), 6.) (immediate) converting of biometrics and motion data into "Expressions" (see below), 7.) generating audio, haptic, and/or visual feedback based on a training session or other downloadable program, 8.) initiating and controlling transdermal control processes, 9.) local or external compliance, comparative, and irregularity feedback analysis based upon data collection or programming, 10.) managing plug and play aspects of electronics and intelligent wear module enhancements, and 11.) facilitating the social media elements such as sharing, location based services, and interactions, and 12) compatibility with industry accepted protocols. In some embodiments, an internal intelligent wear module may be configured to be scalable and expandable. In addition to core functionality and processing power of the intelligent wear module, additional enhancements or functionalities may be included in an intelligent wear module or may be added (e.g. in a plug-and-play environment) to the intelligent wear module to, for example, increase functionality of the module and/or control additional enhancement (elements) added elsewhere in the intelligent wear system. Such enhancements and functionalities include, but are not limited to, battery power, a bone stimulator, Bluetooth, a camera, a cold pack, a defibrillator, a dispenser, a display, earphones, global positioning system (GPS), a heat pack, infrared (IR) functionality, a jack (e.g. for a microphone, a light/LED, photo, etc.), radiofrequency functionality (RF), a speaker, an additional sensor a vibrator, a solar cell, a transdermal delivery systems, and Wi-Fi. In some embodiments, an intelligent wear module may include a software development kit and/or intelligent control software.

An intelligent wear module may include a software development kit (SDK) configured to allow the creation of an additional application ("app") for the module. Such an application may be based on an existing (commercial) software package or may be based on a proprietary software package. Such an application may be made on a fee basis or may be made free to the user community. A developer (e.g. a member of the developer community) may develop applications using default or optional actuators, sensors, or other elements from the intelligent wear system specific to certain uses such as for 1.) a group activity such as a virtual game, an activity competition, a sports challenges and rankings, etc., or for 2.) a personal activity, such as a specific control system for healthcare, a specific control system for entertainment purposes, etc.

An intelligent control software may include but is not limited to a software concept designs (e.g. a proprietary software as part of the module) that facilitate: (user) creating (e.g. by the user) of an audio file from the user's voice, creating sounds effects, editing and managing user content such as grabbing a "needle drop" or specific section of music from a user's library, assigning a sound effect to a body part, modulating a musical response based on a user's movement (such as increasing the volume or the brightness of sound based on the user raising his arm), activating specific biofeedback as a musical outputs (such as a (musical) rhythm based on a user's heartbeat), etc. Other types of software may allow: controlling an LED lighting on a shirt (by a user) to play back or synchronize the lighting with a voice or music, controlling a camera configured for facial recognition and triggering an audio effect, a light effect, or a Facebook response when someone known is recognized, etc. A specific functional software category may include but is not limited to, supporting entertainmentwear, healthwear, heatwear, safetywear, securitywear, and/or sleepwear. Such software may, for example, create an automatic response (an automatic trigger) that may be based on, for example, a sensor response or a biometric analysis. Such an automatic response may initiate a product purchase, a food delivery, a medical doctor notification, or a motivational item. In some embodiments, an automatic response may include a list of suggested items or alternative activities to those initiating the automatic response.

An intelligent garment or apparel system may include a power and data distribution system ("PDDS"). Such a power and data distribution system may be applied to or incorporated into an intelligent apparel item. Such a power and data distribution system may supply and/or route any power and/or data paths to operate the multitude of electronics and sensors used in conjunction with an intelligent apparel. Such a power and data distribution system may facilitate communications between actuators, conductive ink capacitive sensors, conductive ink resistive sensors, electrodes, nodes, sensors, a wide area human node (WAHN) and/or any of their associated accessories. Additionally, a power and data distribution system may manage data flow between sensors and the smart module, the communication ports, and the protocols that manage the system.

Within a power and data distribution system, an intelligent wear system may utilize a "power trace". Such a power trace may act as a connection point(s) for and between intelligent wear sensors. Such a power trace may be configured to be a sensor. In addition to being a conduits for the flow of power and data transmissions, a power trace may also create an interactive sensor (touch point) that can be activated through any or more mechanisms including but not limited to capacitance, direct touch, gesture controls, light (spectrum specific), proximity, and sonic signatures/sound. A gesture control may allow a user (or another individual) to control an aspect of the intelligent wear system with a gesture, such as shaking a hand up and down to function as 'increase the volume' and 'decrease the volume'. Gesture control recognition may be standardized (e.g. determined by the module or an application such as from a library of pre-recorded and/or standard gesture based commands) or may by user control (e.g. a user may be able to determine how a module responds to a particular gesture). A library of recognizable gestures may include, for example, gestures from sign-language. A gesture-based command may comprise a recording of data from movement detected from intelligent wear accelerometers during a gesture event. Such a recording may be authenticated by a user and stored. Such a command may then be detected by recognition algorithms to execute a particular operation. A gesture based command may be based on data from an intelligent glove, which may comprise a plurality of accelerometers (such as on each finger, the palm, etc.) An intelligent wear button or trigger point on a garment (such as a shirt) can be programmed to elicit a specific response or functionality, such as activating a sound file, turning a display on or off, initiating a content or data transfer, initiating a transdermal flow, soliciting biometric feedback, controlling (changing) a volume level (volume control), controlling lighting, controlling a heat level, controlling a sensitivity level for a sensor, transmitting data, and managing connections and communications for and between a smart module, the internet, a cell phone, and/or a user's smart phone (such as for an internet upload and downloads, etc.). Such an intelligent wear button or trigger point may take the place of a specific hard mounted button or switch. A power trace may comprise one or more than one component known to one of skill in the art or hereafter devised such as 1) an electrically conductively media (electrically conductive ink), an additive, or a material embedded in, on, or around a textile fibers within an intelligent apparel, a fiber optic such as via one or more of a core, dye, nano configuration, resin, spray, thread, or via such other manufacturing and/or deposition application such as embossing, heat transfer, pressing, screen printing, sublimation, weaving, working alone or in conjunction with or via 2) a topical conductive component added, affixed, or sewn onto the intelligent garment including but not limited to carbon fiber, flex film a molded part, nano tubes, a printed circuit board, a rigid material, etc. material, and/or 3) working wired material (such as a material known to one of skill in the art) and a harness such as a carbon fibers or the like, which may be produced directly onto the intelligent apparel, applied via digital or direct print, or produced on a substrate (such as in the form of a transfer sheet or the like), and applied to the intelligent apparel via, for example, an industry acceptable mechanism such as a heat transfers, a sonic welds, or a method known by those skilled in the art. In some embodiments, a transfer may be electrically tested prior to being placed on an intelligent apparel item. Such testing may allow higher quality or less expensive intelligent wear manufacture since only good-quality transfers (e.g. electrical traces) will be transferred onto a garment; garments will not be rendered useless by a defective trace. A trace may additionally comprise an adhesive or glue which may be solidified to create a trace or may be useful for holding a trace onto a garment.

In addition to a power functionality and a communication functionality, a power traces can be designed in such a way so as to create a heat panel within the apparel. For example, when working in combination with a phase change material, a power traces can be used to regulate and hold a hot or cold environment within the apparel. Such a power trace may further work with a sensor, such as a thermostat, to create a further personal environmental control or to respond to a sensor input with an application of heat or cold to a specific location(s) within or on the intelligent apparel.

An intelligent garment or apparel system may include one or more than one intelligent sensor. A "power trace" (such as described elsewhere in the disclosure) may be used to supply power to a printed and/or physical sensor and/or a detector array strategically located on the apparel ("intelligent sensor"). Such a sensor may include a sensor that is not self-powered. Such a sensor may be configured to measure any of a host of physiological properties of the intelligent wear user that include but are not limited to, 1). Heart rate, 2). Respiratory rate, 3). Inspiratory time, 4). Expiratory time, 5). Tidal volume, 6). Rib cage contribution to tidal volume, 7). Abdominal contribution to tidal volume, 8). Perspiration, 9). Pulse, 10). Moisture, 11). Humidity, 12). Elongation, 13). Stress, 14). Glucose Levels, 15). pH balance, 16). Resistance, 17). Wear, 18). Motion, 19). Temperature, 20). Impact, 21). Speed, 22). Cadence, 23). Proximity, 24). Flexibility, 25). Movement, 26). Velocity, 27). Acceleration, 28). Posture, 29). Relative motion between limbs and trunk, 30). Location, 31). Specific responses or reactions to a transdermal activation. 32). Electrical activity of the brain (EEG) such as in multiple sites, 33). Electrical activity of multiple muscles (surface EMG), 34). Arterial oxygen saturation, 35). Muscle and tissue oxygenation in multiple sites, 36). Oxyhemoglobin and/or deoxyhemoglobin concentration in multiple sites. Such a "intelligent sensor" may communicate with a smart module via wired or now known long range, medium range, and/or short range wireless application and communication protocols that include but are not limited to Bluetooth, FTP, GSM, Internet, IR, LAN, Near Field, RF, WAP, WiMAX, WLAN, WPAN, Wi-Fi, Wi-Fi Direct, Ultra Low Frequency, or hereafter devised wireless data communication systems, versions, and protocols for power and data communication and distribution; and may allow for all (or many) of the systems to work alone or together, and may be reverse compatible.

In some embodiments, by combining data from the sensors with input data from the intelligent wear user, and with the additional input from a 3rd party, the intelligent wear system can build or continue to build a portfolio of knowledge on the intelligent wear user, including, but not limited to, for example, "likes" and "dislikes", allergies and other possible negative responses to a stimulus, an associated biometric feedback from such a reaction, and the ability to send an emergency call or Short Message Service (SMS) to others when the intelligent wear user is in distress from such a reaction.

Additionally, based upon the user's experience, the process may initiate ordering/shopping from the user directly to a producer/supplier location or site.

An intelligent wear system according to the disclosure may include providing, developing and/or creating software applications, mobile device applications, and hardware applications; providing, developing and/or creating soft-goods (such as a textile, a fabric, an apparel merchandise); and/or hard-goods (such as an exercise equipment, wrist band, etc.). Such an application may be utilized to create visual, audio and/or tactile effects that may be controllable by the user of such applications such as on soft-goods or hard-goods. Such applications may be used in order to sense, read, analyze, respond, communicate and/or exchange content/data feedback with the user. Any type of communication protocol may be used, such as in conjunction with the internet, attached or separate mobile devices, and other communication tools.

Such utilizing converging technologies (i.e., but not limited to incorporating electronics, software, biometrics), Specialized location based elements and tracking components, inks, Nano formulations, conductive materials, component transmitters, analysis and artificial intelligence response software and hardware, receivers, low, no, and high powered sensors, printed speakers, connectors, Bluetooth and USB functions, energy generating elements, medical and wellness tracking and feedback devices, body movement and efficiencies and mechanisms for tracking and analyzing the same, and other such like elements, alone or in conjunction with each other may be utilized in an intelligent wear system.

Figure 5B:
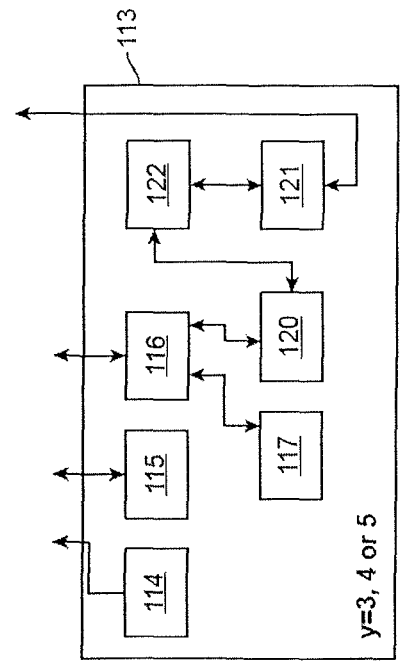
FIGS. 5A-5B show an embodiment of a wearable communications platform having multiple, interconnected garments with various elements for sensing and communicating.
Figure 5A:
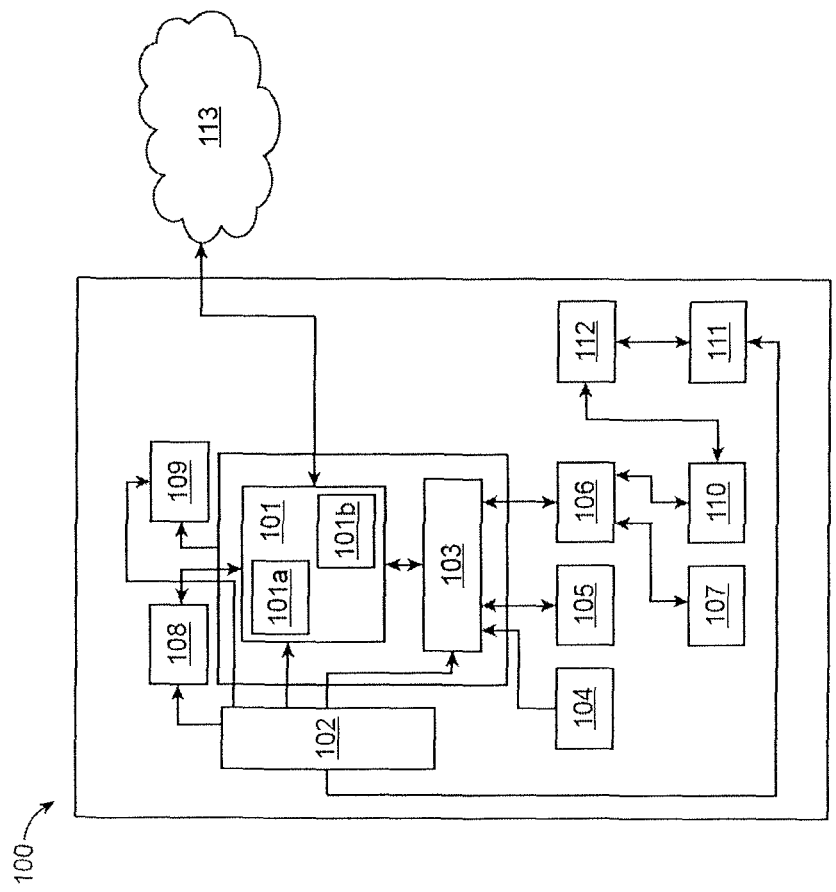

FIGS. 5A-5B show embodiments of intelligent garment items. In a particular embodiment, FIG. 5A shows a first garment, such as a shirt, configured to be worn on a user's torso while FIG. 5B shows a second (or third, fourth, fifth, etc.) garment, such as shorts, pants, headgear, etc. electrically connected with the first garment such that the sensor manager and communication system and application platform in the first garment manage the sensors from the second garment. FIG. 5A shows an embodiment of an intelligent wear shirt arrangement. Shirt 100 includes a communication system and application platform 101 configured to control communications, such as internal communication (e.g. integral to or within any garment or accessory) and external communication to an external communication system 113 (e.g. with a computer, the cloud, etc.). A communication platform may be an electronic system, such as a phone that may be embedded in a garment or may be removable. A communication system may include an application platform 101a (app) configured to process data, a communication device 101b, such as Wi-Fi, Bluetooth, GPRS, a universal mobile telecommunications system (UMTS) phone and a sensor 101c, such as an inertial measurement unit (IMU). FIG. 5A also shows a sensor manager 103 in electronic communication (indicated here and throughout by an arrow) with communications system and application platform 101. FIG. 5 further shows an interactive sensor 104, a body sensor 105 such as a conductive media trace (conductive ink) trace used as an EKG sensor in electronic communication with the sensor manager 103. FIG. 5A also shows a body sensor 107 (e.g. a peripheral sensor such as a tri-axis accelerometer, etc.), a peripheral element 108 (such as a speaker, microphone, display, keyboard, switch, camera, illuminating system, etc.) electrically connected with the sensor manager 103 via a (flexible) electrical trace. An intelligent wear module (module, SWM) may house electronics and a microprocessor(s) configured to operate an intelligent wear garment or intelligent wear system (including any intelligent accessories) may include a communication and application system 101, a sensor manager 103 and optionally a sensor 105. In some embodiments, such a module may comprise a housing configured to be easily removed (e.g. in one piece). FIG. 5A also shows power distribution system 102, which may be useful for supplying power to the communication system, sensor manager, sensors, peripherals, etc. Such a power supply may be part of the module or may be separate from it and may supply power through a trace 106. Such a power supply may supply power to the first garment as well as to the second or additional garments or electrically connected intelligent wear items. FIG. 5A also shows an actuator 109 on the shirt in electrically contact with and controlled by the intelligent wear module. FIG. 5A also shows a light system including a light sensor 110 such as photodiode, a phototransistor, a photo-resistor, etc., an optical source 111 and an optical fiber 112 (or bundle of optical fibers) in electrical connection.

FIG. 5B shows a second (or third, fourth, fifth, etc.) garment, such as shorts, pants, headgear, etc. electrically connected with the first garment, including an interactive sensor 114, a body sensor 115 (such as an EMG sensor), which may comprise a conductive media trace (conductive ink) trace 116. FIG. 5B also shows a body sensor 117 (e.g. a peripheral sensor such as a tri-axis accelerometer, etc.). FIG. 5B also shows a light system including a light sensor 120 such as photodiode, a phototransistor, a photo-resistor, etc., an optical source 121 and an optical fiber 122 (or bundle of optical fibers) in electrical connection.

FIGS. 6A-E how various embodiments of an intelligent garment system comprising flexible apparel configured to continuously conform to a user's body when the garment is worn by the user. The garments include a plurality of body sensors. Each body sensor generates a body sensor signal based on a user's body status or user's characteristic such as a user's position, a user's movement, or a user's physiological status. A plurality of body sensor signals are sent to a sensor module where a sensor board (FIG. 6E) on the module obtains the body sensor signals and the module processes the signals to generate an output. Various outputs can be generated.

In some embodiments, an intelligent apparel item and any accessories may be designed to allow a user to express themselves by transforming a user's biometric data into a specific expression or experience. Such an expression or experience may vary depending, for example, on a) the specific garment (and accessories) and b) the particular algorithm and communication provided by the smart module.

Varying levels of complexity of physiological signals may be utilized in order to transform a user's biometric data into a specific expression or experience. A particular garment may determine the accuracy and varying level of complexity of the biometric physiological signals to be used for an assessment, e.g., such as for communicating feedback related to relaxation level and posture alignment for performing yoga, movement for dancing, movement precision for gymnasts, etc. For example, a leotard (i.e. a dancer's one-piece full body compression garment incorporating full leggings, socks, shirt with long sleeves, gloves and a hood/balaclava), may provide more accuracy then would a T-shirt or a polo shirt alone because it can cover the entire body of the user with a maximum number sensors and actuators. In one embodiment, a 'full body leotard' has 19 accelerometers: one on each shoulders and hip (4), one of each knee and elbow (4), one on each hand (extensor indices) (2), one on each foot (on the hallux) (2), one on each ankle (2), one on each wrist (2), and one on the neck (rear) (1), one on the chin (1) and one the upper parietal bone (1). Such a garment may other types of sensors, including but are not limited to, a heart-rate monitoring sensor (e.g., in direct contact with the skin); thoraco-abdominal respiratory motion sensor; a skin conductance sensor (e.g., in direct contact to the skin). Such sensors may be connected through power traces to a sensor module, such as one incorporated into the garment between the scapulae. An interactive sensor (touch points) (from 1 to 10 or more than 10 sensors) may be located on the front of the chest, shoulders, legs and other parts of the body. By activating an interactive sensor(s) (touch points) the user is able to send a command to the module. A command can be anything, such as calling a friend, sending a message, etc. A user may chose a particular garment based on the type of expression or experience they are in the mood for or may chose a particular program or algorithm of interest on a garment comprising a plurality of programs or algorithms.

An intelligent wear module may host various types of software for implementing various algorithms to evaluate and process each expression or experience such as experiences and expressions described below and elsewhere in the disclosure. Such software and algorithms may be regularly updated and downloaded to a module, such as through a specifically developed updating software. Biometric data such as physiological signals may be collected by a sensor manager which may be located in the intelligent wear module and then sent to the intelligent wear module. Such signals (or signals processed by the intelligent wear module) may be sent to the cloud by any modality, including but not limited to real-time communication. An intelligent wear module (sensor management system) may also process and evaluate if a user's movements, posture, etc. are correct or as desired. Such a module may provide feedback to the user, for example by utilizing a specific software to communicate or provide a coded signal to a haptic or other type of activator ((e.g. for a vibration to an actuator) to the user. Such a feedback may be controlled, for example, via an open-loop feedback system or via a closed-loop feedback system.

A few non-limiting embodiments are described herein by way of example. FIG. 6A shows a "Sound of Action" garment system configured to transform a user's movement (and physiological state) into music (e.g. a musical expression of the user's state). FIG. 6A shows a sound of action shirt 130 with an electrocardiogram (ECG) sensor on either side of the front of the shirt to sense the user's heart rate. An ECG sensor may be in contact with a user's skin in order to sense a heart rate. The sound of action shirt 130 has accelerometers on the shirt sleeve (A1, A2) and the sound of action pants 132 has accelerometers (A3, A4) on the pants legs, and the sensor module comprises an accelerometer A0. Such a sensor may sense the user's position or the user's motion. Any type of accelerometer may be used (e.g., a tri-axis accelerometer, an inertial measurement unit (IMU)) and may be configured to measure any parameter(s) to determine user motion or infer user motion (e.g. an accelerometer, a gyroscope, a magnetometer, etc.). The body sensor signals may be sent to the sensor module which records the data (e.g. the user's heart rate and the user's movement). Rather than telling another person how they feel, a user may communicate to them their biometric data; thus rather than provide an interpretation of the reality, they express true, objective facts. In some embodiments, the module may transform the data into audio feedback, visual feedback, or touch feedback based on the data. Such feedback may be used by the user or may be shared with others. In some embodiments, the data is converted into music based on the body sensor signals. In some embodiments, a user can play the music through an audio output (such as speakers which may be anywhere including on the module, earphones, etc. as described elsewhere in this application). A user may allow feedback to be accessed by others (e.g., a friend(s), a loved one(s)), which may allow the other access to a user's inner feelings. In some embodiments, a user can upload the music to a webpage (e.g. a specific, protected intelligent wear webpage). In some embodiments, a user can send (share) the music with a friend(s). A user can choose a type of music they prefer (such as e.g. classical, country, disco, electronic, hip-hop, jazz, modern folk, pop, rap, rock, etc.). The user can control any other aspects of music generation (such as, e.g., dynamics, tempo, etc.).

As shown, the action shirt has interactive sensors (touch points). The touch points may are configured to control various aspects of a garment system, including but not limited to controls (e.g. bass, dynamics on/off, volume, etc.) on or to a music playing device (earphones, speakers) or controls on a communication system (e.g. texting, webpage upload, etc.)

One aspect of the invention provides a method of providing feedback for encouraging behavior modification comprising: conforming a conformable garment to the torso of an individual, the conformable garment comprising a plurality of body sensors configured to conform to the torso; sensing a plurality of signals from the individual's body with the plurality of body sensors; communicating the plurality of signals to a sensor module attached to the garment; processing the plurality of signals with a processor in a sensor module attached to the garment to generate an output signal; converting the output signal into a feedback output wherein the feedback output comprises a haptic feedback; and delivering the haptic feedback to the individual to thereby encourage the individual to modify a behavior. In some embodiments, the haptic feedback comprises delivering a vibration to the individual to encourage the individual to change a position, such as a body position, a limb position, a head position, a joint position, or a neck position.

FIG. 6B shows a "Body Alignment" garment system configured to provide (immediate) feedback on a user's body posture and alignment so that the user may correct a body position or alignment. Similar to the "Sound of action" shirt above, the alignment shirt 132 has an electrocardiogram (ECG) sensor on either side of the front of the shirt to sense the user's heart rate and accelerometers (A1, A2) on the shirtsleeves, on the torso of the shirt (A5, A6), on the pants legs (A3, A4) and on the sensor module (A0). An alignment shirt 132 has a first strain gauge SG1 on a first sleeve and a second strain gauge SG2 on a second sleeve and strain gauges (SG3, SG4) on the pants. Such a strain gauge may comprise a flexible and/or variable resistive media configured to measure movement, such as bending or rotation of an arm or leg around an elbow or knee. The alignment shirt may include an electromyography (EMG) sensor. Such a sensor may comprise a conductive electrode for measuring a level of muscle activity. A pre-amplifier and/or amplifier may be connected with the EMG sensor, which may be useful for boosting a relatively weak EMG signal. Similar to the "Sound of action" shirt, the alignment shirt 32 has interactive sensors (touch points) that may be configured and used as described elsewhere in the application. In order to detect respiration (such as the frequency of breathing, the depth of breathing, etc.), the body alignment shirt also includes a first respiration sensor RESP1 that spirals around the chest (rib cage) and a second respiration sensor RESP2 that spirals around the abdomen. Any type of respiration sensors may be used. In one embodiment, a respiration sensor comprises a strain gauge, such as a conductive strain gauge configured to change a level of conductance in response to a change in strain gauge length (e.g. stretching based the user's body stretching). Body sensors gain data from the body and send the data to the sensor module, the sensor module processes the response, the sensor module compares the response with a standard (or with a previous measurement), the sensor module elaborates the response, the sensor module provides feedback and a haptic actuator(s) acts on a portion(s) of the body that is different from the standard (or a previous measurement) such as by providing a vibration. The body sensors may continue to send data and as the user adjusts (corrects) a position of a portion of the body, and the sensor module processes the data, the sensor module may be configured to stop the haptic actuator from vibrating (e.g. to stop sending a signal to vibrate).

A specific positioning of accelerometers, gyroscopes, magnetoscopes and/or other sensors may provide data from a user on the (precise) movements of a user (e.g. an athlete, a patient, a yogi, etc.). Such movements may be used to determine the (precise) optimal execution of their movements in order to maximize the proper optimization of their bodies. Such optimization may be calculated by taking in consideration one or more factors (such as activity, age, body alignment, body structure, body weight, environment, gender, health, skeletal structure, time of the day, etc.). Use of the module for body optimization may include the steps of calculating (in real time) the variance between the users actual movements with an optimal movement and providing (real time) feedback such as through a haptic actuators or other technology to suggest the proper movement, the proper sport stroke or movement execution, the proper body alignment or posture. etc. The various sensors gain data from the body and send the data to the sensor management system. The sensor management system may elaborate the response and provide a feedback, such as a vibrating effect configured to act on those portions of the body that are OFF from the correct pattern or position. In some embodiments, as or after the user adjusts their movement to perform the correct execution, the actuators may reduce the vibration feedback until reaching no (0) vibration when the proper movement is finally executed. In some embodiments, a feedback may be delivered to the user for a certain time period and then turn itself off, and the cycle may be repeated until an acceptable user position or user movement is sensed by the sensors. In some embodiments, a library of training sessions for activities, exercises, postures etc. may be available on an intelligent wear module or may be downloaded able from a website. A user, may for example, download one, two, three, four, five or more than five of the movement optimization system modules or programs configured for improving execution of one or more athletic, sports, or other performances.

A movement optimization system may also promote correct body posture in any way. For example, a haptic (vibrating) response can help a user to correct a bad body position that might potentially cause or lead to potential injuries, and restore the correct balance and alignment. A movement optimization system may: identify, address and provide corrective action or suggestion for an ache, a pain and/or a limitations such as related to (poor) posture alignment; improve, restore and/or maintain a user's body's (e.g. user's joint, a user's muscle, etc.) full or possible range of motion; develop and improve body awareness, posture and appearance; prevent pain and/or further degeneration such as muscle degeneration or joint degeneration; prevent or help prevent a re-occurrence of a repetitive injury or reduce the severity of an injury re-occurrence; relax a user's body such as through a haptic massage effect and/or with audio input (e.g. sounds such as bird sounds, music, rain sound, waterfall sound, white noise, other sounds); identify, stimulate and/or treat a pressure point (e.g. an acupuncture point, an acupressure point, a muscle knot, a nerve point, anywhere in the body such as in the arm, back, feet, head, hip, leg, shoulder, etc.; identify, stimulate and/or treat an inflammation or other warm area; a similar (or the same) experience model may be replicated for different (or for all) programs in which proper posture is significant for the execution of the activity (ex. yoga, Pilates, stretching, etc.)

An intelligent wear system can guide dynamic expressions through a training program (such as a haptic activator used to suggest a movement working in conjunction with vocal commands which may be given or received). Such a training program may, for example, be available from a disc, a module, downloadable from a website for a user's personal use, etc.

An intelligent wear system may work real-time in a group setting (e.g. a class of students) in presence of an instructor. An instructor may instruct by: wearing a instruction intelligent device (IID), and providing guidelines from the IID to the student(s) intelligent garment. Such an instruction may accelerate the student's learning process, for example, by providing instruction and/or correction. Such an instruction may be especially helpful in activities with synchronized movements such as aerobics, Pilates, Step, Zumba, etc. (ex. right leg up, right arms down, etc.). An instruction may provide instruction through voice and/or individually customized haptic vibration to every user.

FIG. 6C shows "The Hero's Heart" garment system configured to provide feedback on the user having the fortitude to achieve a high (e.g. the highest) inner peace during the most strenuous exercise and/or actions. Similar to some other systems described above and elsewhere herein, "The Hero's Heart" garments include accelerometers, ECG sensors, and respiratory body sensors which gain data from the body and send the data to the sensor module. The sensor module processes the data and provides feedback. "The Hero's Heart" is the user with a high level of inner peace (or low stress level) while achieving a level of physical exertion. For example, the lower the ratio of the two values, the higher the level of fortitude. A "Hero's Heart" may be a cross-activity expression in the intelligent wear system community: which may include users performing extreme activities, such artistic gymnastics, climbing, Parkour, etc., ranking results from such activities (such as in a single Hero chart), and standardizing such exhausting actions and inner peace parameters such as by a combined and elaborated "Hero" algorithm.

FIG. 6D shows a "Meditation" garment system configured to provide a feelings-driven melody by detecting the user's psychological and physiological status. The "Meditation" garment includes ECG sensors, respiration sensors, strain gauges, and touch points as described above, on the "Meditation" shirt. The meditation garment further includes a sensor on a first sleeve of the garment and a sensor on a second sleeve of the garment. "Meditation" garment further includes pants to The "Meditation" garment system further includes a "Meditation" cap with an electroencephalogram sensor (EEG) configured to detect brain waves. As described above, the body sensor signals from the sensors are sent to the sensor module. The sensor module processes the data and provides feedback. As described above, the sensor module is configured to provide feedback such as a feelings-driven melody. The feedback may be used as a training technique. A user may be taught to improve their health and/or performance by becoming more aware of, and using biometric signals from, their body. A user may become actively involved in controlling their inner status. Any type of sensor may be used for an inner checkup. In some embodiments, a wide variety of sensors work in unison for a complete inner checkup. Such sensors may include but are not limited to those described herein or as known in art. In particular, such sensors may include: heart rate monitor (to measure heart rate variability); galvanic response sensor (to measure the electrical conductance of the skin and the moisture level; which may be taken as indication of psychological and physiological arousal); skin temperature sensor (which may be taken as indication of cognitive and emotional states); perspiration sensor (which may be taken to measure relaxation vs. emotional stress and anxiety); electroencephalography (EEG) (which may be taken to measure addiction, anxiety disorders (including posttraumatic stress disorder, obsessive-compulsive disorder, worry), attention deficit disorder (ADD), attention deficit hyperactivity disorder (ADHD), depression, learning disability, migraine, and generalized seizures); blood pressure sensor (which may be taken to measure and monitor level of relaxation vs. stress and variations); electromyography (EMG) (which may be taken to measure muscle tension and/or muscle relaxation vs. neuro-muscular hypertension and overexertion); breathing rate sensor (to measure relaxation vs. anxiety (relaxation may be taken to correspond so to a lower respiratory rate (slow and deep breathing)); anxiety may be taken to correspond to a higher respiratory rate (rapid and shallow breathing), etc.

In some embodiments, a significant role may be given to skin conductance which increases when a person is more aroused (e.g., engaged, excited, stressed), while it tends to stay low or drop when a person is less aroused (bored, calm, disengaged).

In some embodiments, based on the tracked sensor data, the an intelligent wear module (sensor manager) may simultaneously convert the user biometric output (e.g., physiological signals) into a musical feedback whose quality (e.g. brightness or depression of the sound, major or minor key, rhythm, speed) changes based on the user's physiological and/or psychological changes.

Using feedback as described herein, a user may be able to learn how to rely on the power of their mind to improve their overall health and live better.

Another aspect of the invention includes an intelligent wear system configured to provide communication between a plurality of individuals, including an intelligent wear garment item user. Instead of, or in addition to an intelligent garment system providing feedback, such as haptic feedback or musical expression to an individual, an intelligent garment system may provide communication between a plurality of individuals. In one embodiment, an intelligent wear system may provide a communication based on an intelligent wear garment user's performance. A system may be configured for communicating physiological data from a user (rather than or in addition to communicating a subjective interpretation based on the physiological data). For example, a system may be configured to allow a user to set a personal goal, and (automatically) communicate to another individual when they hit their goal (e.g. a threshold). Such a communication made be sent to a friend or to a gateway such as a computer or website. Such a process may be controlled though an intelligent wear application such as on an intelligent wear module. An intelligent wear system may also or instead be configured to allow an intelligent wear user to share an audio expression (a music expression) or a video expression based on their body such as through dance, other movements and/or postures. Such an expression may be created by the intelligent wear system (e.g. intelligent wear module). For example, an application on an intelligent wear module can measure (interpret) a user's performance, such a Parkour user's performance, while he is developing or training for improved (increased) strength, endurance and balance though a course, such as a Parkour course. Such a user may set a goal they want to achieve, and the intelligent wear system may notify a user's friend when the goal is hit. There are common parameters that may help measuring the execution of the moves. Such a goal may be any of the various types of Parkour moves, such as, for example, maximum gravitational defiance, rotational speed, movement speed, time spent off feet, time spent upside down, jump elevation, distance travelled in the air, time of balance in an extreme environments, etc.

In some embodiments, an intelligent wear system may provide a communication to an individual or to a location available to an individual or to a group based on an intelligent wear garment user's cultural behavior and/or gestures. A cultural behavior and/or gesture may be translated into an intelligent input on an intelligent wear garment item. Such a cultural behavior and/or gesture can be adapted to create a cultural expression that may initiate a specific command or an innovative means of communication. Such a command or means of communication may be customizable (such as in an application by the intelligent wear item user). For example, hitting a fist on one's heart twice and then making the peace sign may be an African-American sign for peace out, I love you. Such a communication may have roots in American Sign Language, meaning "I give you my heart and peace". A basketball player uses this kind of gesture when they score. Applied, for example, to an interactive sensor (touch point) on an intelligent wear shirt, the intelligent wear system may be configured to activate the delivery of a message to all the player's fans (e.g. automatically and/or instantaneously) in response to the player making the gesture. 'I love you' may then appear on a social network, available for close and far fans. In another example, a somersault performed by a soccer player after he scores a goal may be recognized by intelligent sensors (e.g. accelerometers) on an intelligent wear garment and may activate the delivery of a player message such as to fans, friends, offspring, a spouse, etc. In another example, an intelligent wear garment system may detect using intelligent sensors such as accelerometers on intelligent wear items such as shirts, a gesture, such as a handshake, high-five, fist bump, chest bump, hug, etc. between the intelligent wear shirt users. A gesture-based command in combination with a communication protocol (e.g. a standard communication protocol) may result in alternative social communication systems based on recognized cultural behaviors between intelligent wear users. For example a gesture (such as those described above) in combination with NFC, Bluetooth, Wi-Fi may initiate data sharing. The proximity of the items (e.g. shirts) may activate the immediate (e.g. automatic) sharing of personal data or other type of content previously set by the user(s) between the users in response to the gesture. Such data or content may go from a first user to a second user and may also go from the second user to the first user. Such data or content may include personal data such as business card information, content sharing such as music, expressions, etc. and/or friendship functions such as "add friend" or "follow user" features.

In some embodiments, an intelligent wear system may be configured to provide a communication to an individual (or to a location available to an individual or to a group) based on an intelligent wear garment user's vocal communication (voice). Such a communication may comprise providing immediate connectivity and message delivery. An intelligent wear user may for example, activate (or receive) a call, send (or receive) an SMS, send (or receive) an email, and/or share an instant messages through an intelligent wear platform and a social network (such as Facebook, Twitter, etc.) even while engaging in an activity such as playing tennis, climbing a mountain, running, riding a bicycle, driving a car, etc. Such a communication may be activated via voice recognition and a voice-to-text feature may allow instant creation and sharing of messages on social networks even without typing. (In addition to providing a hands-free option for a user engaged in an activity, a voice recognition may be faster than text message. Voice recognition is considered eight times faster than text messaging).

In some embodiments, an intelligent wear system may be configured to leave audio content and/or other messages in a specific location. In some embodiments, an intelligent wear system may be configured to be notified that audio content and/or other messages are available to an intelligent wear system user as they enter a designated area. Such audio content and/or messages may be from an intelligent wear user to others, such as 'a friend to friends', "an intelligent wear system application or website to users', 'third parties to users', 'users to intelligent wear system application or website', etc. An intelligent wear system user may be notified through any means, such as audio, haptic, and/or visual notification as they enter a designated area. For example, one or more fans can share a team anthem with other fans at a stadium to play the anthem simultaneously (such as via a synchronization feature, or to synchronize wave-type). In another example, street dancers using an intelligent wear system can exchange musical bases for their performances based on locations, such as hip-hop bases in which a group of break dancers may perform.

In some embodiments, an intelligent wear system (e.g. an Expressions Crowd-Sourcing open platform such as an expression crowd-sourcing open platform) may offer an advanced social tool for crowd-sourcing and sharing. Using such a social tool, a user may be able to upload/download a library of expressions, such as in the form of biometric formulas (software) and/or videos and/or supported by an audio input. Such an expression may be, but is not limited to, a training session (such as, e.g., for Pilates, tennis yoga, etc.), a cultural dance, a body alignment instruction, an extreme body posture instruction, an exercise, other body moves, etc. A formula may be used for creating an expression or a library of expressions. A formula may be built for creating such an expression or a library of expressions. For example, a plurality of sensors may track an intelligent wear user's execution of an expression such as via a motion detection system. Such a system may automatically register the movements and convert them into a pattern or function ("a formula" or a "built formula") that retains relevant information about the movement (e.g. balance, positioning, sequence, speed, etc.) A formula may be sharable with another intelligent wear system user. Such a formula may be able to adapt to different body shapes and physiological status, and may include preserving proportions in postures, movement extension, elevation based on user's height, etc. A user may obtain (e.g. download) a built formula expression and use it, such as learning to execute the movements (e.g. repeatedly, such as very accurately). A formula (e.g. an expression formula) may include training inputs such as haptic feedback that can be activated during the user's execution of the movements. Sensors on the user's intelligent wear system may gain data from the user's body (e.g. movements) and send them to the module. Such a module may (immediately) elaborate a response and provide the intelligent wear/formula user feedback based on the formula. For example, a vibrating effect may act on a portion of the user's body that are OFF the proper alignment or zone. As the user adjusts the position and enters the proper alignment or the right zone, an actuator may stop the vibration to indicate that the user is engaging in the correct movement.

Depending on the type of activity, an intelligent wear system can also guide dynamic expressions through haptic activators that suggest particular movements. Such an expression may work in conjunction with (e.g. be controllable by a vocal command).

Such a training program may also work real-time in the presence of an instructor, who may wear a 'leading' intelligent garment item that may provide guidelines to a class of students wearing 'receiver' intelligent wear items. Such an instruction may enhance the teaching process and act to create synchronized movements such as in aerobics, step, Zumba, Pilates, etc. (for example, right leg up, right arm down, etc.).

Another aspect of the invention comprises a flexible garment configured to continuously conform to a user's body when the garment is worn by the user, the garment comprising: a body sensor on the garment configured to sense one of a user's position, a user's movement, and a user's physiological status and thereby generate a body sensor signal; a conductive trace on the garment, connected with the sensor and configured to communicate the body sensor signal from the body sensor to a sensor module for analysis; and an interactive sensor on the garment configured to transmit an interactive sensor signal to the sensor module when the user's hand activates the interactive sensor wherein the sensor module is configured to control an audio output and/or a visual output in response to the interactive sensor signal.

In some embodiments, the flexible garment comprises a compressive material. In some embodiments the flexible garment is configured to expand and contract. In some embodiments, a body sensor on the flexible garment is configured to be in electrical contact with the user's skin.

One aspect of the invention provides a method of washing a conformable garment comprising a plurality of sensors, the method comprising: placing a conformable garment comprising a plurality of body sensors and a plurality of interactive sensors attached thereto into an aqueous solution comprising a cleaning agent; and moving the garment through the aqueous solution and cleaning agent; separating the conformable garment from the aqueous solution and cleaning agent; and drying the conformable garment.

A conformable garment comprising a plurality of sensors, such as the garments shown in FIGS. 6A-D, may comprise a body sensor, an interactive sensor (touch point), a conductive trace and/or other features configured to be sufficiently water and soap resistant so that the garment may be immersed in an aqueous solution. Such a garment may be washed using standard washing methods and machines using an aqueous solution (water) and a cleaning agent such as a detergent. Such a garment may be configured to withstand additional solutions such as a fabric softener, a cleaning solution comprising an enzyme configured to clean a garment, or other known cleaning methods. A conformable garment may be sufficiently dryer resistant so that exposure of the garment to a dryer, such as a conventional clothes dryer, does not damage the sensors, touch points, and/or other features. In one example a sensor, a touch point, and/or other features may be sufficiently sealed to prevent water entry into electrically conductive or other water-sensitive portions. In another example, an electrically conductive portion of a sensor, a touch point, and/or other features may be configured to recover after being exposed to a washing cycle (and a drying cycle). In some embodiments, a conformable garment comprising a plurality of sensors, such as the garments shown in FIGS. 6A-D, may comprise a body sensor, an interactive sensor (touch point), a conductive trace and/or other features configured to be sufficiently chemical resistant so that the garment may be immersed in a dry-cleaning solution. (e.g., may be resistant to damage from a dry cleaning process or exposure to a dry cleaning reagent.

A garment, such as a shirt, may have a front and a back and may have a pocket (e.g. in the back of the shirt) and the pocket may be configured to hold a sensor module on the back of the shirt.

One aspect of the invention provides a wearable communications device comprising: a collar configured to wrap partially around a user's neck and to hold a shape and comprising at least one of a speaker and a microphone; and a base region connected with the collar and configured to provide electrical communication between a sensor module and the collar wherein the sensor module is configured to connect with a conformable garment comprising a plurality of body sensors.

FIG. 7 shows a wearable communication device 172 configured to be controllable by a sensor module, such as to communicate an audio output signal from the sensor module. The audio output signal may comprise a signal to play music, stop playing music, turn on or turn off a microphone, or control another audio output. Wearable communication device 172 has a collar 170 with a first collar arm 171 and a second collar arm 172. Wearable communication device 172 has a sensor module connector 174 is configured to connect with sensor module 176. Wearable communication device 172 and/or collar 170 and/or first collar arm 171 and/or second collar arm 172 (and any other wearable communication device components or parts) may be sufficient rigid so that a user may grab such a component or part and use it to place wearable communication device 172 in connection with sensor module 176. Wearable communication device 172 and/or collar 170 may be sufficient rigid so that a user may grab the base region or collar and use it to place connected sensor module 176 into a pocket 178 on the back of an intelligent garment. Such a module may include one or more cables configured to electrically connect with the collar (such as on a flap or board). A connection between a module and collar may be easily made, such as by a single jack or other connector. Such a jack may be placed on the higher side of the collar, such that it allows the neck to bend backwards with little/no interferences. Earphones 180 (earbuds) may be attached to the base region or collar and speakers and/or a microphone may be connected with the collar (or earphones). In a particular embodiment, a wearable communication device may include 2 loudspeakers, a microphone, a phone jack, and 6 switches (power on/off, Wi-Fi on/off, Bluetooth on/off, microphone on/off, speaker volume, and microphone volume).

In some embodiments of a flexible garment, a conductive trace (for example to connect a body sensor or touch point to a sensor module) is configured to conform to the user's body when the flexible garment is worn by the user. In some embodiments of a flexible garment, the conductive trace is on a surface of the garment.

FIGS. 8A-8B and FIGS. 9A-B shows the front side, and back side, respectively of a flexible intelligent wear garment configured to output an output signal to a phone, computer, the cloud, etc. as described elsewhere in this application. Body sensor 190a, such as a heart rate sensor is connected by flexible trace 192 to sensor module 196 on the back of the shirt. A second body sensor 190b, such as another heart rate sensor, may also be connected (such as from the opposite direction). FIGS. 9A-B show a first respiratory sensor 198 on a garment and configured to wrap (e.g. annularly) around a user's rib cage when on the garment is on a user. FIG. 9B also shows a second respiratory sensor 200 on a garment and configured to wrap (e.g. annularly) around a user's abdomen when the garment is on a user. First respiratory sensor 198 and second respiratory sensor 200 are connected with sensor module 196 with a conductive media. In some embodiments, a garment has a first axis and a second axis perpendicular to the first axis, and a trace is configured to substantially follow the first axis (and not follow the second axis). Manufacturing a garment with an annular trace (e.g. one that is configured to wrap around a garment) may be challenging. For example, it may be difficult to manufacture a 3-dimensional trace onto a 2-dimensional substrate (which trace would be electrically testable prior to final garment assembly). It may be difficult to transfer a 3-dimensional annular sensor from a substrate to a garment. In some embodiments, a method of manufacturing an intelligent wear garment with a body sensor, such as a respiratory body sensor, may include placing a first portion of a sensor on a garment and placing a second portion of the sensor on the garment such that the second portion overlaps with the first portion. In some embodiments, one or both portions may be electrically tested prior to final garment assembly. In some embodiments, an electrical trace may be manufactured inside a tube or a cutaway tube prior to garment assembly. Such a tube may be substantially straight or may be substantially curved. In some embodiments, a respiratory sensor may comprise a pattern configured to measure a change, such as a zigzag pattern on a front of a garment. One or two or more than two such sensors may be present on a garment, such as over the rib cage area and over the abdominal area when the garment is being worn.

Respiratory measurements: External measurement of chest wall surface motion can also provide a useful way to estimate pulmonary ventilation and to circumvent the potential problem that may occur when pulmonary ventilation is assessed by integrating the airflow measured at the airway opening by a pneumotachograph. Variations in temperature, humidity, pressure, viscosity and density of gas determine integration drift so that changes in absolute lung volume may not be accurately recorded. Other methods, such rebreathing from a spirometer or a bag-in-box system, may be difficult to apply for prolonged time periods, while collecting expired gas in a large spirometer or gas tight bag (e.g., a Douglas bag) may cause problems due to the gasometer, which may require intermittent calibration over time and does not allow a breath-by-breath analysis.

In the last decades, a number of devices and methods have been developed in order to allow measurements of rib cage and abdominal motion. In parallel, several attempts have been made to define calibration methods able to estimate volume changes of the single lung compartments, of the entire chest wall, and of the lung from measurements from the diameters, circumferences or cross sectional areas, such as the iso-volume method, changing posture (Chadha T S, Watson H, Birch S et al. Validation of respiratory inductive plethysmography using different calibration procedures. Am Rev Respir Dis 125:644, 1982), and the natural breathing method (Sackner, M. A., H. Watson, A. S. Belsito, D. Feinerman, M. Suarez, G. Gonzalez, F. Bizousky, and B. Krieger. Calibration of respiratory inductance plethysmography during natural breathing. J. Appl. Physiol. 66: 410-420, 1989). The validity of the calibration coefficients obtained experimentally to convert one or two dimensions to volume is generally limited to the estimation of tidal volume under conditions matched to those during which the calibration was performed (Zimmerman, P. V., S. J. Connellan, H. C. Middleton, M. V. Tabona, M. D. Goldman, and N. Pride. Postural changes in rib cage and abdominal volume-motion coefficients and their effect on the calibration of a respiratory-inductive plethysmograph. Am. Rev. Respir. Dis. 127: 209-214, 1983).

Measurement of diameters: Magnetometers were the first instruments developed in the late sixties to measure changing diameters during breathing (K. Konno and J. Mead, "Measurement of the separate volume changes of the rib cage and abdomen during breathing," J. Appl. Physiol. 22(3):407-422, 1967). Two pairs of coils were usually placed on the front and on the back of the rib cage and abdomen; one coil was used as a generator and the other ('sensing coil') was used as a receiver of magnetic field. Since the output voltage of the sensing coil is proportional to the intensity of the magnetic field, which varies proportionally with the cube of the distance separating the transmitter and the receiver, a magnetometer is able to record changes in the antero-posterior diameters of the chest wall. This nonlinear relationship between voltage and distance, however, requires accurate and frequent calibrations. To calibrate the device in order to measure tidal volume and to separate the rib cage and abdominal components, one approach requires iso-volume maneuvers to be performed according to the technique of Konno and Mead (K. Konno and J. Mead, "Measurement of the separate volume changes of the rib cage and abdomen during breathing." J. Appl. Physiol. 22(3):407-422, 1967). Another approach assumes that spontaneous breathing and its normal variation is sufficient to calibrate the device, allowing this technique to be applied also with non-collaborating subjects (Sackner, M. A., H. Watson, A. S. Belsito, D. Feinerman, M. Suarez, G. Gonzalez, F. Bizousky, and B. Krieger. Calibration of respiratory inductance plethysmography during natural breathing. J. Appl. Physiol. 66: 410-420, 1989). In addition, the magnetic field recorded by the sensing coil can be influenced by metallic objects in the surroundings and is therefore difficult to use in certain settings, such as a hospital setting.

An alternative approach which is commercially available, particularly for monitoring respiration in infants, is to measure variations of chest diameters through measurements of transthoracic electrical impedance variations (V. Gramse, A. De Groote and M. Paiva. Novel Concept for a Noninvasive Cardiopulmonary Monitor for infants: A Pair of Pajamas with an Integrated Sensor Module. Annals of Biomedical Engineering, Vol. 31, pp. 152-158, 2003). A small amplitude, high-frequency current is applied through a pair of electrodes and the resulting voltage is demodulated to obtain impedance measurements. Some advantages of this technique are that the electrodes are relatively small, mechanically stable and inexpensive, and can be used to simultaneously record the ECG. However, such electrodes often cause skin irritation in infants and cardiac artifacts are difficult to be separated from a respiratory signal.

Measurement of circumference or cross-sectional areas: Numerous devices based on sensing belts positioned on the rib cage and abdomen or wearable garments embedding different kinds of sensors have been proposed as systems for breathing detection based on chest wall surface kinematics. Changes in the circumference or in the cross-sectional area are then usually used to estimate tidal volume and relative rib cage and abdominal contributions to tidal volume and thoraco-abdominal asynchronies. Various sensor technologies can be used in different sensing belts. Technologies include mechanical transducers, such as capacitive elastic strain gauges (V. Gramse, A. De Groote and M. Paiva. Novel Concept for a Noninvasive Cardiopulmonary Monitor for Infants: A Pair of Pajamas with an Integrated Sensor Module. Annals of Biomedical Engineering, Vol. 31, pp. 152-158, 2003 and piezoelectric films (Pennock 1990), ultrasound waves in a rubber tube ( ) (Lafortuna and Passerini 1995) and optical sensors (fiber optics) (. Optical fibers have been recently proposed as an alternative method to detect thoracic and abdominal circumferences in non-invasive respiratory monitoring systems A. Babchenko, B. Khanokh, Y. Shomer, and M. Nitzan, "Fiber optic sensor for the measurement of respiratory chest circumference changes," J. Biomed. Opt. 4(2), 224-229, 1999) (D'Angelo et al. 2008). The macro-bending loss effect in optical fibers arranged in figure-of-eight loops have the advantages of increased linearity of response, higher resolution and sensitivity and lower mechanical resistance and hysteresis. This approach enables measurement of respiratory and cardiac function using the same transducing fiber.

Respiratory Inductive Plethysmography (RIP): Respiratory inductive plethysmography allows measurement of changes of rib cage and abdominal cross sectional areas by two coils of insulated wire sewn inside 10-cm-wide elastic bands which are usually placed below the axillary line and above the umbilicus. The two wires are connected to an oscillator module. The principle of RIP relies on the output frequency-modulated signals, which are proportional to variation in the self-inductance of the coil. The self-inductance of the coil is in turn proportional to the cross-sectional area enclosed by the coil, and therefore it varies as the rib cage and the abdomen expand and contract during respiration. The oscillatory signals are then sent to a demodulator unit that provides the output signals (Milledge, J. S., Stott, F. D. Inductive plethysmography—a new respiratory transducer. J Physiol (Fond) 267:4, 1977.) (25) (26). Recently, RIP has been embedded in a multi-function wearable device consisting of a Lycra® garment for continuous ambulatory monitoring of respiration. The system also incorporates ECG and a tri-axial accelerometer (Heilman, K. J., Porges, S. W., 2007. Accuracy of the LifeShirt (VivoMetrics) in the detection of cardiac rhythms. Biol. Psychol. 75, 300-305.).

Measurement of respiratory volumes: Optical systems. A variety of optical techniques using multiple video cameras combined with either light projected on the chest surface or reflective markers positioned on it have been proposed to track the changing shape of the thoraco-abdominal surface during breathing and from this to calculate the enclosed volume. Optical methods based on structured light to analyze chest wall movement during breathing have been pioneered by Peacock et al (refs), who firstly introduced a technique for mapping the size and shape of the thoraco-abdominal wall (Peacock A., Gourlay A. and Denison D. Optical measurement of the change in trunk volume with breathing. Bull. Fur. Physiopath. Resp. 21: 125-129, 1985; Peacock, A. J., Morgan M. D. L., Gourlay, S., Tourton, C. and Denison, D. M. Optical mapping of the thoraco-abdominal wall. Thorax. 39: 93-100, 1984). This was achieved by projecting a grid on sheets of light creating contour lines on the visible surface of the torso, recording them by still or video camera and reconstructing the shape from the digital information. Knowing the relative positions of the cameras and the projector permits the reconstruction of three dimensional data concerning the thoraco-abdominal wall and methods for calculating and cross-sections, surface areas and volumes. In 1986 Saumarez described a similar system based on a projector shining approximately vertical stripes on the torso and television cameras scanning with horizontal lines the body. These systems, however, remained confined in few research applications, not including exercise, because of the difficult use and the complexity of the procedures of data processing. More recent advances in using structured light to measure surface topography are nowadays opening new perspectives for the development of more automatic procedures to process the data and to obtain chest wall surface movement and volume variations during breathing. These include color structured light systems (Huijun Chen et al. Color structured light system of chest wall motion measurement for respiratory volume evaluation. Journal of Biomedical Optics 15(2), 026013, March/April 2010), in which the projection of an encoded color pattern on the subject's torso and few active markers attached to the trunk allows accurate measurements of 3-D topographic changes of the chest wall to be obtained and from these total and compartmental measurements of volume variations with a good level of automation in the data processing.

Opto-electronic plethysmography: Opto-electronic plethysmography is based on a motion analyzer that measures the volume of the chest wall and its compartments by means of retro-reflective markers placed on the trunk of the subject in selected anatomical reference sites of the rib cage and the abdomen. Each camera is equipped with an illuminator (infrared light-emitting diodes) that determines a high contrast between the reflective marker and the rest of the scene on the recorded images thus allowing the fully automatic recognition of the markers. If each marker is seen by two or more TV cameras, its position (defined by the three dimensional coordinates) can be calculated by stereo-photogrammetry. The markers are positioned on approximately horizontal rows at the levels of the clavicular line, the manubrio-sternal joint, the nipples, the xiphoid process, the lower costal margin, the umbilicus and the anterior superior iliac crest. Surface landmarks for the vertical lines are the midlines, both anterior and posterior axillary lines, the midpoint of the interval between the midline and the anterior axillary line, the midpoint of the interval between the midline and the posterior axillary line, and the midaxillary lines. Extra markers are added bilaterally at the midpoint between the xiphoid and the most lateral portion of the 10th rib and in corresponding posterior positions.

From 3D marker coordinates measured by OEP, kinematics of the chest wall can be studied considering different parameters at different rib cage and abdominal levels, such as distances (e.g., anteroposterior or medio-lateral diameters), perimeters (by summing the 3D distances of all the contiguous markers placed at a given level) and cross-sectional areas (by summing the areas of the triangles each formed by two contiguous markers and the baricenter of all the markers positioned at a given level). OEP allows the measurement of the volume of any parts of the trunk by defining closed surfaces with the same method that is used for the calculation of the chest wall volume. The geometrical models of the compartments that have been developed for OEP volume measurements follow the three-compartment model (i.e. RCp, RCa and AB) (Ferrigno G, Carnevali P, Aliverti A, Molteni F, Beulke G and Pedotti A. Three-dimensional Optical Analysis of Chest Wall Motion. J Appl Physiol 77(3): 1224-1231, 1994; Cala S J, Kenyon C, Ferrigno G, Carnevali P, Aliverti A, Pedotti A, Macklem P T and Rochester D F. Chest wall and lung volume estimation by optical reflectance motion analysis. J Appl Physiol 81(6): 2680-2689, 1996). The rib cage is separated from the abdomen by a line that follows the lower costal margin. The subdivision of the rib cage into RCp and RCa is defined by the transverse section at the level of the xiphoid (Kenyon C M, Cala S J, Yan S, Aliverti A, Scano G, Duranti R, Pedotti A and Macklem PT. Rib Cage Mechanics during Quiet Breathing and Exercise in Humans. J Appl Physiol 83(4): 1242-1255, 1997). Precisely the surface that encloses RCp extends from the clavicles to a line extending transversely at the level of the xiphisternum, while RCa extends from this line to the lower costal margin. AB extends caudally from the lower costal margin to the level of the anterior superior iliac crest (Cala S J, Kenyon C. Ferrigno G, Carnevali P, Aliverti A, Pedotti A, Macklem P T and Rochester D E.

Chest wall and lung volume estimation by optical reflectance motion analysis. J Appl Physiol 81(6): 2680-2689, 1996).

A closed surface of the chest wall is identified by connecting the points to form a mesh of triangles. In the case of the seated and standing positions the whole trunk is visible and the volume of the chest wall, internal to the closed surface, can be computed by means of the Gauss' theorem (Cala S J, Kenyon C, Ferrigno G, Carnevali P, Aliverti A, Pedotti A, Macklem P T and Rochester D F. Chest wall and lung volume estimation by optical reflectance motion analysis. J Appl Physiol 81(6): 2680-2689, 1996)). When the subject lies in a position with his/her back supported, the posterior part of the trunk is defined by a reference plane defined by the co-ordinates of the markers positioned laterally on the trunk. Aliverti A, R. Dellacà, P. Pelosi, D. Chiumello, L. Gattinoni and A. Pedotti. Compartmental analysis of breathing in the supine and prone positions by Opto-Electronic Plethysmography. Ann Biomed Eng 29:60-70, 2001) (Aliverti et al., 2001)

FIGS. 9A-B show two stretchable respiratory measurement rings at the level of the rib cage and the abdomen at the torso/trunk useful for measuring respiratory volume of user. A cross-sectional area of a ring (and the electrical resistance of the ring) changes as an individual breathes. Such a change in resistance may be measured and used for determining a change in circumference. Such a change may be used for determining a respiratory volume for an individual. Such rings may be made, for example, by a conductive media. One step in obtaining a respiratory volume from an individual may be calibrating the signals obtained from the rib cage.

A flexible garment with a flexible trace may be configured to conform continuously to a user's body. FIG. 8C shows a flexible trace, such as the one shown in FIGS. 8A-B, with a silver conductive core surrounded by an outer insulating layer. A core of a trace may contain any type of conductive material and an outer layer may contain any type of insulating material as along as the resulting trace is able to carry (electrical) signals and/or power. A trace may be a flexible trace or a conformable trace (or both, or neither). Also described herein are conductive ink patterns having a high degree of stretchability that may be used.

One aspect of the invention provides a method of manufacturing a flexible compressive garment comprising: placing a first insulating fluid media onto a substrate, the fluid comprising an adhesive; placing a conductive material on the first insulating fluid media to thereby create a conductive material electrical trace; solidifying the first insulating fluid media to create a first flexible insulator region and thereby generate a flexible transfer comprising a conductive material electrical trace wherein the transfer is configured to be removed intact from the substrate; removing the transfer from the substrate; placing the transfer on a flexible compressive garment; attaching the transfer to the flexible garment; electrically connecting the transfer to a sensor on the flexible garment wherein the transfer is configured to be connected with a sensor module. Other examples are provided in greater detail below.

A conductive trace may be made from a conductive media, for example, from one or more of a conductive liquid having high resistance, from an insulating media embedding a layer of conductive material, or from an insulating media embedding a conductive wire or a conductive cable. Use of such an insulating media may allow a conductive trace to be, for example, more flexible. As described herein, a conductive ink trace may, in particular, be a conductive ink pattern that is formed from an insulative adhesive and a conductive ink; this type of conductive ink pattern typically includes a gradient or intermediate region between the conducive ink and the adhesive and may have superior stretchability relative to other types of conductive traces, including insulated wires.

In some embodiments, a conductive trace may be made from a conductive media with high resistance. Such a conductive media with high resistance may be made mixture of a media and ultrafine conductive particles (such as copper particles). Any concentration of particles may be used. Such a conductive trace may allow a conductivity (resistivity) of the order or hundreds of ohms/square. Such a conductive trace may have very good extensibility and softness. Such a conductive media with high resistance may be used, for example, for forming an EKG electrode such as in form of plates (such as less than 3 cm, 3-5 cm, or greater than 5 cm diameter) printed in the inner part of a flexible (compression) top (shirt) in correspondence of the thorax for heart rate measurements. Such a conductive media with high resistance may be used for creating a spirals to go around the chest and the abdomen or in the linear zigzag pattern on the chest and the abdomen of a flexible top (shirt) to implement a strain gauges printed on the outer or inner part of the compression shirt to measure the variations of circumference of chest/abdomen during breathing. Such a conductive media with high resistance may be used to create a linear strain gauge, such as one printed along a sleeve of a garment or a leg of a garment and configured to measure the flexion of an arm or a leg. Such a conductive media with high resistance may be used to implement an electrode in the form of one or more plates. (1-2 cm diameter) Such a plate may be placed in the inner part of a compression shirt. Such a plate may be made in correspondence of the armholes and may be configured for performing skin conductance measurements. Such a plate may be less than 1 cm in diameter, from 1 cm to 2 cm in diameter, more than 2 cm to 3 cm in diameter, or more than 3 cm in diameter. Such a conductive media with high resistance may be used for implementing a touch points in form of plates (e.g. apposed half circles of 3-5 cm diameter or comb-like patterns) placed in multiple sites on the outer part of the compression shirt. A good connection between a conductive media (ink) with high resistance and other electronics may be made by embedding a wire or a cable having multiple wires between two layers of a conductive media (ink).

A conductive trace made from a conductive media may be made, for example from an insulating media embedding a layer of conductive material.

FIGS. 10A-10B shows a method of manufacturing an insulating media by embedding a layer of a conductive material. Such a media may be made from (at least) three layers: a first layer 1001 may be made from an insulating media (e.g., adhesive, insulating "ink", etc.), a second layer 1003 may be made from a conductive media, which may comprise conductive particles or a mixture of insulating media and conductive particles (such as ultrafine copper particles at very high concentration) and a third layer 1005 made from an insulating media (e.g., resin, adhesive, "ink") which may comprise the same or a different media as the first layer 1001. These three layers may be deposited during three consecutive phases during the printing process. A state of any or all of the layers may be changed during the manufacturing. For example, any or all of the layers, such as the first insulating layer, the second conductive layer, or the third insulating layer (or any additional layers) may be made by solidifying a flexible media, which may include solidifying an adhesive, a glue, a polymer, etc. Solidifying a media may generate a conformable transfer. The inner layer may allow a conductivity of the order of $10^3$ ohms/square and may be extensible. Such a media may be used to conduct electrical current to/from a media-based (ink-based) sensor or electrodes (as described above) and/or to allow easy connections with ink-based sensors or electrodes (as described above). A conductive trace made from a conductive media may be made by embedding a conductive wire or a conductive cable in an insulating media, as illustrated in FIG. 10B.

A conductive trace may be made by incorporating a conductive material such into a polyimide material (e.g. Kapton® film from DuPont), which may be a thin, flexible material. Such conductive traces may be incorporated into a plurality of layers of conductive media (conductive ink). A Kapton® based conductive trace may be manufactured as a "transfer sheet" which may, for example, subsequently be printed onto a shirt to create an intelligent shirt. A Kapton®-based trace may be manufactured by the steps of providing a substrate; depositing a first set of conductive ink layers on the substrate; depositing a set of polyimide (Kapton®) traces onto the first set of conductive ink layers (e.g. manually, by means of a specifically designed template to facilitate the process, etc.); depositing a series of conductive ink layers onto the polyimide layer (Kapton® (e.g. by serigraphy); and depositing an adhesive material onto the conductive ink layers. Additional steps may include the steps of depositing one or more other conductive media (conductive ink) onto the substrate, depositing one or more sensors onto the substrate, depositing one or more other conductive media (conductive ink) onto a conductive ink layer, depositing one or more sensors onto a conductive ink layer, depositing one or more other conductive media (conductive ink) onto a polyimide (Kapton®) layer, and/or depositing one or more sensors onto a polyimide (Kapton®) layer. Such conductive media and/or sensor may be deposited in electrical contact in the Kapton®-based conductive trace (but not as a layer in the trace) or may be deposited as a part or layer within the Kapton®-based conductive trace. Depositing such a conductive media (conductive ink) or sensor may provide the advantage of facilitating the process of transferring onto the shirt a conductive media (conductive ink) body sensor, a conductive media (conductive ink) interactive sensor (touch point), another conductive media (conductive ink) trace, a Kapton®-based conductive trace, a part of a flexible Kapton®-pcb (printed circuit boards) that may hold another sensor (such as an accelerometer). Depositing such a conductive media (conductive ink) or sensor onto a trace and transferring the trace including such conductive media (conductive ink) or sensor may provide the advantage of allowing an electrical signal, a power supply, and/or a ground signal to be brought to/from a sensor, to/from a sensor amplifier, to/from a power supply, and/or to/from part of a conductive ink used as a sensor (e.g. parts of conductive ink in contact with a user's skin and useful for detecting, for example, an ECG signal, an EMG signal, skin conductance, and/or conductive ink used as an interactive sensor (touch point). A trace may be, for example, less than 0.03 mm, between 0.03 to 0.1 mm, between 0.1 mm to 0.3 mm, between 0.3 mm to 0.5 mm, or greater than 0.5 mm in thickness.

In some embodiments, a conductive wire (or thread) or a conductive cable may be embedded in an insulating media (insulating ink) to form a conductive trace. Alternatively or additionally, a conductive thread may be sewn onto the garment. An conductive trace including a wire may comprise three parts (which will be described for simplicity as three layers): a first layer 101 made, e.g., from an insulating ink, a conductive wire 1013 (or a cable comprising multiple conductive wires), and a second layer 1004 made from a second insulating ink (e.g., adhesive, etc.). The second insulating ink may be the same or a different insulating ink as used in the first layer 1001. The steps of the printing process may include: depositing the first insulating layer 1001 onto a print support 1009; positioning the conductive wire/cable onto the first layer; securing the conductive wire/cable on the print support; printing the second insulating layer 1004; and leaving (only) the terminal parts of the wire/cable 1013 outside of the insulating ink. Such a wire/cable allows for conductivity. Such a conductive trace may be manufactured on a first surface 1009 and transferred to a second surface, such as an intelligent wear garment item. Such a transfer may include generating a trace inside a seam, such as on an intelligent wear garment. Such a seam may be made, for example, by welding a trace between two layers of fabric, by bonding the fabric (such as with a chemical or heat). In some embodiments, such a conductive trace may have extensibility. In some embodiments, such a conductive trace may lack extensibility. Such a conductive trace may be used, for example, to bring a sensor condition and/or a power supply to a sensor or to an electrode (e.g. accelerometers, temperature sensor, etc.) so that a sensor and/or power supply may be placed in any location on the shirt (e.g. on the arms); or it may be used to bring an electrical signal (e.g., variable current or voltage) from a sensor or electrode (e.g. an accelerometer, a temperature sensor, etc.) placed in any location on the shirt (e.g. on the arms) to the smart module.

FIG. 10C illustrates one variation of a conductive ink pattern (a conductive ink composite) that has a high degree of extensibility or stretchability. In this example, the conductive ink pattern is applied on a substrate 1039 (which may be a fabric, including a compression fabric forming a compression garment or a transfer substrate), and includes a first layer of electrically insulative elastic adhesive 1021. An outer layer 1025 of conductive ink is separated from the adhesive layer 1021 by an intermediate gradient region 1023 which is a mixture of the conductive ink and the adhesive wherein the concentration of conductive ink decreases from a region closer to the layer of conductive ink 1025 to the layer of elastic adhesive 1025. This gradient region may be referred to as an intermediate layer and may be have a nonhomogeneous mixture/distribution of the electrically conductive ink with the adhesive. An optional outer insulator (e.g., insulating resin, not shown) may also be included over the conductive ink layer. The outer conductive ink may be formed from multiple layers of conductive ink.

Figure 11B:
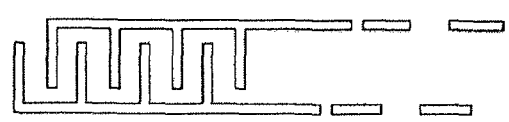
FIGS. 11A-11B show embodiments of interactive sensors useful for sensing in conjunction with a wearable communications platform.
Figure 11A:
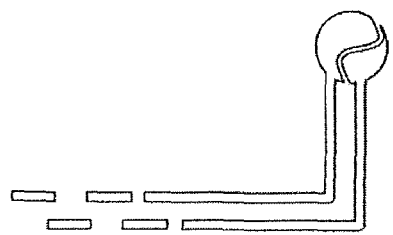

In some embodiments, an intelligent wear garment item may include an interactive sensor system, including an interactive sensor (touch point). Such an interactive sensor may be any type that allows a user to trigger a response, such as by proximity, by a touch, or by a voice command. An interactive sensor may, for example, comprise, a resistive touch point, a direct contact capacitive touch point, or a contactless touch points (through an outer garment). FIGS. 11A-B show touch points. A resistive touch point may be created, for example, by printing a plate of conductive media (ink), such as one which is formed by two apposed non-connected regions such as circles or in a comb-like pattern. By a simultaneous contact of the half-parts, the touch point (formed by the two apposed half parts) is closed to complete an electrical circuit is and a small electrical current is allowed to flow. Such a current may be generated by a voltage generator (such as one internal to a smart module). Such a current may travel from (or to) a smart module to a touch point via as a connecting trace such as one formed by a conductive ink media as described above). A plurality of such touch points may be placed in multiple sites on an intelligent wear garment item, such as on the outer part of the compression shirt. A touch point may include any shape and any size so long as a user is able to interact with it to generate an interactive sensor signal. In some embodiments, an apposed non-connected region may be less than 1 cm, from 1 cm to less than 3 cm, from 3 cm to less than 5 cm, from 5 cm to less than 7 cm, or may be greater than 7 cm in a longest dimension (such as a diameter).

Figure 12B:
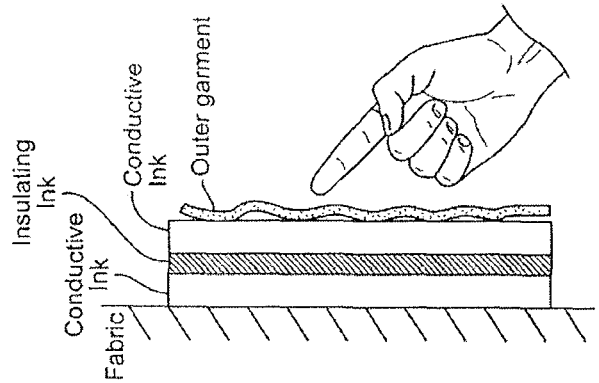
FIGS. 12A-12B show embodiments of interactive sensors, such as for a user to interact with a wearable communications platform.
Figure 12A:
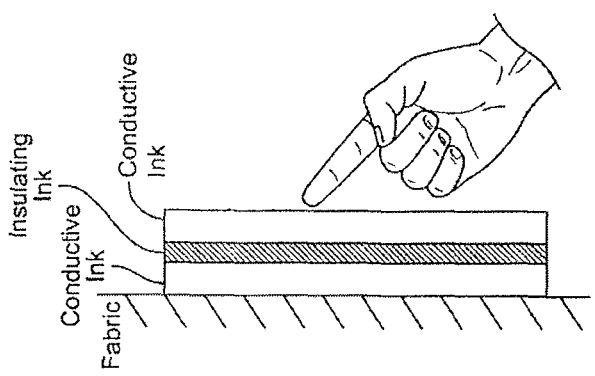

An interactive sensor may comprise a capacitive touch point. Such a capacitive touch points may be created in any way. FIG. 12A shows a direct capacitive touch point and FIG. 12B shows a capacitive touch point that may work by proximity (e.g. a signal that may be travel through an outer garment such as by a finger coming close to the touch point). A capacitive touch point may be created, for example, by printing three layers of material: a first layer comprises a first conductive ink; a second layer comprises an insulating ink; and a third layer comprises a conductive ink, which ink may comprise the same composition or a different composition from the first conductive ink. The first layer may be connected through a conductive ink (such as a conductive material in an insulating ink) to an electrical ground signal. The third layer comprises a 'sensing' region (or plate) for touching. Between the first (receiver) layer and the third (transmitter) layer an electric field is formed. Most of the field is concentrated between these two layers. However, a fringe electric field extends from the transmitter, out of the receiver, and terminates back at the receiver. The field strength at the receiver is measured by proper electronics. The electrical environment changes in response to a stimulus, such as when a human hand/finger invades the fringe field and a portion of the electric field is shunted to ground instead of terminating at the receiver. The resultant decrease in capacitance can be detected by proper electronics.

A peripheral sensor (e.g. a sensor that is not part of the module such as a body sensor or interactive sensor, which sensors may be, for example an ink-based sensor or a traditional sensors, such as one implemented by an integrated circuit soldered on a rigid or flexible printed circuit board (PCBs)) may be connected to the smart module in any way. Such a connection may be, for example, made by a wire and/or a cable. Such a wire and/or cable may be fixed on the garment in any way, such as, for example, by: a) insulating ink embedding a conductive wire or a conductive cable (see description above) or by b) embedding a wire and/or a cable into a welded seam or into a seamless weld (e.g. may be smooth without an obvious join or seam), etc. A method of making a seamless weld with a trace may include overlapping two fabric portions, such as a compression polyester fabric, inserting a trace (e.g. such as a wire or cable) between the overlap and welding the fabric to connect the two fabric portions and thereby contain the trace inside the weld. A weld may be performed in any way, such as using heat to join the two fabric portions.

Figure 13A:
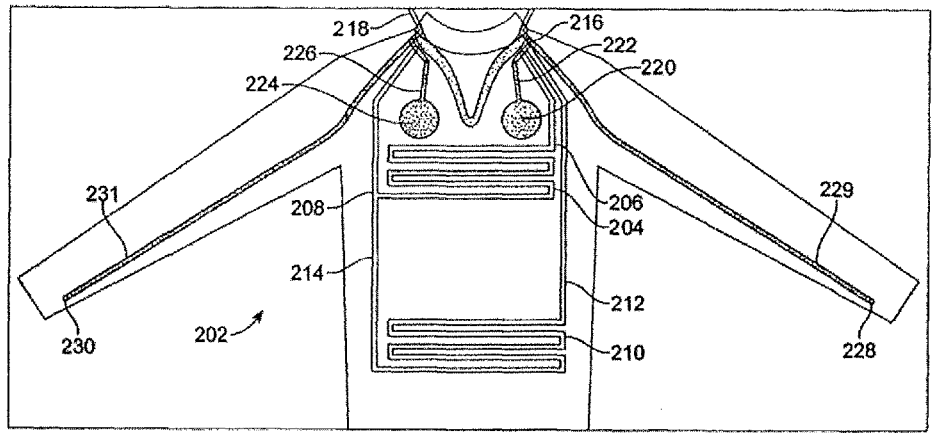
FIGS. 13A-13B show external (outside) and internal (inside) views of an embodiment of a sartorial communications apparatus configured as a shirt with a plurality of sensors and conductive traces.
Figure 13B:
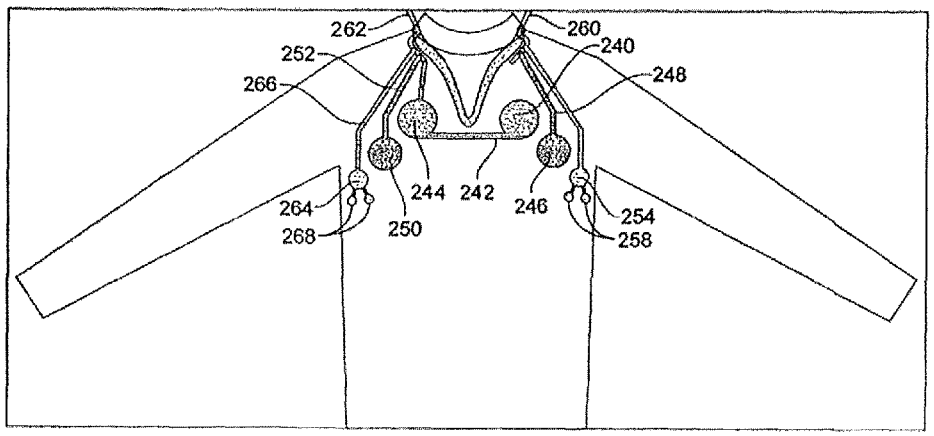

FIGS. 13A-B show an external view (FIG. 13A) of the outside and an internal view (FIG. 13B) of the inside of an embodiment of an intelligent wear shirt 202 with a plurality of body sensors, interactive sensors, connective traces and a collar useful for connecting and communicating between the front and back of the intelligent wear garment or intelligent wear system. Shirt 202 is configured to measure respiration using a two-part sensor system to measure both thoracic respiration using thoracic respiratory sensor 204 and abdominal respiration using abdominal respiratory sensor 206. The respiratory sensors may work such as described elsewhere in the disclosure or as known in the art, and provide sensor data from either or from both sensors to the sensor module. The data generated by the sensors may be integrated (by the sensor manager) to generate the user's total respiratory volume. The respiratory sensors in FIG. 13A utilize common respiratory ground 208 (which may be any sort of trace, such as a conductive trace as described herein) which grounds abdominal respiratory sensor 210 through abdominal respiratory sensor ground 214 to common respiratory ground 208. Such a common ground may reduce the amount of conductive trace material required (and associated material and manufacturing costs). As a conductive trace may be less extendible or less flexible than the extendibility or flexibility of a conformable garment, use of a common ground trace may also increase the garment comfort relative to having separate ground traces. Body signals from thoracic respiratory sensor 204 and abdominal respiratory sensor 210 travel, respectively, via thoracic respiratory sensor connector 212 and abdominal respiratory sensor connector 214 to the top of the shirt in which a connected trace on either side (which may be a Kapton® connected trace running under first interactive sensor external connector 216 and under second interactive sensor external connector 218) carries the signal into the collar, which in turn connects with the sensor module in the back of the shirt. A shirt collar may be more stiff or rigid compared with other shirt material and the shirt may still be very comfortable. For example, shirt collars of street apparel are commonly reinforced in order to render them stiff. A relatively stiff connector trace or series of traces may run more or less circumferentially around the shirt collar which may allow the connector traces to transfer signals from the front to the back of the shirt with minimal or no unwanted shirt stiffness or discomfort. For example, the traces may run through the collar rather than over the shoulder. FIGS. 13A-B also show that a plurality of connector traces may be directed to a shirt collar. In the proximity of the collar, a Kapton® trace may be incorporated into the terminal portion of each or a plurality of such traces (such as by the method described above). The Kapton® traces from the terminal portion of the traces may be successively inserted into the collar and may bring the signals (e.g. all the signals) to the back part of the shirt, where the terminals of the Kapton® traces may be connected to the intelligent communication system/intelligent sensor manager. The collar may also output the traces to the more medial (middle) region of the back of the garment, which puts the traces in a direct vertical path to the sensor module in the back of the shirt. FIGS. 13A-13B also show first and second interactive sensors useful for generating a user-generated signal (such as described elsewhere) such as by a touch or a proximity of a user's hand. Such an interactive sensor may have two layers separated by an insulator. The insulator may be a material special to the sensor or the insulator may be part of the shirt. FIG. 13B shows first external interactive sensor 220 and second external interactive sensor 244 on the outside of the shirt and juxtaposed with first internal interactive sensor 240 and second internal interactive sensor 244 on the inside of shirt 202 respectively. The internal and external sensors are separated by a dielectric material (e.g. an insulator), which in this case is the shirt material which has dielectric properties. Such external and internal sensors may be generated, for example, by separate transfers to the outside and inside of the shirt, respectively. The use of separate transfers to the inside and outside of the shirt may be made for any reason, such as to increase ease of manufacture, reduce material costs, increase flexibility (for example, because the sensors will be thinner), etc. Sensors, such as respiration sensors and interactive sensors, and their connectors may comprise conductive media (conductive ink) for detecting a body signal and for transmitting the signal to the sensor module. A trace, such as a connector trace (or a plurality of different connector traces) may run on a garment in a substantially vertical direction, but not in a horizontal direction, to allow the garment to expand in a garment horizontal plane (e.g. "around" the garment's circumference), but may reduce, inhibit, or prevent garment expansion (extension) in some or all garment vertical planes (e.g. "up and down"). A trace, such as a sensor trace or a connector trace, may run in a horizontal garment plane or a diagonal garment plane in some instances, so that the trace does not substantially interfere with body movement. FIGS. 13A-B shows common ground 208 and thoracic respiratory sensor connector 206 and abdominal respiratory sensor connector 212 travelling diagonally through the shoulder region of the garment. Such an area may require less garment extendibility compared with another region. Alternatively, a diagonal trace may comprise a substantially extendible material. For example, a respiratory sensor and a respiratory connector trace may be substantially flexible and extendible. FIGS. 13A-B also show first external interactive sensor 220 and second external interactive sensor 244 on the outside of the shirt respectively connected with first interactive sensor external connector 216 and second interactive sensor external connector 218 (which may be Kapton® traces as described above). First interactive sensor external connector 216 and second interactive sensor external connector 218 are configured to carry the interactive signals into the collar region, to the back of the collar region, and to the sensor module on the back of the shirt. Similarly, first internal interactive sensor 240 and second internal interactive sensor 244 on the inside of shirt 202 are respectively connected with first interactive sensor internal connector 260 and second interactive sensor external connector 262 (which may be Kapton® traces as described above) which are configured to carry the interactive sensor signals into the collar region, to the back of the collar region, and to the sensor module on the back of the shirt.

FIGS. 13A-B also show first accelerometer 228 and second accelerometer 230 at or near either wrist of the intelligent wear user and carried, respectively by first accelerometer connector trace 231 and second accelerometer connector trace 229. Signal from such sensors that are relatively distant from the sensor module may need to travel a relatively long distance. A longer signal travel distance may mean too much signal strength loss. In some embodiments, a connector may include a material configured to carry a signal a relatively further distance without losing too much signal strength. Such a material may be, for example, a material with good dielectric quality and sufficient flexibility. For example, such a material may be a polyimide, such as Kapton® (DuPont). Such a trace may travel along, for example a sleeve and may be anywhere along the sleeve, such as in or along a seam or away from the seam. FIG. 13B also shows first heart sensor 220 and second heart sensor 242 on the inside of shirt 202 that may be useful for determining heart rate, such as an electrocardiogram sensor (EKG sensor). Such a position enables the sensors to directly contact the skin to obtain readings, such as electrical readings, from the user's body. The sensors are connect with an EKG connector trace 242 to each other (such as for the reasons described elsewhere herein) and to second collar internal connector 262 to send the signal to the collar and onto the sensor manager on the back of the shirt.

Figure 14A:
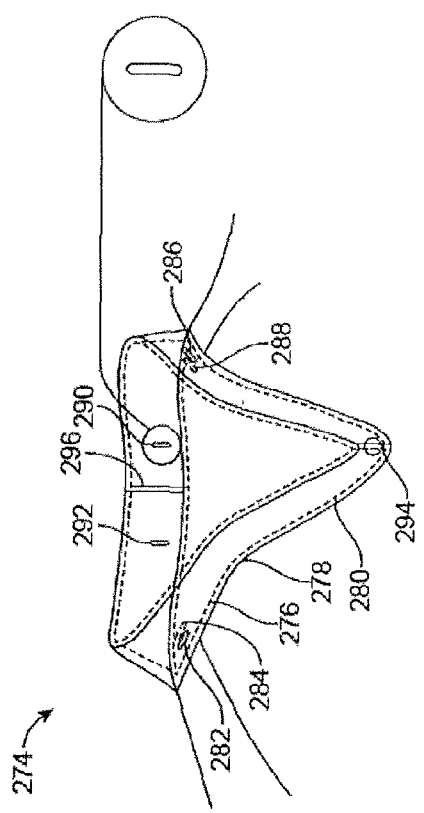
FIGS. 14A-14B shows embodiments of sartorial communications apparatuses configured to include shirts with shirt collars configured for communicating between the front and back of the shirt.
Figure 14B:
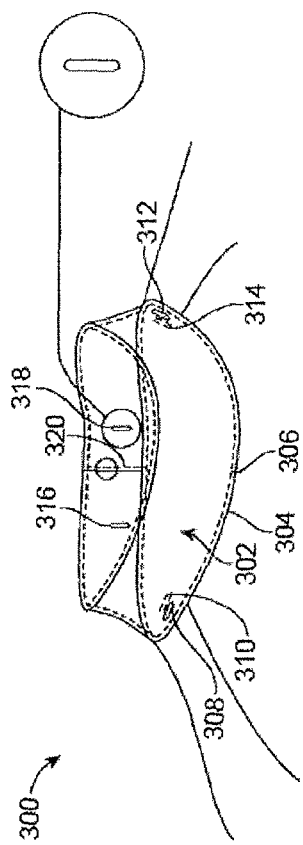

FIGS. 14A-B shows embodiments of shirts with shirt collars configured for communicating between the fronts and backs of the shirts. FIG. 14A shows a V-neck shirt 274 with a V-neck shirt collar while FIG. 14B shows a round-neck shirt 300 with a round-neck shirt collar. Such collars include two layers, an outer layer and an inner layer. One or more than one conductive trace may be placed (including adhered) between the layers (or on either surface of either layer). Other shirts may have a single layer with or without a trace on the external surface or the internal surface. Other shirts may have a plurality of layers and a trace may be placed anywhere along a layer. V-neck shirt 274 includes V-neck shirt collar 276 with a V-neck shirt collar outer layer 278 and a V-neck shirt collar inner layer 280. The front portion includes holes on either side of V-neck shirt collar 276. A first side (left side) of the collar may include a first outer V-neck shirt collar hole 282 in the outer (or external) layer of the fabric and a first inner V-neck shirt collar hole 284 in the inner (or internal) layer of the fabric. As shown, first outer V-neck shirt collar hole 282 and the first inner V-neck collar hole 284 shirt collar hole 284 line up so as to create a through-hole between the layers of fabric. The edges of such holes may be partially bound (e.g. adhered, sewn, welded, etc.) together. A second side (right side) of the collar also includes a second outer V-neck shirt collar hole 286 in the outer (or external) layer of the fabric and a second inner V-neck shirt collar hole 288 in the inner (or internal) layer of the fabric. In some embodiments, such holes may be offset from one another and do not create a through-hole. In some embodiments, a garment may have only an outer hole or a garment may have only an inner hole. In some embodiments, a garment may have one, two, three, four, or more than four holes in the outer layer, the inner layer, and/or any intervening layers. Such holes may be useful as a conduit for extending a trace from a surface of the garment to the internal portion of the collar for conducting a signal, power, or anything else to/from the collar. An external hole may be useful for extending an external trace, such as an abdominal respiratory trace 212, from an external front of a shirt into the collar, which trace may then extend to the sensor module in the back of the shirt. An internal hole may be useful for extending an internal trace, such as a heart rate trace 242 on an inside front of a shirt into the collar. FIG. 14A also shows first rear V-neck shirt collar hole 290 on an external surface of the first (left) side of the shirt collar and second rear V-neck skirt collar hole 292 on an external surface the second (right) side of the shirt collar at the back of V-neck shirt collar 276. Such holes may be useful to extend a trace from inside the collar, down the back of the shirt, and to the sensor module. It is noted that sensor and power may travel in any direction (to/from or from/to) in any such traces. As shown, the rear collar holes only extend through the external (outer) collar layer. In some embodiments, a rear collar hole may be in any location and any relative configuration, as described above for the front collar holes. A trace running through a collar region may be any material. As the collar may be more rigid and/or less extensible than other portions of the garment, a trace may be a relatively rigid trace that may, for example, be a better conductor and reduce signal or power loss. In some embodiments, a trace may be a polyimide material (e.g. Kapton). A trace (e.g. from a front of a shirt) may be connected with the collar region such as by a weld. Two pieces may be soldered together. A hole may be any size and any shape useful for conducting a trace, such as round, oval, square, rectangular, hexagonal, irregular, etc. less than 1 cm in a longest dimension, from 1 cm to 2 cm in a longest dimension, from 2 cm to 3 cm in a longest dimension, from 3 cm to 4 cm in a longest dimension, or may be more than 4 cm. A garment may have 1 collar hole, 2 collar holes, 3 collar holes, 4 collar holes, 5 collar holes, 6 collar holes, or more than 6 collar holes. FIG. 13B shows an embodiment of a round-neck shirt 300 with a round-neck collar 302. As described above, round-neck shirt collar 302 includes a round-neck shirt collar outer layer 304 and a round-neck shirt collar inner layer 306. The collar includes a first outer round-neck shirt collar hole 308 and a first inner round-neck shirt collar hole 310 on a first (left) side of the collar and a second outer round-neck shirt collar hole 312 and a first inner round-neck shirt collar hole 314 on a second (right) side of the collar. The shirt also includes two outer holes on the rear of the collar, a first rear round-neck shirt collar hole 316 and a second rear round-neck collar hole 318. All such holes may have the same configuration, number, etc. as described above. The shirt also includes a rear round-neck shirt collar seam; the V-neck shirt collar includes both front and rear seams. Garments and collars may have seams as appropriate, e.g. for function or for aesthetics. A seam may be made for any reason, such for ease in manufacturing (e.g. to hold two or more portions of fabrics together) or to provide a space (a conduit) for a conductive trace, a sensor module, etc.

Figure 15D:
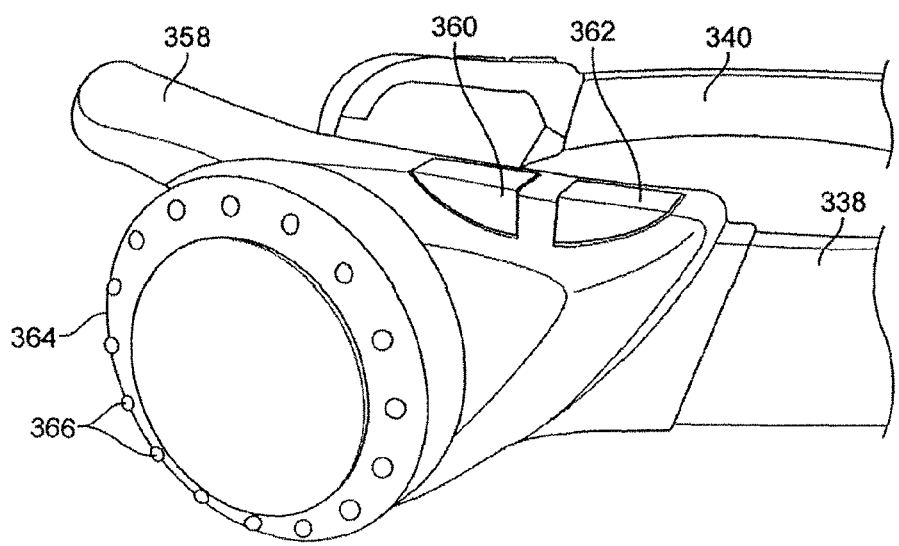

FIGS. 15 A-D show different views of a wearable communication device 322 that may be used with an intelligent wear garment and may connect with a sensor module which may provide inputs (such as what music to play, etc.) to a user of the wearable communication device. Wearable communication device 322 includes base region 324, sensor module connector 334, optionally sensor module 336, first collar arm 338 and second collar arm 340.

EXAMPLE

Figure 16A:
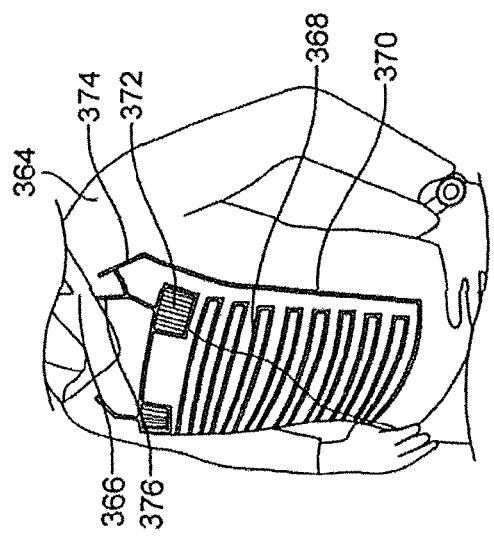
FIG. 16A shows an example of a wearable communications platform generated according to an aspect of the disclosure.
Figure 16B:
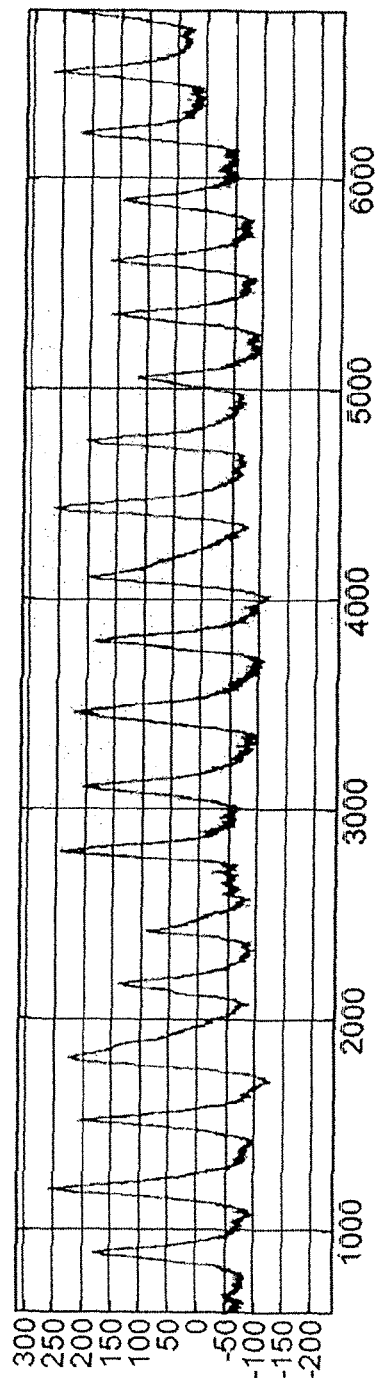
FIG. 16B shows data obtained from a body sensor (configured as a respiratory sensor) such as the one shown in FIG. 16A.

FIGS. 16A-B show an intelligent wear shirt 364 on a model and worn over street clothing 366. The shirt includes a plurality of sensors, including respiration sensor 368 connected to the collar region by respiration sensor connector 370, sensor 372, and sensor connector. FIG. 16B shows data obtained from a respiratory sensor such as the one shown in FIG. 16A during use by an intelligent wear garment user. The variation of resistance (due to sensor elongation during breathing) is shown as a function of time. Samples were taken at 100 Hz. Each "1000" mark on the X axis represents one second.

The intelligent wear systems described herein may be used by groups intelligent wear systems for various purposes.

Bio-competitions: An intelligent wear data system may be configured to create a rankings of users (e.g. such as worldwide) based on their performances. Such a ranking may categorized by activity. Each user may be able to challenge other user based on specific activities or data, and gain scores that will position him/her higher in rankings such as in when victorious. Such a system may generate an engaging game-like experience and response.

As fingerprints can be matched through biometrics, users can search for random 'competitors' that exactly match their capabilities for a fair challenge. Example 1: two break-dancers can compete on the number of head spins. Example 2: gymnasts can compete in the perfect execution of a somersault. An intelligent wear data system application may synchronize the competitors and measure their performances simultaneously. Challengers may be physically far away one each other and the intelligent wear data system may be configured to track the results and elect a winner.

Bio-support to official games: An intelligent wear data system as described herein may track biometrics and sensors used in different types of competitions, such as the official games (e.g. the Olympic Games). An intelligent wear data system as described herein may be used to approve, determine, and/or track the valid execution of a competition. For example, an intelligent wear data system may be used to check or ensure that runners in a race start at the correct time (e.g. that they don't cheat at the start). In another example, an intelligent wear data system as described herein may indicate violations such as a player being offside in a soccer game, etc. An intelligent wear data system as described herein may monitor the physiological status of an athlete. Such a monitoring may comprise verifying that an athlete is not doping, such as in a competition or game such as baseball, bicycling, football, etc. Such monitoring may be performed through a specific sensor, such as a drug detecting sensor. An intelligent wear data system as described herein may be used for determining objective feedback in a competition or game. For example, rather than evaluating a gymnast or other athlete through subjective votes based on a judge's personal interpretation of an execution of an action, an intelligent wear system biometric analysis may be used to provide or contribute to the evaluation, such as by providing objective and reliable feedback on a performance, such as balance, body alignment, speed, etc.

Intelligent wear may allow a user to express themselves not only through 'verbal' communication but also through 'physical' communication. As such, it may provide an instantaneous sharing of information and 'facts' while a user 'action', and increasing the chances of communicating the truth (such as a state of mind or state of body) about an individual (e.g. an intelligent wear user). As such, it may represent a third communication platform (after computers and mobile devices). Communication may be physical in various settings such as follows. Communication may be physical in an 'orchestra-type' direction: Such communication may be similar to how musicians can be directed by an orchestra director through the director's physical movements: a group intelligent wear garment items users may be 'directed' (e.g. 'conducted') into performing a coordinated performance by an intelligent wear system (e.g. an intelligent wear system director). Such a 'direction' may comprise communicating with each individual user such as through the module, the speakers, the headsets, the sensors and/or activators in the users' apparel. In addition to conducting music, a director may also conduct a dance, an expression (e.g. an interpretation or a response to an intelligent wear user's inputs), an athletic activity or exhibition, a sports activity or exhibition, sport fans' support of their teams, manifestations, celebrations, etc.

A 'director' may be able to 'conduct' and create music through the users' speakers and/or play, chant, and/or speak through them in a coordinated way similar to the way a 'director' directs an 'orchestra'. A 'director' may also direct (or control) activators, such as haptic or other activators, in the shirts so as to guide the users into singing, chanting, dancing, moving (such as coordinating a movement such as a 'wave' or other fans' expression in a stadium, or simply other groups/crowd communal expression), performing athletics, etc. A user may perform (sing, speak, dance, run, plays tennis, etc.) by responding to their apparel activators' signals from the director. A director may direct by communicating/giving a group of users instructions such as through a vocal instruction (e.g., through an apparel headsets or speakers) or a haptic instructions (e.g., through touch feedback/vibration through an activators in their intelligent garment). A user controls may control certain aspects of a system. A user may choose to participate (or not participate) in an event by connecting or disconnecting from the 'director'. A user may control a volume of the speakers. Such an 'orchestra-type' direction may be used at, for example, a sporting event, a concert, an exhibition, a political event, a parade, a carnival, a flesh mob, a group celebration, a self-organized event, a rally, an inauguration, etc. Similar to a director, an event organizers may coordinate large groups (e.g. thousands, hundreds of thousands) of intelligent wear users (though their apparel). Such a group may participate in an event by (coordinate) singing, chanting, dancing, emitting light, social networking and/or performing other activities in unison. Such coordination of intelligent wear users (though their apparel) may be directed by, for example, an organizer of a concerts, exhibition, political event, parade, carnival, etc. to provide (or ensure that) expressions that are in line with the spirit of the event they have organized. Such coordination of intelligent wear users (though their apparel) may be directed by, in a sports event, a fans of one of the teams who may 'direct' a few, some (or a section/wing of), or all of the fans into a coordinated show support of the team. Such coordination of intelligent wear users (though their apparel) may such as in a group celebration, party, self-organized event, be directed by an organizer or by a plurality of participants, such on a rotation schedule, or by the 'will of the group' who may direct the participants into coordinated expressions, dances, singing, chants, movements, celebrations, screams, etc. The 'will of the group' refers to the synthesis of what the group desires. Such a synthesis, for example, may be determined by an intelligent garment system algorithm. Such coordination of intelligent wear users (though their apparel) at a sports events, may include coordinating fans activities such as a) synchronizing speakers (so as to synchronize a chant, formation, shouting a player's name, booing a referee, etc.), or b) synchronizing haptic vibration codes (1=waves, 2=chant, etc.) which may be adapted to local fans' cultural behavior. Such coordination of intelligent wear users (though their apparel) at a sports events, may include coordinating an event message such as synchronizing LED displays on fans' T-shirts to display a stadium message such as, "goooaaalll" or an image such as a flag. A flag image may be created by mapping the fans and using them as 'human pixels' in a 'bleaches screens'.

Another aspect of the invention comprises generating a video output based on an intelligent wear garment user's movement. Such a video output may include a camera-less video production. Such a video output may comprise using an intelligent wear 'shooting' apparel item. A video based on an intelligent wear user may be generated (produced) by the transformation of body sensor signals (for example, biometric signals). Such body sensor signals may include any signals as described herein or as known in the art, such as measuring a vital sign, measuring palpitations, measuring or inferring an emotional state, determining body movements (which may be determined very precisely), assaying sounds, sighs, and voice comments, etc. of the user. An audio and/or visual images based on the body sensor signals may be generated. Such an audio or visual image may be generated without a camera (e.g. without a video camera) recording or shooting the action. Such biometric measurements (body sensor signals) may be taken by an intelligent wear 'video and audio-shooting' garment through strategically positioned sensors measuring (and representing) biometrics of an intelligent wear user 'in action'. Such a garment may be a flexible, conformable garment, such as a flexible, conformable body suit, a leotard, socks, etc. Such a garment may have any of the capabilities, characteristics, elements, features, etc. as described for any intelligent wear garment herein or as known in the art. Any analog sensor data may be transformed into digital data, such as by a module into the intelligent wear leotard or other garment. Such data may be used in any way to generate video and/or audio output. A user may generate such an output. A user's biometric signals may be communicated (e.g. in real-time to the cloud into the users' intelligent wear page). Any such data may then be translated into a video and audio output (for example, such as a stream) by transforming the data into a representation (e.g. which may be an exact representation or may be a stylized representation) of the user's looks (anatomy, features, etc.) and user's voice. Such a transforming may be performed by 'applying' the user's real time movements to a pre-recorded 'avatar' of the user. A user may choose a 'look' of the moment by choosing/changing the clothing, hair style, skin complexion, etc. of the avatar). In one example, a flexible conformable garment useful for generating a video and/or audio output may include a compression shirt with a (electrically connected) compression balaclava, a (electrically connected) compression leggings and (electrically connected) compression socks. Sensors that may be particularly useful include a plurality of tri-axial accelerometers (such as, a gyroscope and a magnetometer). Such sensors may be placed, for example, at positions on (specific) synovial (diarthrosis) joints. Such joints may be particularly useful because they are the most common and most movable type of joint in the body of a mammal. A 'video and audio-shooting' garment may have any type and any number of sensors. In a particular example, an 'video and audio-shooting' garment has about 19 accelerometers: one of each shoulders and hip (4), one on each knee and elbow (4), one each hand (extensor indices) (2), one on each foot (e.g. on the hallux) (2), one on each ankle (2), one on each wrist (2), one on the neck (rear) (1), one on the chin (1) and one on the upper parietal bone (1). Such a garment may further have a heart-rate sensor, a microphone, a respiration sensor and a skin conductance sensor. Such a sensor may be connected through a power trace to a module incorporated into the garment (such as placed between the scapulae). Data and other information may be managed by a sensor management system in the module. Such data and other information may be sent, e.g. by the intelligent wear module, to the cloud in real time.

Another aspect of the invention comprises determining a user's garment fit by assaying an intelligent wear garment fit. Such a determining may be used for determining a user's intelligent wear garment fit or for determining any other type of garment fit (e.g. length, shape, size, etc.). Such a determining may be performed, for example, by the user or may be performed remotely. A user's body dimensions and shape may be determined from a plurality of body sensor signals from a plurality of body sensors on a flexible, conformable, intelligent wear garment item fitted over a user. Such a garment may have, for example, a plurality of rings (circles) configured to be placed around the limbs, the torso, the trunk, the neck, and/or the head. Such a garment may have 1, from 2 to 5, from 6 to 10, from 11 to 20, from 21 to 50, or more than 50 such rings. In a particular example, an intelligent wear garment useful for a fitting may have from 2 to 4 rings placed along each leg, from 2 to 4 rings places along each leg, each forearm and each upper arm), from 4 to 6 rings placed along the trunk and the torso, and 1 ring on the neck. Such intelligent wear fitting apparel may come in a plurality of different sizes and may be calibrated for different dimensions. A change in an amount of stretching of a ring may be used to determine a user's measurement. Such a user may use the information to choose a particular garment size (or dimension, shape, etc.) or to custom-order a particular garment size (or dimension or shape) to have a precise fitted, tailor made garment. Such a garment may be an intelligent wear garment or may be another garment (e.g. non-intelligent wear garment).

An intelligent wear system may fulfill certain user's needs (ordering food, supplying a beverage, supplying a nutritional supplement, supplying a vitamin, requesting/obtaining a service, providing health and/or medical support, providing safety analysis and support, etc.) in real time based on the intelligent wear user's true needs may be evaluated by intelligent wear system algorithms. Such algorithms may include analyzing, assaying, and/or computing a user's biometrics measurements (e.g. of age, gender, ethnicity, physiology such as body structure, the strength and weakness of their skeleton, joint flexibility, bone and other articulations, organ health), psychological state (mind set, emotional responses, neurologic profile, psychological profile), athletic needs (e.g. a soccer player may need more potassium then does a skier), activity (running, climbing, skiing, etc.), spiritual elements (beliefs, religious or spiritual guidelines), needs responsive to particular time (e.g. time of day), to weather, to a seasons, to a location and to users sensorial and economical preferences. A user may see a recommendation (e.g. of what they need) described and evaluated, such as on a personal intelligent wear web page or communicated to them (e.g. though a module, phone, etc.). Such needs and recommendations may be assayed or determined by algorithms configured to use user measurements and other parameters (such as those described above). Such an algorithm or an output from such an algorithm (e.g. a recommendation) may be analyzed by an analyst such as a professional (e.g. a doctor, a nutritionist, a coach, a trainers, etc. Such a professional may (or may not be) be chosen by the user.

The stretchable and conductive ink patterns described herein may be printed onto garments, including in particular compression garments, to form sensors, conductive traces, and/or contacts. In general, any of the apparatuses described herein (e.g., garments, including but not limited to shirts, pants, and the like) may be configured as garments for detecting and monitoring physiological parameters, such as respiration, cardiac parameters, sleep, emotional state, and the like and may include any of the conductive ink patterns described.

Any of the garments described herein may include a Sensor Manager System (SMS) placed directly onto the garment (e.g. shirt, shorts or in any other component of the wearable device, i.e. balaclava, socks, gloves, etc.). The SMS may include an electronic board. Connections to the SMS may be made by semi-rigid materials (e.g., Kapton) that may be included as part of the garment.

An SMS that is integrated into the garment (as opposed to being provided by a separate device such as a smartphone) may provide numerous advantages. For example, an integrated SMS can manage a larger number of connections with the different sensors, and may processes the signals and communicates with the phone by means of a single mini-USB cable (e.g., independently of the number of signals processed). No matter the number of sensors that will be included in future devices (e.g., shirt, thighs, gloves, socks, balaclava, etc.), the connection between SMS and sensor module (e.g., phone) may always be based on a single 5-pin USB connection, thus substantially reduce the size of the female and male connectors from the device to the phone module. In a typical configuration, an SMS connects to a male connector through a UART (Universal Asynchronous Receiver-Transmitter) module and the male connector communicates to the mobile through another UART and an UART-to-USB module (see attached schematic and drawings).

An integrated SMS can be placed in different locations on the garment. For example, it may be placed at the base of the neck between shoulder blades, on the lumbar region on the thighs or even on the socks, gloves, balaclava, etc.

An SMS may also be configured to communicate with different phones for the device. As mentioned, an integrated SMS may also allow you to have more connections (pins) to connect to different sensors/outputs. For example, an accelerometer may need 5 pins if you have the SMS present in a sensor module (e.g., mobile phone); an SMS integrated into the shirt may need fewer connectors, for example, such an SMS may need only 2 pins. With more sensors, without an integrated SMS the number of connectors may become unfeasible.

In general, the SMS may be a module (chip) that manages the signals from and to the sensors, and may act as an interface between the communication system (sensor module configured from a phone, etc.) and sensors. The SMS may manage the connection and interfaces between them. For example, and integrated SMS may include physical connections to sensors and may manage the way in which the signals are processed and sent between sensors and a sensor module and/or other analysis or control components. The SMS may also include or may connect to a multiplexer to alternate readings between various sensors to which it is connected.

In some variations, a SMS may provide proper power supply to passive sensors or active sensors. An SMS may take power from the mobile systems through a port such as a USB port. An integrated SMS may communicate from one side to a sensor module (e.g., communications systems/phone, etc. configured as a sensor module) through a USB port. The SMS may act as an interface or a bridge between the sensors and the sensor module.

In addition, any of the integrated SMSs described may be configured to include on-board processing (e.g., preprocessing), including, but not limited to: amplification, filtering, sampling (control of the sampling rate), and the like; typically basic pre-processing. An integrated SMS may also encode signals from the one or more sensors. In some variations the SMS may include a microcontroller on board. Further, and integrated SMS may also generally manage communication protocols to/from any or all of the sensors, and may make an analog to digital conversion (if the signals are analog) and may also communicate with a comm port of a USB, before going to the USB. For example, an SMS may be configured to convert the signal into UART to the USB signal protocol.

In addition or alternatively, any of the integrated SMSs may be configured as a signal receiver/transmitter. For example, an SMS integrated into the garment may be adapted to convert parallel signals to serial signals (in the order of the data).

As mentioned, an integrated SMS may be placed in any position on a garment, e.g., on or near the neck region, or more peripherally. Although the SMSs describe herein are referred to as "integrated" SMSs, these SMSs may be included on or in the garment (e.g., in a pocket or enclosure, though in some variations it is not physically connected/coupled to the fabric, but is instead placed on the garment. Thus, any of these SMSs may instead be referred to as dedicated or specific SMSs rather than (or in addition to) integrated SMSs. For example, the SMS may be placed under the female connector (housed inside the female connector), as part of the garment. When you wash the garment the SMS may get washed with the connector and the chip; the pins and SMS are waterproofed.

In some variations, the connectors (e.g., pins/ports) of the SMS are adapted to water resistant/water proof. For example, the pins used may make connections that are waterproof, e.g., with connections that only open when you engage the male pin, but are otherwise closed and waterproofed.

In any of these integrated SMSs, the SMS is a part of the garment, and are worn with the garment; the SMS module may pre-process the signal(s) to prepare them for transfer.

Thus, in any of the garments described, an SMS (Sensor Management System) may be included that is positioned on each garment (onboard/dedicated), rather than separate from the garment, e.g., as part of a separate sensor module, such as a general-purpose smartphone that may be held in a pocket on the garment, as previously described. Each garment may have an SMS (chip/microchip) that allows the garment to have connectors (female and male) with a numbers of pins (inputs/outputs) so that data from all the sensors in the garment (shirts, tights and accessories, such as gloves, socks, balaclava, etc.) may be first processed by the SMS and then sent through a connection (e.g., as few as 1 or 2 pins, or more) to the phone/communication module. In general, some of the sensors and components of the garments described herein may individually require multiple connections and thus a dedicated SMS may be very useful. For example, an IMU may require 5 pins and as many as 20 IMUS (or more) may be included as part of a garment, in addition to other sensors. Thus, the use of a dedicated SMS may allow the garment to manage a large number of data connections/contacts.

Sensors

In addition to the sensors described above, such as touch point sensors, respiration sensors, bioelectrical sensors, etc., additional sensors may be included in any of the garments described herein. For example, a garment may include one or more skin conductance sensor. A sensor for measuring skin conductance can be made by two annular rings of the stretchable, conductive ink (see below) placed at the level of the third phalange of whatever couple of fingers (thumb, index, middle, ring and little finger). In some variations, the sleeve of the shirts has at the wrist level an integrated extension for this purpose. The skin conductance, depending on the sweating level, is measured as the inverse of the electrical resistance between the two considered 'electrodes' (annular rings).

Another integrated extension of the apparatuses described herein includes a full glove that, in addition or instead of a skin conductance sensor, incorporates a pulse-oximetry based on optical fibers. The use of optical fibers may also allow the incorporation other types of sensors. In addition, a full or partial glove may include additional sensors such as accelerometers, inertial measurement units (IMU), etc. Such glove-based sensors may allow applications in specific activities (e.g. playing a music instrument, type writing, etc.). A glove or pair of gloves may be configured to connect to other garments (e.g., shirts, etc.) or be formed as a sub-region of another garment (e.g., a shirt with finger regions/gloves, etc.).

Similarly to the gloves described above are socks or balaclava extensions, that incorporate other types of sensors, such as accelerometers, inertial measurement units (IMUS), EEG electrodes, etc. This allows applications in specific sports (e.g. football) and activities (e.g. playing chess).

Production Processes

In general, the production of any of the garments described herein may include constructing the garment such as the sensors are held close and in stable contact with the skin. Thus, the sizing of the garment may be very precise, particularly in the following areas: thorax (because of different sizes of pectorals and breasts despite same corporeal size), abdomen (also because of individual size variablity), armpits, forearms, etc. The garments may be therefore precisely fit/manufactured, in addition to being made from compression materials. The manufacturing and design processes may also include garment cutting.

Any of the garments described herein may be printed by, e.g., printing and transferring of the conductive ink patterns and/or insulation. The printing may be performed by cylinder-type machines (because the printing is more precise and faster) using a heat transfer technique. For example, transfer on both sides of the fabric may be performed at 150° C. for 15 seconds.

Thereafter, insulation may be applied (e.g., when capacitive touch points are used, such points may be insulated). The internal regions (i.e., in contact with the skin) of electrodes of a capacitive touch point may be insulated by heat-welding a layer of high quality polyurethane film exactly reproducing the shape of the electrodes. The size of the insulation layer may be slightly larger than the size of the electrode to allow a complete covering thus to avoid 'lateral' contamination of biopotentials.

In variations in which higher conductive connections are used, the apparatus may include the addition of higher-conductive substrates and materials, such as Kapton and/or conductive threads. Thus, the formation process may then include the application of Kapton traces. Once positioned, Kapton may be secured to the fabric through high quality polyurethane tapes for heat-welded applications. In order to maximize comfort of movement, the electronics on the Kapton may be designed to have a single layer, thus minimizing its thickness.

The garment may then be sewed. The sewing may be performed by traditional processes, although in some variations, sewing over ink of Kapton traces may be avoided.

At the same time or thereafter, soldering may be performed, e.g., to connect the region including an additional (e.g., Kapton) substrate for higher-conductive traces with printed conductive ink sensors, electrodes and/or traces. For example, soldering between ink traces and Kapton terminals may be performed by using conductive epoxy, successively covered by a high quality polyurethane film.

Thereafter, in some variations a semi-rigid collar region may be attached, e.g., to secure and cover an integrated SMS module, Kapton traces, and male connectors. A collar may be made of a polyurethane material that takes the shape of the user's shoulders and may be applied by thermal welding through a transfer machine with plates custom-made to fit the body surface in the neck region.

In some variations, the method of forming the garments may also include the addition of 'stretching limiters' made, e.g., of stripes of polyurethane material with limited elongation. They may be positioned by thermal welding in the inner part of the garment, in proximity of long ink traces (e.g. respiration traces), in order to prevent overstretching (e.g. during wearing) that could either break a trace, or determine permanent elongation, that must be avoided for functional and aesthetic reasons. To enhance their strength, they may be positioned in a way to run between two seams.

In some variations the garment may be produced by installing a stretch-limiter, such as a silicone cord. To avoid stretching of the garment and its sensors when the user is wearing the garment and putting the garment on, a cord made of silicon may be applied (e.g., by thermal welding) to the lower edge of the garment, running all around the edge. This may allow the wearer to easily pull the shirt down from the armpits to the waist after the collar and the sleeves have been inserted, without overstretching the garment.

Materials

In general, the garments described herein may include a compression fabric to secure that sensor are in good permanent contact with the skin. For example, the anterior part of the shirt may have a lower percentage of elastane (between 5 and 20%) than the rest of the body, which may include a higher percentage of elastane (between 15 and 40%). The fabric may be stretchable into two ways (one direction) and may be positioned with the least stretchable side placed horizontally to respect human body which dynamically stretches more horizontally than vertically.

As discussed in greater detail below, any of these garments may include a stretchable conductive ink pattern and/or a stretchable insulator (over/surrounding) the conductive ink pattern (e.g., trace, sensor, electrode). Both the conductive ink pattern and the insulator may be stretchable, up to some percentage, X% stretchable (e.g., up to 5% stretchable, up to 6% stretchable, up to 7% stretchable, up to 8% stretchable, up to 9% stretchable, up to 10% stretchable up to 11% stretchable, up to 12% stretchable, up to 13% stretchable, up to 14% stretchable, up to 15% stretchable, up to 16% stretchable, up to 17% stretchable, up to 18% stretchable, up to 19% stretchable, up to 20% stretchable, up to 21% stretchable, up to 22% stretchable, up to 23% stretchable, up to 24% stretchable, up to 25% stretchable, up to 30% stretchable, up to 35% stretchable, up to 40% stretchable, up to 45% stretchable, up to 50% stretchable, etc.). This may also be expressed as more than X% stretchable (e.g., more than 5% stretchable, more than 6% stretchable, more than 7% stretchable, more than 8% stretchable, more than 9% stretchable, more than 10% stretchable more than 11% stretchable, more than 12% stretchable, more than 13% stretchable, more than 14% stretchable, more than 15% stretchable, more than 16% stretchable, more than 17% stretchable, more than 18% stretchable, more than 19% stretchable, more than 20% stretchable, more than 21% stretchable, more than 22% stretchable, more than 23% stretchable, more than 24% stretchable, more than 25% stretchable, more than 30% stretchable, more than 35% stretchable, more than 40% stretchable, more than 45% stretchable, more than 50% stretchable, etc.). Stretchable typically mean capable of being stretched (e.g., by applying a force such as a pulling force) from a starting length/shape and returning to approximately the starting length/shape. In some variations may mean additionally or alternatively, resisting breaking when a deforming force (elongating or distorting from the original length/shape) is applied (and eventually released). Examples of stretchable conductive inks and characteristics of such inks are provided below.

As mentioned, any of the garments may also include a substrate attached or formed as part of the garment for higher-conductive paths, such as Kapton films and/or conductive threads (which may be included in a pattern allowing stretching in one or more directions). Other flexible, wearable substrates may also be included. Any of the garments may also include one or more polyurethane films and tapes for sewn and heat-welded applications (e.g., high-quality polyurethane films and tapes). In addition any of the garments may also include an electrical insulation material (e.g., polyimide materials, etc.) for covering/insulating a conductive trace, forming a part of a sensor, or the like.

A substrate such as Kapton may be fixed to on onto the garment. For example, the substrate may be sewn and/or attached by an adhesive, etc. The substrate may be held in a pocket or other region of the garment. As mentioned above, any of the garments may include a limiter (e.g., stretch limiter) of a second material (e.g., a cloth material that is less stretchable than a compression garment, etc.). Similarly, when conductive threads are used, they may be sewn and/or adhesively applied to the garment.

Any of these garments may also or additionally include silicone for sewn and heat-welded applications.

Strechable Conductive Inks

A stretchable, conductive ink typically includes a percentage of conductive material (e.g., around/approximately 20%, 25%, 30%, 35%, 40%, 45%, 50%, 55%, 60%, 65%, 70%), and a biocompatible binder (e.g., acrylic binder that is formaldehyde-free), a thickener (e.g., polyurethanic thickener) and a humectant and/or solvent (e.g., propylene glycol). The stretchable conductive inks as described herein generally meet a minimum conductance as well as a minimum stretching property.

In one example, a conductive ink used to form a stretchable conductive ink composite (along with an adhesive and intermediate/gradient region) may be formed of: 50% Carbon Black, 40% Acryilic Binder, be totally formaldehyde-free, 5% propylene glycol, and 5% polyurethanic thickener. The conductive material (Carbon Black) may be particulate. Carbon Black may be preferred, particularly compared to other conductive materials such as silver or other metallic. In general, the conductive ink may have a composition including: between about 40-60% conductive particles, between about 30-50% binder; between about 3-7% solvent; and between about 3-7% thickener.

The conductive ink patterns described herein are not only conductive, but also stretchable and therefore can work properly on compression garments. In addition, the stretchable conductive ink patterns appropriate for forming the garments described herein may be ecologically appropriate (e.g., having a formaldehyde concentration lower than 100 ppm), and resistant to washing (with preservation of electrical and elastic properties after multiple washes).

Figure 18:
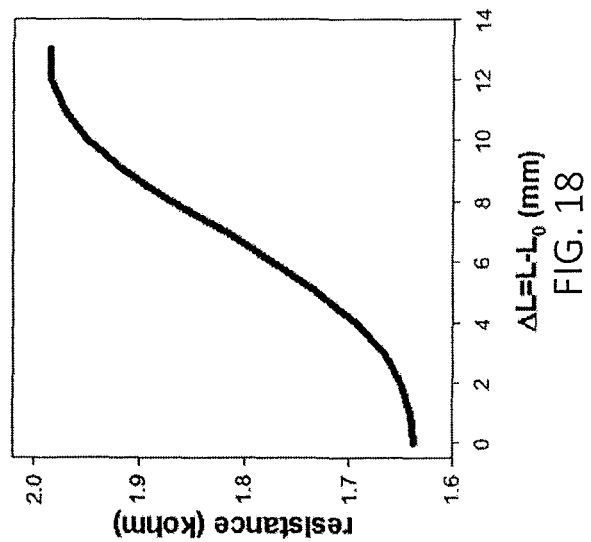
FIG. 18 is a graph characterizing the resistance for one variation of stretchable conductive ink.
Figure 17:
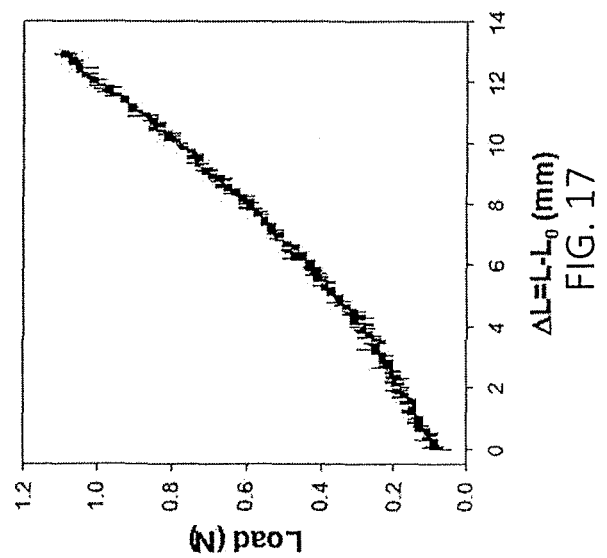
FIG. 17 is a graph characterizing the force vs. extension for one variation of stretchable conductive ink.

Experimental studies have confirmed that the stretchable conductive ink composites (patterns) described herein are stretchable. For example, FIGS. 17 and 18 illustrate preliminary results of testing conducted on a sample of conductive ink printed on a compression textile as described above. A video camera was used to demonstrate that no fractures developed in the ink during the extension (e.g., change in length of up to 13 mm was examined). The conductance (e.g., resistance) varied with applied force between approximately 1.6 kohms to 2 kohms, while a linear stretch was observed up to 1.1 N (e.g., stretch up to approximately 13 mm without breakage at approximately 1.1N). In general, the stretchable conductive inks described herein may be within a performance range of being stretchable up to at least 1 N of force (e.g., up to at least 2 N, up to at least 3 N, up to at least 4 N, up to at least 5 N, up to at least 6 N, etc.) and/or stretchable (without breaking) up to at least 5 mm (e.g., up to at least 6 mm, up to at least 7 mm, up to at least 8 mm, up to at least 9 mm, up to at least 10 mm, up to at least 11 mm, etc.) and/or stretchable up to a ratio of applied stretching force (in N) to extension length (in mm), e.g., around about 1 N/mm without breaking. Surprisingly, in the experiment having results shown in FIG. 17, the conductive traces examined did not evidence any breakage up to almost 2 N, which is a reasonable near-maximal force that may be applied when applying/wearing a garment. Neither macro (visible to the naked eye) nor micro breakage was apparent.

In general, the resistance of the stretchable conducive ink may depend upon the size of the trace, including thickness, length, etc. (which may vary under stretch) and may be lower than about 5 kohm (e.g., less than about 4 kohm, less than about 3 kohm, less than about 2 kohm, etc.) at rest and under a predetermined stretch force (or force/stretch length). In general, the resistance may be within a range of a few hundred ohms to a few hundred kohms. In FIGS. 17 and 18, the tested stretchable conductive ink was printed on the compression garment fabric to a length of 60 mm and a width of about 10 mm; eight layers of ink were applied to form the final thickness (which was less than about 2 mm (e.g., approx. 1 mm or less).

Any of the garments described herein may be used as part of a system including multiple garments that connect (either or both directly connect or wirelessly connect). For example, and upper body garment/device may connect with lower body garment/device. Signals from sensors positioned on garments on the lower part of the body (e.g., shorts, thighs, socks, etc.) may be transmitted to an SMS on an upper garment (e.g., shirt, etc.). A connection may be made through a support substrate (e.g., Kapton) including traces that can connect through a connector positioned in an internal portion of the upper garment (e.g., the lower hem region of the upper garment).

Example 1: Garments that Detect Respiration

Garments may be adapted to detect respiration, and in particular, regional respiration. Such devices may be used at the request of a medical professional, or by anyone who wishes to monitor respiration. A respiration-monitoring device may be adapted for the continuous and accurate monitoring of respiration, including monitoring of respiration in one or more regions. A complete and accurate measurement of several respiratory parameters (described below) may be made using a plurality of stretchable conductive ink traces (patterns) arranged in a wavy pattern (e.g., a 'zig-zag' pattern, a sinusoidal pattern, sawtooth pattern, etc.) arranged in different regions of the garment so that they are positioned about a wearer's torso. Regions including lengths of stretchable conductive ink may include: the anterior (front) part of a shirt, the posterior (back) part of a shirt; each or either of the two lateral sides of a shirt, etc. Sub-regions within these regions may also be used (e.g., upper/lower, left/right, etc.). The stretchable conductive ink, as described above, may have a resistance that varies slightly with stretch; this property may be used to detect and/or measure body movement as the ink is stretched while worn on the body.

As described below, in some variations, four or more respiratory signals may be measured to determine localized respiration. For example, twelve signal may be measured by grouping the variable resistances of the traces (or an average of numerous traces) that are placed in the following areas/regions: (1) anterior, upper right (e.g., 6 traces); (2) anterior, upper left (e.g., 6 traces); (3) anterior, lower right (e.g., 5 traces); (4) anterior, lower left (e.g., 5 traces); (5) posterior, upper right (e.g., 6 traces); (6) posterior, upper left (e.g., 6 traces); (7) posterior, lower right (e.g., 5 traces); (8) posterior, lower left (e.g., 5 traces); (9) lateral, upper right (e.g., 3 traces); (10) lateral, lower right (e.g., 5 traces); (11) lateral, upper left (e.g., 3 traces); (12) lateral, lower left (e.g., 5 traces). All or a subset of these regions may be used. Based on the arrangement of stretch-sensitive conductive traces, parameters may be extracted by analysis of the different signals. For example, a measure of total tidal volume may be determined by adding the signals from all of the traces in each region (e.g., 1+2+3+4+5+6+7+8+9+10+11+12). A measure of rib cage tidal volume may be determined by adding the signals from the upper regions (e.g., 1+2+5+6+9+11). A measure of abdominal tidal volume may be determined by adding the signals from the lower (abdominal) regions (e.g., 3+4+7+8+10+12). A measure of the rib cage respiratory region may be determined by adding just the region associated with the right rib cage (e.g., 1+5+9); a measure of the left rib cage may be measured by adding just the regions associated with the left rib cage, (e.g., 2+6+11). A measure of the respiration in/at the right abdominal region may be determined by adding the signals from the right abdominal region (e.g., 3+7+10), and similarly a measure of the respiration in/at the left abdominal region may be determined by adding the signals from the left abdominal region (e.g., 4+8+12).

From the time course of the signals (e.g., the signal of the total tidal volume), temporal parameters of breathing, such as respiratory frequency (f), inspiratory time (Ti), expiratory time (Te), and/or duty cycle [Ti/(Ti+Te)] can be determined, recorded, measured and/or displayed (as can any of the signals detected on the garment).

Figure 19B:
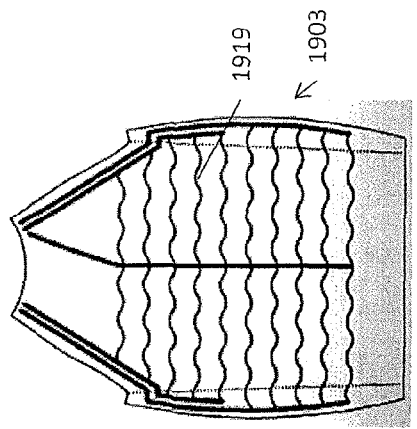
FIG. 19B is a partial view of the front and lateral regions of the shirt of FIG. 19A.
Figure 19A:
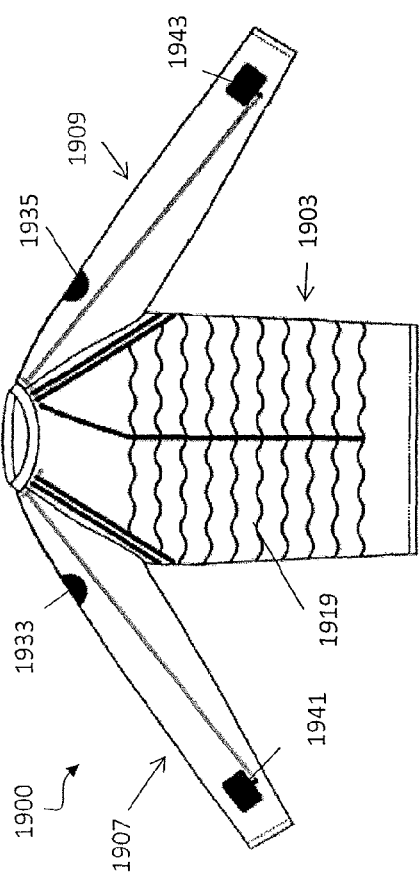
FIG. 19A shows a front view of a shirt configured as a respiration monitoring garment.
Figure 19C:
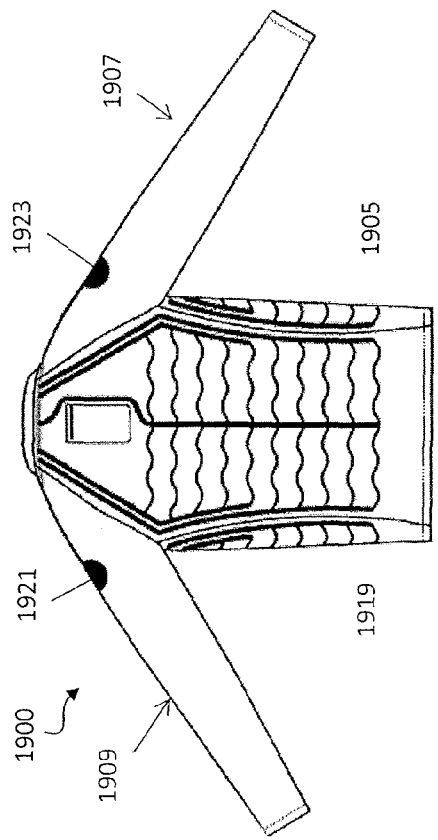
FIG. 19C shows a back view of the same garment of FIGS. 19A and 19B.

For example, FIGS. 19A-19C illustrate one variation of a shirt for detecting and/or monitoring, including continuous monitoring, respiration. In any of these examples, the apparatus, which may be referred to interchangeably as a device or system, may be configure to continuously and accurately monitor respiration The garments shown in FIGS. 19A-21A are compression garments (shirts) typically composed by four parts: (a1) 1903 anterior and lateral sides; (a2) 1905 posterior (back); (a3) 1907 right arm; (a4) 1909 left arm. These parts are sewn together after deposition of conductive ink, conductive connector (e.g., Kapton with conductive material) and layers of insulating material, e.g., by a transfer process.

In general, conductive ink traces may be used as sensor. In FIGS. 19A and 19B, the sensor is a plurality of conductive ink traces that are stretchable traces. Conductive ink and adhesive is used to form the conductive traces 1919, as described herein. Any of these devices may also include a sensor manager unit. The sensor management unit 1921 may be a processor that is placed on the garment (e.g., on the back) in connection with an interface for connecting the sensors to the processor. The processor may be, for example, a smartphone or other handheld device. The apparatus may have a communication unit; this communication unit may be separate or may be integrated with the processor (and/or may include its own dedicated processor). For example, a communication unit may also be placed on the back, and connect to the interface.

Additional sensors may also be used, including motion sensors. For example, a tri-axes accelerometer (alone or, e.g., embedded in the communication system), may be included.

In general, any of these devices may include one or more wearer inputs, such as 'touchpoint sensors'. For example, two capacitive touch points 1933, 1935, placed on the arms, may be used. A touchpoint sensor may include two electrodes (e.g., one on the inner, the other on the outer, surface of the garment in corresponding positions), made of conductive ink patterns, a separating layer of the textile between the two conductive electrode patterns; and an insulating layer deposited onto the internal conductive ink pattern layer. A connecting trace may be included between the external electrode and a terminal point placed close to the neck.

Additional sensors may include one or more electrodes, such as an electrode to detect hear rate. For example, two electrodes 1941, 1943 for heart rate (HR) measurements, made of conductive ink patterns may be placed on the inner surface of the right and left arms of the shirt. These electrodes may be connected by a conductive connector such as a conductive (Kapton) traces, or conductive thread, connecting the HR electrodes to the terminal point close to the neck, as shown in FIGS. 19A and 19C.

In general, the respiratory traces may be positioned in any region of the body of the shirt to detect movement (expansion/retraction) due to respiration in that portion of the body. A complete and accurate measurement of several respiratory parameters (see below) may be provided for individual regions of the wearer's body by positioning stretchable conductive ink traces, 'zig-zag' shaped, (e.g., by transfer process) in different regions of the body of the shirt. For example, conductive traces may be positioned on the anterior and the two lateral sides of the shirt, on the posterior part (back) of the shirt, and in various sub-regions of these portions.

In FIGS. 19A-19C, eight signals are measured by the sensor manager unit (processor) as voltage variations determined measuring by the variable electrical resistance of the traces placed in parallel in the following areas:

1. Anterior+lateral, upper right (5 traces in parallel).
2. Anterior+lateral, upper left (5 traces in parallel).
3. Anterior+lateral, lower right (5 traces in parallel).
4. Anterior+lateral, lower left (5 traces in parallel).
5. Posterior, upper right (6 traces in parallel).
6. Posterior, upper left (6 traces in parallel).
7. Posterior, lower right (5 traces in parallel).
8. Posterior, lower left (5 traces in parallel).

The vertical traces shown are made of conductive ink, and constitute the terminals of the total electrical resistance in these 8 areas. These traces are connected to terminal points positioned close to the neck (at the interface region). A processor or other circuitry may be used to detect/monitor resistance. For example, in some variations a sensor manager (processor) may be used to obtain and/or store, transmit, analyze, process, etc. the 8 signals listed above. The processor may also incorporate and analyze, transmit, process and/or store additional signals, including the signals obtained by summing one or more combination of single signals. For example, as mentioned above:

Total=1+2+3+4+5+6+7+8
Rib cage signal=1+2+5+6
Abdominal signal=3+4+7+8
Right rib cage signal=1+5
Left rib cage signal=2+6
Right abdomen=3+7
Left abdomen signal=4+8

From the time course of the signal of total signal, the following temporal parameters of breathing can be obtained: respiratory frequency (f), inspiratory time (Ti), expiratory time (Te), duty cycle [Ti/(Ti+Te)], etc.

As mentioned above, these signals may be stored, transmitted, analyzed, etc. by the processor and/or communications unit.

Example 2: Electrocardiogram (ECG) Measuring Garments

Also described herein are garments that may be used to effectively and continuously monitor electrocardiogram (ECG) signals. For example, a garment may be adapted to measure signals by including pairs of redundant traces between which the apparatus (e.g., garment, control/sensing module, etc.) may switch. In some variations the SMS and/or a sensor module may determine which set of electrodes between the redundant multiple electrodes to use in detecting a particular lead for an ECG. FIGS. 20A-20B, 21A-21B, and 21C-21D illustrate garments configured to measure ECGs. Each of these garments includes redundant leads (two or more) where each of the redundant leads can detect a signal from an electrode that may be used to determine an ECG signal for that lead.

The electrodes used to detect ECG signals may be formed of the stretchable conductive ink composites described herein. In some variations, the electrodes are printed, applied or formed on one side of the garment (e.g., the inner surface) and adapted to be in continuous contact with the subject's skin so as to measure ECG signals. Electrodes may be connected via conductive traces (formed by, for example, stretchable conductive ink patterns and/or combinations of stretchable conductive ink patterns and higher-conductance traces such as conductive thread and/or printed Kapton, or just formed of a higher-conductance trace such as a conductive thread and/or printed Kapton) to an SMS and/or sensor module. The SMS and/or sensor module may determine, e.g., based on the quality of the signal, which of the redundant traces to use/present for the ECG signal.

For example, in FIG. 21A-21D, the electrodes 2103 are formed as a series of electrodes constituted by ink circles positioned in the standard points of the 12-lead EKG. On a garment (to be worn on the torso), the electrodes may be placed so that when the garment is worn the redundant (pairs) of chest electrodes are positioned corresponding to the V1-V6 positions:

TABLE 1 position of chest electrodes

| Electrode | Placement |
| --- | --- |
| V1 | 4th Intercostal space to the right of the sternum |
| V2 | 4th Intercostal space to the left of the sternum |
| V3 | Midway between V2 and V4 |
| V4 | 5th Intercostal space at the midclavicular line |
| V5 | Anterior axillary line at the same level as V4 |
| V6 | Midaxillary line at the same level as V4 and V5 |

Similarly leads may be placed at other locations on the shirt to measure the RL, RA, LL and LA leads (limb leads), corresponding to:

TABLE 2

Limb lead positions

| Electrode | Placement |
| --- | --- |
| RL | Anywhere above the ankle and below the torso |
| RA | Anywhere between the shoulder and the elbow |
| LL | Anywhere above the ankle and below the torso |
| LA | Anywhere between the shoulder and the elbow |

FIGS. 21A-21B show the limb leads 2105, 2107 for the legs positioned at the lower edge of the torso garment, which may be used even not wearing a separate pant. The limb leads in the garments shown in FIGS. 21A-21B and 21C-21D do not include redundant electrodes, however they may.

In any of the ECG-sensing garments, the electrodes may be held against the body for consistent/constant measurement (even during motion) by the structure of the garment, including by an additional harness region 2144 (e.g., yolk region), as shown by the shaded region in FIGS. 21A and 21C. This harness may be formed as a region supporting the ECG chest electrodes that is relatively more supportive (e.g., applying pressure/force) to hold the chest electrodes on/against the body, even during respiration and other body movements. For example, the harness region may be formed as an elastic corset (e.g., width: 2 cm on the sternum, 4 cm on the xiphoid line) running along the sternal line, then separating on the right and left sides of the xiphoid line, then on the back, then converging on the spinal cord and running up to the neck, then again separating into right and left sides around the neck, to finally converging on the sternal line. The material of the corset has to be extremely extensible.

The electrodes, and/or the region peripheral to the (e.g., chest) electrodes may include a silicone surface that helps hold the electrode(s) against the chest, and may also prevent the electrodes from slipping. For example, silicone may be located in an inner surface of the shirt, corresponding to the harness/corset position, along the horizontal line on both sides up to 5 cm beyond the midaxillary lines. This silicone may help ensure that the ink electrodes are fixed to the chosen position and do not move with patient's motion.

As mentioned, it is particularly helpful that the electrode include adjacent redundant electrodes. All of the electrodes (including the redundant electrodes) may be connected to the SMS and/or control module to detect ECG signals and the SMS and/or control module may decide which of the redundant signals to use (or in some variations to use the redundant signals to improve the overall signal quality, e.g., by selective filtering, averaging, or the like). In some variations the non-selected redundant signal may be ignored; in other variations the apparatus may be configured to store it for later analysis. Both pairs (or more than 2) of electrodes may have signals that may be stored, transmitted and/or processed; decisions about which of the redundant electrodes to use to generate an ECG may be made later.

Sleep Monitoring Garment

Also described are garments configured to be worn to monitor a subject's sleep. Sleep monitoring may generally be used to measure sleep motion, respiration during sleep, body temperature (both core and regional), eye motion, and the like. Such indicators may be used to determine the sleep stage, sleep quality, sleep duration, etc. Any of the garments described herein may be adapted to determine sleep indicators and may therefore be worn while sleeping. Thus, these garments may be comfortable and adapted for use by a sleeping person.

Figure 22B:
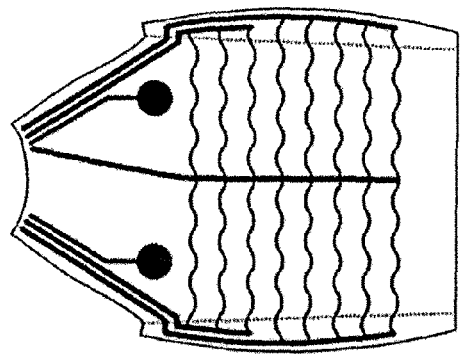
FIGS. 22A, 22B and 22C show front, side and back views, respectively of a garment configured to be worn during sleep to monitor a subject's sleep.
Figure 22A:
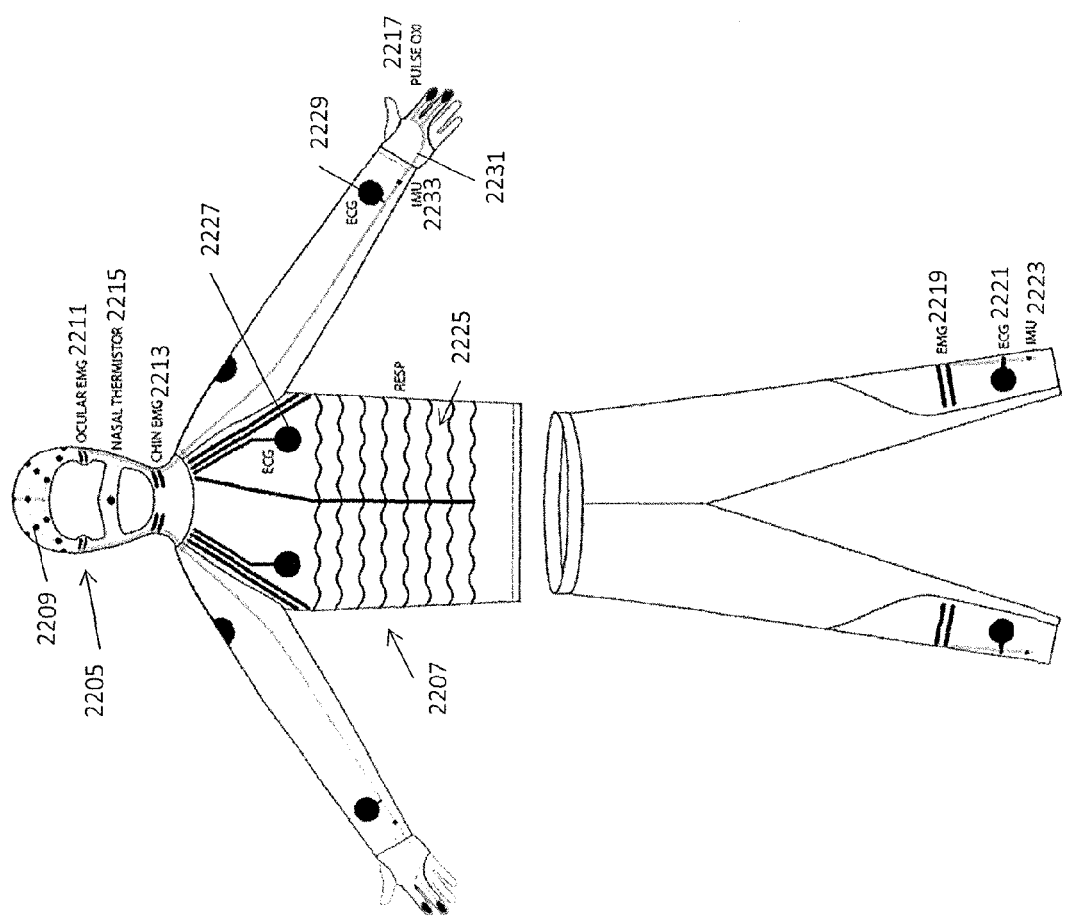
Figure 22C:
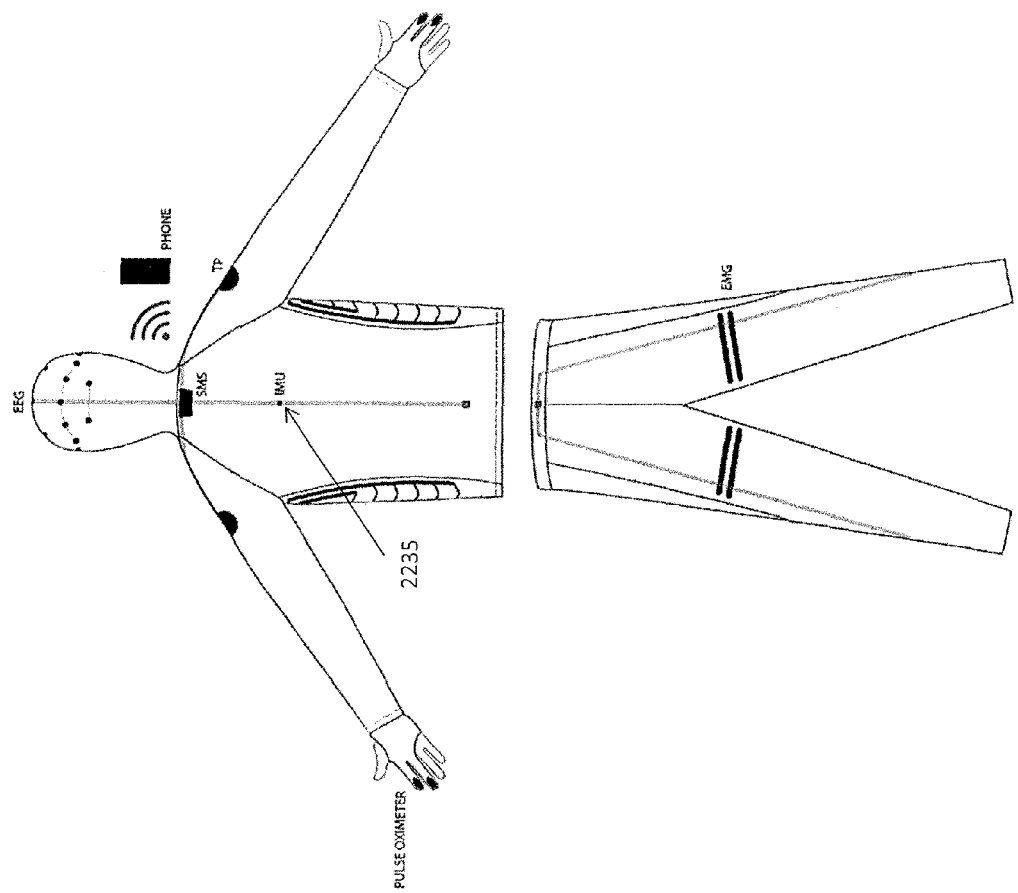

FIGS. 22A-22C illustrate one variation of a garment that may be formed as described herein and may include a plurality of sensors for determining sleep parameters. For example, in FIG. 22A, the front of the garment is shown, including a head cap/hood 2205 with sensors 2209 arranged to determine EEG (scalp electrodes on the inner surface of the hood), facial/ocular EMG (to detect eye movement), a nasal thermistor (detecting respiration) and chin EMG (detecting jaw motion, etc.). The hood may be integral with the shirt 2207 or it may be separately attached thereto. In any of the garments the various components (e.g., shirt, hood, gloves, pants, etc.) may be optional; individual garments or groups of garments may be used. The shirt may be similar or identical to the respiration and/or ECG sensing garments described above. In FIGS. 22A and 22B, the torso region include regional respiration sensors 2225 (stretchable conductive traces) for the anterior and lateral regions of the body, as well as EGC electrodes 2227 (though not all of the V1-V6 lead electrodes are included). The garment may also include pants including limb leads 2229 (for ECG detection) and/or EMG sensors 2219 to detect leg movement/twitch. Full or partial gloves 2231 may also be included and may measure blood oxygenation 2217 (e.g., pulse oxygenation) at the extremities (e.g., fingers).

The SMS and/or sensor module may be adapted to process and/or analyze the sensor inputs and to provide a report on the sleep status (or status over time) for the individual wearing the garment.

In general, these devices may be useful for a sleep lab or home sleep lab. They can record all of the signals usually included in polysomnogrpahic analysis, including respiration, e.g., in a simplified way; only on the anterior and lateral part of the shirt; rib cage and abdominal part, 4 quadrants, may be needed to know when you have paradoxical motion. It is helpful that you have both upper and lower, but may also help to have right/left as well. The use of ECG in the upper part of the torso with a simplified (e.g., 2 electrodes and the wrists and legs) configuration is also helpful. The garment's sensors may again include redundancy as discussed above to have the best and most reliable ECG. In particular, heart rate is used, which may not require a full ECG. EMG recordings (electromyographic electrodes) may be formed of a stretchable conductive ink pattern and may be located in different positions. For example, on the chin, the lower (muscle 2213), which may be helpful for use in polysomnogrphic MG. In addition, ocular EMG 2211 may be helpful for detection of REM and other sleep stages. As mentioned a themister 2215 (temperature sensor at the level of the nose) may be used to detect airflow through the nose, similar to what is done with typical sleep lab sensors. IMUs 2223, 2233 (inertial measurement units) may be used on the arms and legs to detect limb motion. Also, an IMU 2235 may be located on the back of the garment, which is useful for detecting the patient's position (rolling over, supine, prone, on side, etc.), and may detect restlessness.

Wearable System for Detection of Emotion

Also described are garments configured to determine a wearer's emotional state. Self-reported emotional state tends to be inaccurate, subjective, and therefore limited in use. Garments that may include sensors detecting various parameters (both voluntary and involuntary parameters) may be used to determine a subject's objective emotional state.

Figure 23A:
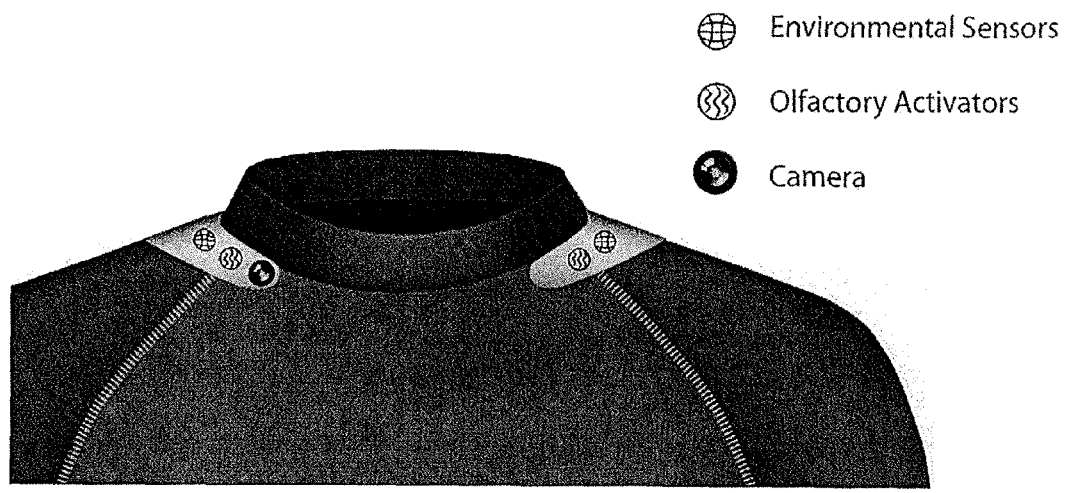
FIGS. 23A and 23B show a front and back view of a collar that may be included.
Figure 23B:
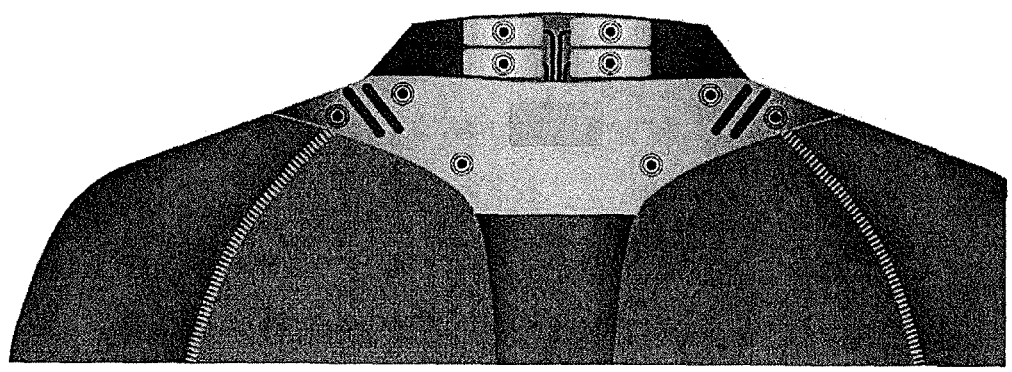

A garment may include a plurality of sensors (as described below and illustrated in FIGS. 23A-23B illustrate a collar that may be included as part of the garment and includes a plurality of sensors (any of which may be included or omitted) to detect parameters indicative of a wearer's emotional state. Sensors may include, for example: environmental sensors (detecting environmental temperature, humidity, etc.), camera(s) for visual detection, including light levels/intensity, audio detectors (e.g., detecting user voice volume, tenor, etc.). The collar may also include any of the other sensors mentioned herein and incorporated by reference (motion sensors, position sensors, acceleration sensors, etc.). In addition, the collar may include one or more outputs (haptic outputs) to provide output, including feedback, to the wearer. Haptic outputs may include olfactory (scent emitting) outputs, tactile output (vibration, pinch, etc.), and the like. The collars described and shown in FIGS. 23A-23B may be configured as an emotion communication receiver (ECR).

Any of the garments for detecting/monitoring emotion may include an ECR. An ECR may sits around the neck. In FIGS. 23A-23B the ECR is a collar that extends from the back, spreading above left and right trapeziuses, extending to the front lateral left and right sides of the neck without reconnecting on the front to facilitate the 'sliding' of the head through the collar of the 'device'. The receptor in the ECR (collar) may house a communications/analysis module (sensor module) and may include connectors (e.g., female and male connectors) as well as sensors, haptic activators and mechanisms generating pressure, vibration, temperature-changes, tensing & relaxing inputs, olfactory-inputs, etc. The front side of the activator also houses smell and taste inducing activators as well as environmental sensors to determine the quality of the environment.

The ECR may transduce received communication of physiological measurements into physically embodied messages. As an example, a friend may send to the user (wearer) of the device her emotional state as measure by her device: the user's ECR may transduce the communication into a sensorial message such as a salute by applying pressure to his shoulders. Users may exchange sensorial messages such as salute touching the shoulder, hug, push, caress, cheer up, relax, etc. and have the option to respond, including: i) Ignore; ii) accept and salute back (with their own message); iii) reject (electrical discharge). Users can choose how to receive the messages between a) pressure (wide), b) pressure (narrow-puncture), c) pressure-message (Morse-like), d) vibration, e) temperature change, or the like (including combinations). Users may also choose not accept the "emotional" valence messages to preserve her/his privacy and/or may provide a feedback to improve the accuracy of the emotions-interpretation language.

Systems for Detection, Interpretation, Transduction, Communication, and Perception of Emotions ("DITCRE")

For example, a garment (including the collars, shirts and the like) described herein may be configured as a DITCRE garment. The schematic diagrams shown in FIGS. 24 and 25A-25E illustrate how the DITCRE may be implemented in a garment, including a collar as shown in FIGS. 23A-23B.

The garments adapted to detect, deduce, and/or determine (derive) emotional state, and allow actions based on the derived emotional state may be used to control feedback, which may be useful in training, meditation, or learning tasks, and it may also be useful in communication with others. Thus the derived emotional state, which may be derived generally from analysis of multiple sensors worn by the user, over time, may be used to provide output. Such communication may generally be more truthful and intimate, in part because the interpretation of the emotional state is based on detected, rather than exclusively self-reported, parameters, as well as the use of different sensing modalities. A wearer may choose when and/or which emotional status they would like to communicate, and particularly with whom they wish to communicate. Any of the garments may include an output or outputs (e.g., haptic outputs) detected by the wearer, as described above. For example, haptic coding may be used to communicate even without verbal/written communication. For example, the haptic coding may be transmitted to/between wearers using a Morse-type code. In general, the haptic activators may be positioned in body regions/locations where sensitivity and emotional response is greatest (empirically determine for a specific user, or generally determined from a population of users), to optimize the location of the haptic activators.

Thus, the garments described herein may add an additional dimension when communicating, including in particular communicating between wearers. For example, body "language" may be interpreted by the sensor module and may color output from the garment or communications from the garment. The garments may also be adapted to provide feedback, comments that may have therapeutic impact on the wearer, including identifying and treating depression and the like.

In use, these garments may also provide interpretation of a subject's emotional as well as expressive output. For example, the garments may aid in interpreting across cultures/languages. Just as there are spoken languages, non-overt communication (gestures, body language, etc.) may also provide cues that he apparatus can use and express as part of a subject's output or to be received by another user.

As mentioned above, in FIGS. 23A and 23B, the collar sits around the neck, extending from the back, above left and right trapeziuses, and extending to the front lateral left and right sides of the neck without necessarily reconnecting on the front, to facilitate the 'sliding' of the head through the collar. The receptor may house a Sensors Management System (SMS), female and/or male connectors as well as: sensors (e.g., EMG sensors over left & right trapezius as additional parameter to evaluate user's emotions, such as levels of stress or relaxation; olfactory sensors as additional parameter to evaluate user's emotions; environmental sensors to determine the quality of the surrounding environment, toxicity, etc.); haptic activators and mechanisms generating pressure, vibration, temperature-changes, and the like. These sensors may communicate a user's or other user's emotions, may convey relaxing and tensing inputs as 'massages', or relaxing therapy to the user.

In some variations the garment also includes one or more olfactory activators (e.g., scent & odor reproducing activators) and taste activators placed on the front left and front right side of the ECR as an additional means to communicate user's or other users' emotional states; one or more camera (e.g., placed on the right -or left-front side of the ECR) which may be adapted to determine facial expressions as an additional parameter to evaluate other people emotions, and/or evaluate environment. The collar may also include speakers to share music and messages with surrounding people.

An ECR may be connected and can be activated and managed through the Touch Points previously described (intentional touch regions on the garment). An ECR may receive input from the Sensor Management System, including evaluations of the user state translated into two or more emotional valences or states (e.g., 8 emotional states). The number and the classification of such states may vary in the future). Examples of emotional valences may include: acceptance, anger, anticipation, disgust, joy, fear, sadness and surprise. Emotional valences may be communicated back to the user and/or to third parties (as controlled by the user). Emotional valences may help a user to better understand their own emotions and may help communicate their emotions in a commonly shared classification to their friends.

The ECR may generally help transduce physiological measurements (e.g., ECG, Skin Conductance, EMG, respiration, etc.) and 'evaluations' (e.g., facial expression, posture, gesticulations, motor behaviors, voice tones, eyes-sleepiness or alertness, movements, actions, etc.) into intelligibly qualified emotions. The EMG may also help communicate those emotions through voice, physically embodied messages or visual displays. As an example, a friend may send her emotional state as measured by her garment: the user's may transduce the communication into a sensorial message (such as a salute, by applying pressure to his shoulders; a scent or a taste emitted a haptic describing her emotional state, a color describing her emotional state, or an audio or visual description of her emotional state. Users may exchange sensorial messages such as salute touching the shoulder, hug, push, caress, cheer up, relax, etc. and may have the option to respond. For example, a user may ignore, accept and salute back (with their own messages), and/or reject (electrical discharge). A user may also choose how to receive the messages between a) pressure (wide), b) pressure (narrow-puncture), c) pressure-message (Morse-like), d) vibration, e) temperature change, f) audio description, g) visual description, etc. A user may control the communication exchange and can choose not to accept the emotional messages to preserve her/his privacy. This communication modality (including the use of the haptics) recognizes that other, not limited to aural or visual (spoken/written) modalities such as touch may be more effective (or differently effective) when communicating emotional content/context. Thus, any of the garments described may transduce a user's physiological measurements into intelligible communication, including communication of the user's emotional valence. A user may choose the format (e.g., different forms of touch, audio, graphs, drawings, numbers, etc.) of communication data. For example, the garments may allow a user to transduce the users' physiological measurements (emotional valence) into voice, physically embodied messages or visual displays (display or touch screen on forearms, on glasses or on smartphone) to other users. Further, the garments, and particularly those with ECR may allow a user to improve the accuracy of the emotions-interpretation language by enabling them to provide feedback on data evaluation, representation and communication.

An ECR system may also act as a self-improving system (much like voice-recognition most advanced systems): the more users will express and communicate their emotions the more accurate emotions qualification, description and communication will be. In addition, the user may activate and interact with the system through touch points on the garment.

ECR may be used in a variety of contexts. For example. ECR may be used as a lie detector. Typically, lie detectors detect changes in body functions that are not easily controlled by the conscious mind and may include bodily reactions like skin conductivity and heart rate; they also may consider respiration rate, blood pressure, capillary dilation, and muscular movement. These measures may indicate a short-term stress response which can be from lying or significance to the subject. Problems arise because they are also associated with mental effort, and emotional state; so they can be influenced by fear, anger, and surprise for example. The EDR systems described herein, which may be used for long-term monitoring and training/conditioning of a user, may be better at distinguishing such responses from artifact responses.

ECR may also be used for safety evaluation, such as environmental safety, examining air (level of pollution, toxicity, etc.), water (no drinking, no swimming, etc.), soil; examining locations, e.g., searching risk in surrounding areas, such as crime reports in the area, avalanches, flooding, trees falling, toxic area; indicating functions based on time of the day, time of the year, etc., such as recurring events like parades, etc. The ECR may also monitor user behavior and provide data/feedback on such behaviors (e.g., eating, drinking, substance abuse, etc.). A garment with ECR may also assist and/or provide feedback on traveling, such as driving (driver behavior, driver's track record, surrounding traffic, type of road, weather conditions), flying, sailing, or otherwise operating machinery/vehicles.

Finally, a garment with or without ECR may be helpful for safety actions: a) emergency calls: 911, doctor, GPS tracking, family member monitoring/tracking, coaching; b) provide relevant information: type of danger, location, user's physiological data, user's medical and relevant data, user's emotional data, health insurance, financial profile, and the like. The garment (with our without ECR) may also be more interactive, providing suggestions on health, including activity level, eating, and the like, or on emotional wellness.

As described in FIGS. 25A-25E, the ECR may perform measurements and evaluations based on one or more of: physiologic (measured through sensors) information, gestures (e.g., IMUs and accelerometers on wrists), posture (e.g., IMUs on module, each shoulder, mid spine, lower spine), motor behavior (e.g., IMUs on each ankle and each wrist), speech evaluation (e.g., recording voice), facial Expressions (e.g., sensors on ears, forehead and neck for self, video camera for other persons), scents or odors (e.g., chemical sensors), EMG, and/or EEG sensors, and/or evaluation of the environment (e.g., temperature sensors, pollution sensors, etc.).

Figure 24:
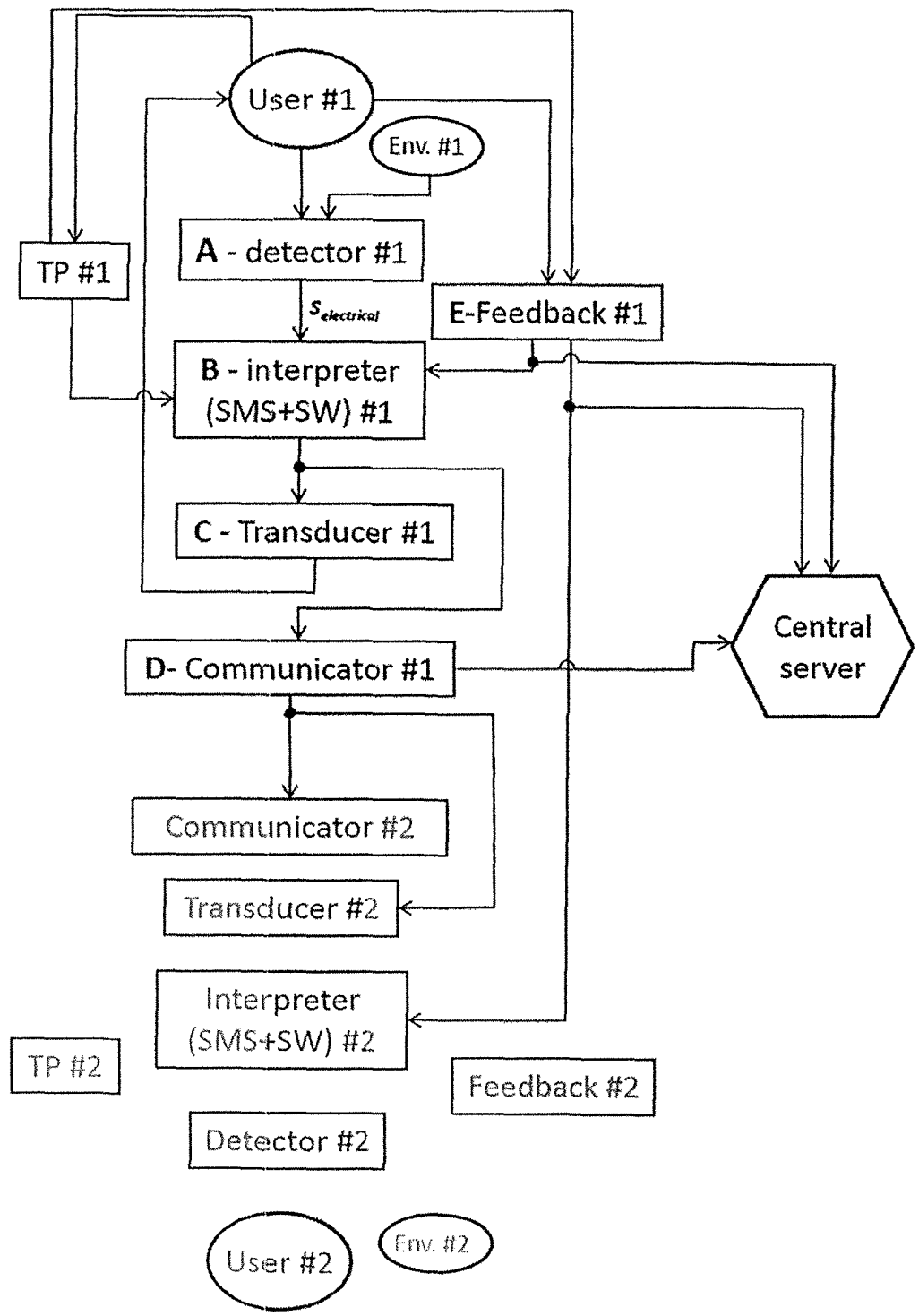
FIG. 24 shows a schematic view of operation of a garment (or multiple garments) adapted for determining emotional valence.

For example, FIG. 24 outlines a pair of users that may interact, each with a garment adapted for detection, interpretation, transduction, communication, and perception of emotions. Each of these areas (labeled A-D) are described in greater detail in FIGS. 25A (detectors, including sensing devices), 25B (interpretation of the sensor data to determine an emotional valence), 25C (actuators and communication, including output of valence information from the user or another person using a similar device), and 25D (feedback).

Such apparatuses may find use with the general population, including people interested in monitoring their well-being status during their daily regular activities (walking, eating, working, seating in front of their computer . . . ), and also for athletes who want to monitor their fitness level during their training or specific sports. Participants (users) may be required to register and fill a list similar to the one filled in hospitals or by professional athletes: the more questions the participant responds the more accurate their evaluation will be.

Figure 25A:
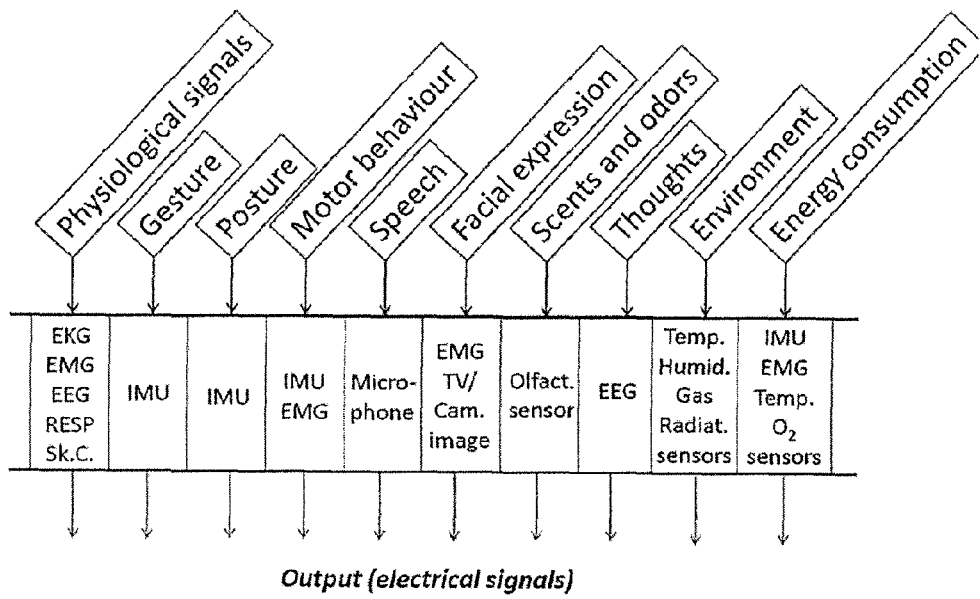
FIGS. 25A-25E are schematics providing further detail from the schematic shown in FIG. 24.
Figure 25B:
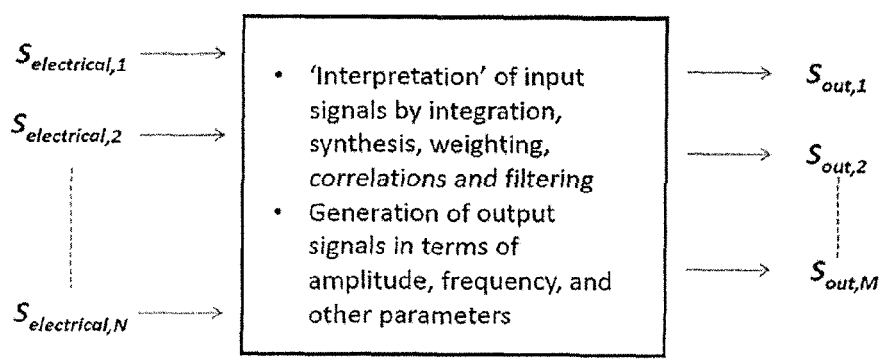
Figure 25C:
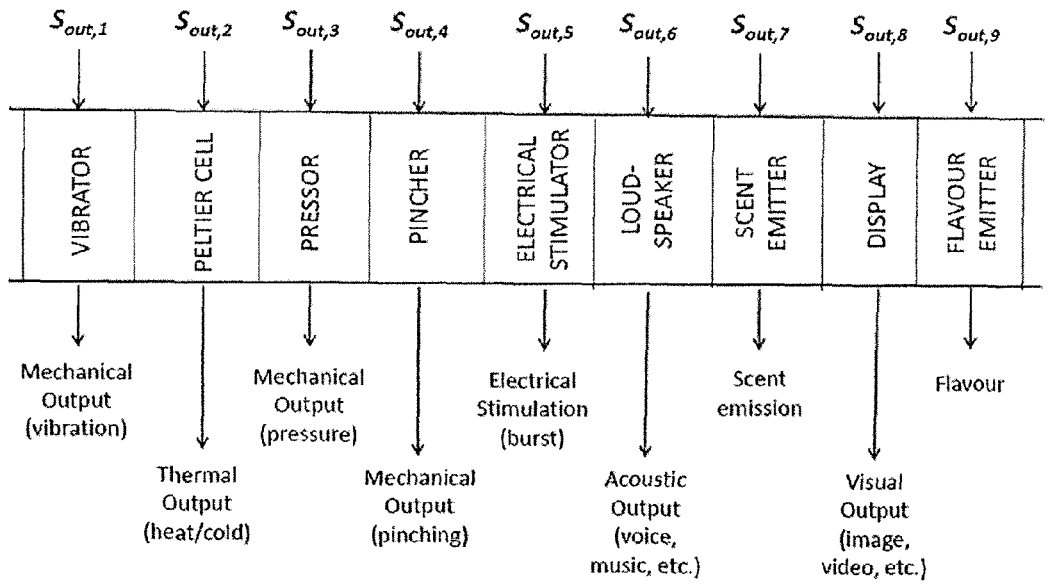
Figure 25D:
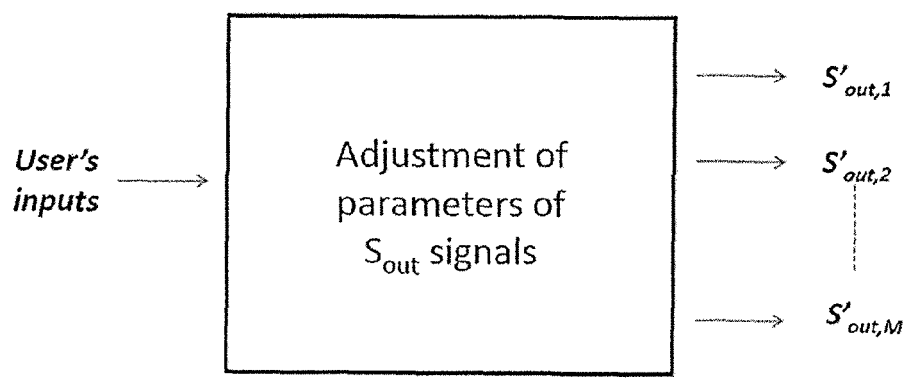
Figure 25E:
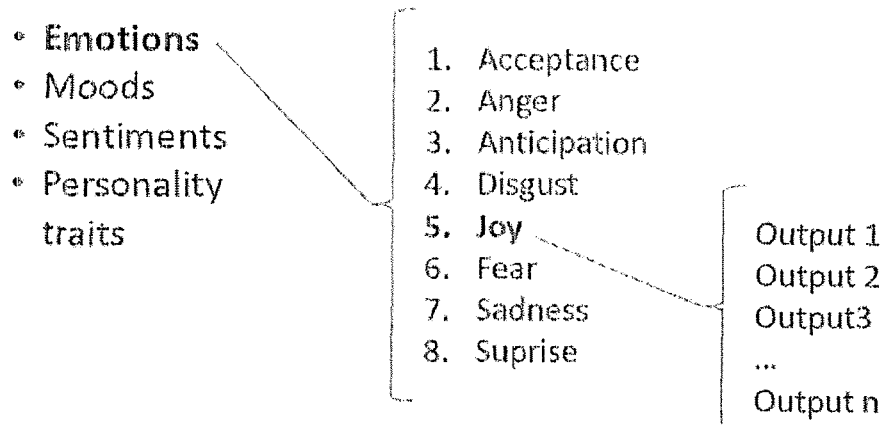
Figure 26:
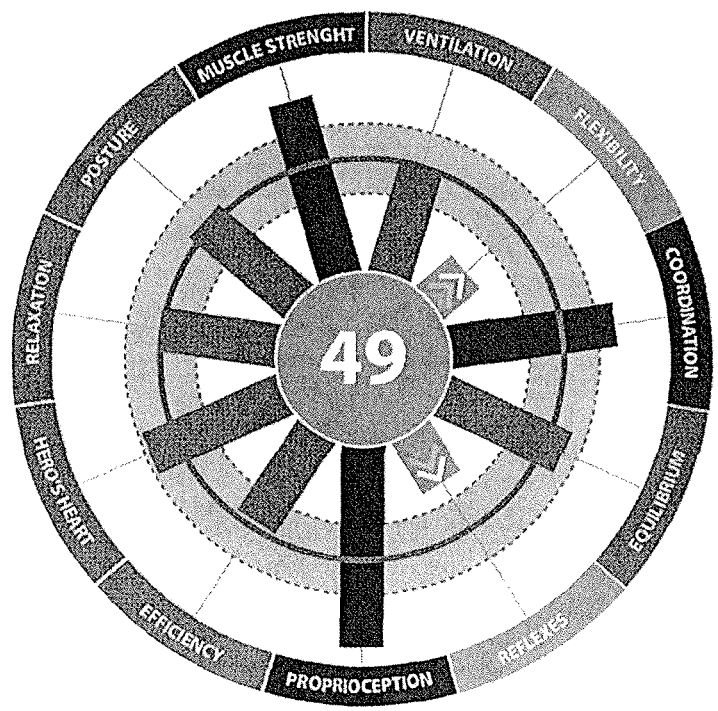
FIG. 26 is a graphical illustration of a determination of well-being that may be made from a user wearing a garment as described herein.
Figure 27:
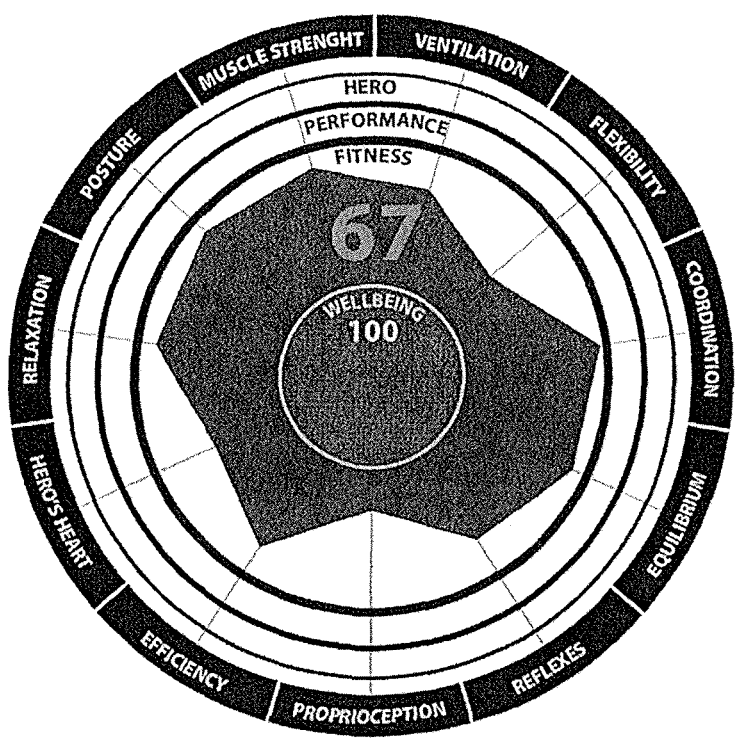
FIG. 27 is a graphical illustration of a fitness ranking/analysis that may be made from a user wearing a garment as described herein.

FIG. 25E illustrates one method in which an emotional valence may be determine for a particular user, based on the inputs of various sensors, and may also include feedback specific to a particular user. In addition, FIGS. 26 and 27 illustrate graphically how an ECR may operate to determine from the subject their actual emotional valence or an overall estimate of "well-being" (FIG. 26). Similarly, the sensors may be used to provide the user an indicator of overall fitness (FIG. 27). These charts may provide an evaluation that can be presented graphically, as shown in FIGS. 26 and 27, providing a snapshot of the wellbeing of a person or the fitness level of an athlete. The evaluation may be based on a number of parameters (e.g., that can vary in number, such as from 8 to 20 or more depending on the number of sensors in a given device). Each graph may provide: (1) a value that synthesizes the well-being or the fitness level of the user based on an adjusted synthesis of all the parameters; (2) a value that synthesizes the well-being of the fitness level of the entire population (given in absolute number and % of the number) so that the users will immediately know if she is above or below average. This value increases in accuracy with the number of users; (3) the value may be adjusted to the person specific needs. For example, since 30% of people above 65 fall and get injured for lack of equilibrium, a 70 year old person's equilibrium may be given a higher relevance then for a 40 year old person. Similarly, a self-identified weight lifter's strength may be given a higher relevance then for a tennis players, or endurance a higher relevance for a super triathlon athlete then for a slalom skier. A user can thus use this sort of graphical output to see her value and the total population value for each one of the parameters. A user can further go into the details for each parameter. For example, the efficiency score, compared to the population's efficiency score; how efficiency is calculated; the biometrics involved into the calculation; the accuracy of the calculation considered the state of the technology on hand; the medical accuracy, etc.

A user who chooses to improve a given parameter (say equilibrium for a 70 year old) may be given a list of exercises to do it (jump rope, one leg stand. etc.). A haptic feed-back may be used to tell the user when her equilibrium is below or above average, and/or an improvement indication, and/or a session's performance versus best personal performance.

The many sensors and haptic actuators in an apparatus maybe adapted to allow a user to communicate (e.g., through audio, haptic or visual messages) to other users while they are exercising in order to maximize their efficiency, improve their execution. For example: a) communicate if athlete is not wormed up when starting exercising; b) if temperature is too cold when finishing the exercise; c) if the posture or body position is not appropriate when performing the exercise; d) if the user his overloading his muscles; e) if the athlete is not pushing enough during the training session.

Stretchable Conductive Ink Patterns

Any of the apparatuses described herein may include a stretchable conductive ink pattern. In general, the stretchable conducive ink may have a stretchability ranging from 5% to 200%, e.g., it may be stretched more than 1 times (100%) of its at rest length without breaking. In some examples the stretchable conductive in can be stretched to more than 2 times (200%), more than 3 times (300%), more than 4 times (400%), or more than 5 times (500%) of its neutral, at rest length. The stretchable conductive ink patterns are conductive, having a low resistivity. For example, the bulk resistivity may be between 0.2 and 20 ohms*cm (and the sheet resistivity between about 100 to 10,000 ohms per square). The conductivity may be dependent upon the stretch, although it may stay within the ranges described above (e.g., between 0.2 and 20 ohms*cm).

Structurally, any of the stretchable conductive ink patterns described herein are typically made from a specified combination of an insulative adhesive and a conductive ink. In general, a stretchable conductive ink pattern includes a first (or base) layer of insulative and elastic adhesive and a layer of conductive ink, where the conductive ink includes between about 40% and about 60% of conductive particles (e.g., mica, carbon black, graphene, graphite, silver metal powder, copper metal powder, or iron metal powder, etc.), and a gradient region or zone between the insulative, elastic adhesive and the layer of conductive ink. The gradient region is a combination of the conductive ink (e.g., conductive particles of the conductive ink) and the adhesive, in which the concentration of the ink (e.g., conductive particles) may vary with depth. In general, the gradient region may be a mixture of the conductive ink (e.g., conductive particles) and the adhesive wherein the concentration of conductive ink in the gradient region may be less than the concentration of the conductive ink in the conductive ink layer. The gradient region may be a continuous gradient of conductive ink (particles), e.g., it may be nonhomogeneous, or it may be a step gradient.

Typical conductive inks, such as those used for printed circuits and even flexible circuits, are not sufficiently stretchable to be used for garments, including in particular not for compression garments and may break or form discontinuities when used. Surprisingly, the combination of conductive ink, gradient region and insulative adhesive provides a conductive ink composite that is both conductive and highly stretchable/extensible. The composition of the conductive ink that may be used in as described herein generally includes: between about 40-60% conductive particles, between about 30-50% binder; between about 3-7% solvent; and between about 3-7% thickener. Further, the use of an intermediate, "gradient" region between the insulating adhesive and the conductive ink layer(s) has also been found to be important.

The conductive ink used and combined with the adhesive to form the conductive ink pattern typically has a low toxicity and hypo-allergenicity (e.g., a formaldehyde concentration lower than 100 ppm), and a resistance to damage from washing, including preservation of electrical and elastic properties following repeated washing cycles.

Figure 28A:
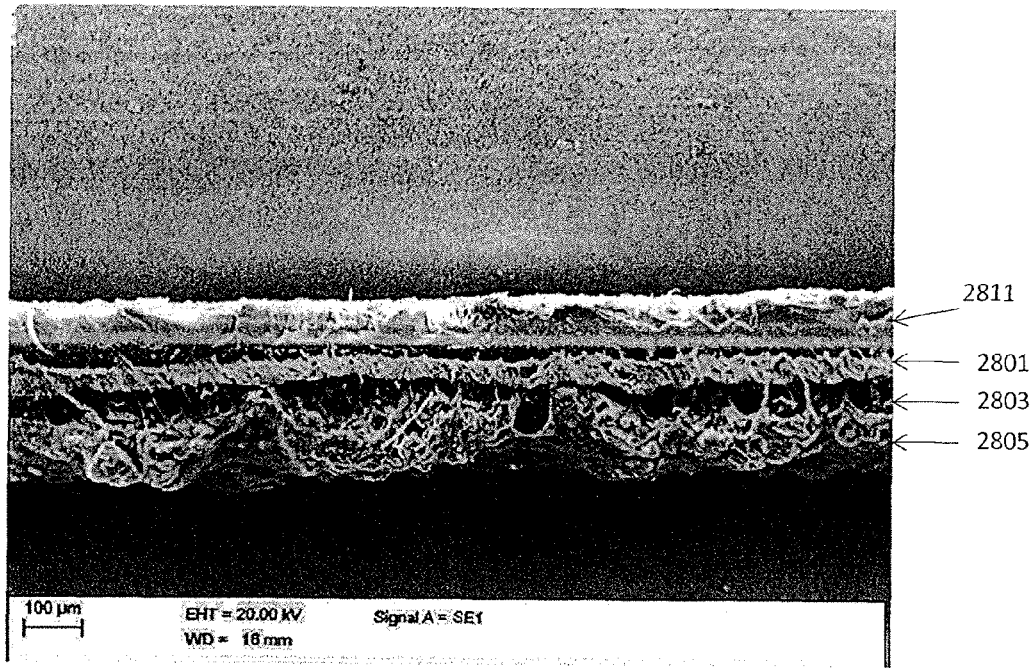
FIG. 28A is a scanning electron micrograph (SEM) of a section through one example of a stretchable conductive ink pattern, illustrating the conductive ink layer and an elastic adhesive layer with an intermediate gradient region between the two.
Figure 28B:
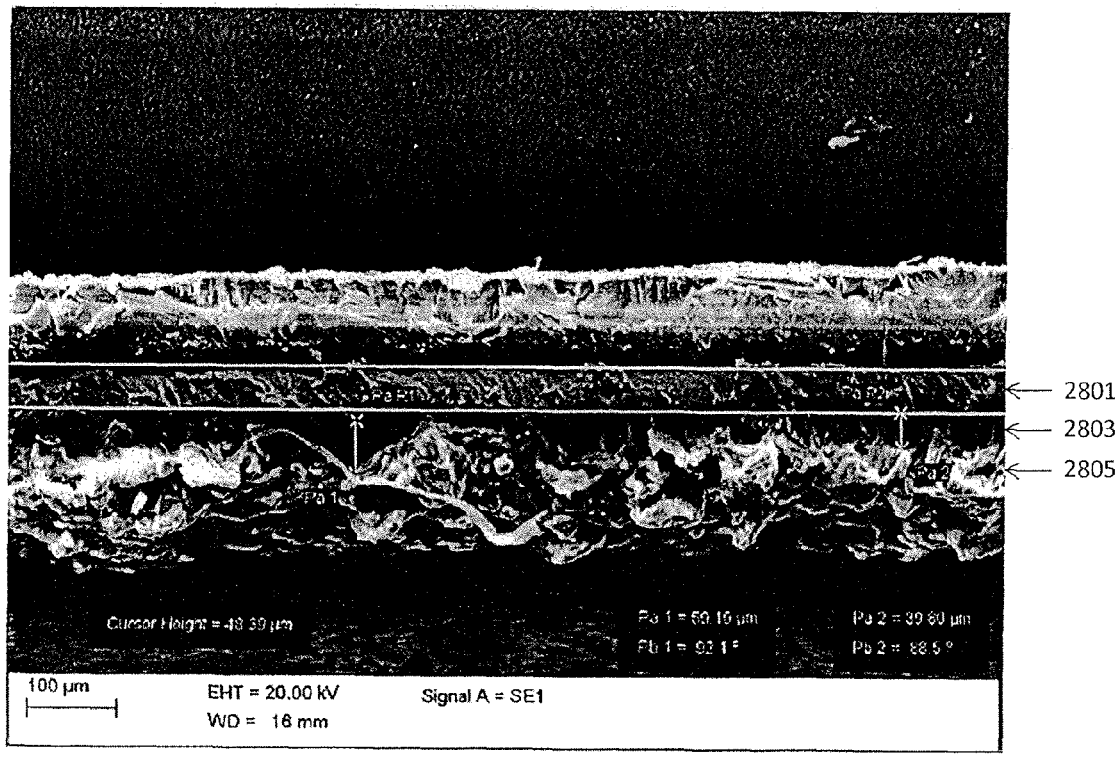
FIG. 28B is another SEM of a section through an example of a stretchable conductive ink pattern, showing the thicknesses of each region/layer.

For example, FIGS. 28A and 28B show electron micrographs (scanning electron micrograph, SEM) of a sample of a conductive ink pattern placed between two supports of aluminum. In FIG. 28A, the lowest layer 2805 is the adhesive, the layer adjacent and above that is the gradient region 2803, and the layer adjacent to and above that is the conductive ink 2801. In this example an additional insulative layer (resin 2811) is placed on top of the conductive ink. In general, the conductive ink may be formed of multiple layers of applied conductive ink. In FIG. 28A the conductive ink layer was formed by sequential application of 5 layers; these layers are not visible in the micrograph.

In FIG. 28B, an electron micrograph was used to quantify the thickness of the layer. In this example, the conductive ink layer 2801 (region) has a thickness of about 50 µm, the gradient (transition) zone 2803 has a thickness of between about 40-80 µm, and the glue 2805 has a thickness of about 150 µm.

The gradient region may be functioning both to enhance the stretchability of the conductive ink, as well as enhancing the stability of the conductivity. Electrical conductivity is allowed by the upper region, while the high degree of mechanical stretching allowed (due to the adhesive) is enhanced by the lower layers. The incomplete mixing of the conducive ink and the adhesive found in the gradient region appears to result in a structure and composition that can be repeatedly stretched and released, while retaining the conductivity. Note that the resistivity of the composite may change with stretch (generally increasing resistivity with stretch), and this property may be used to detect stretch.

In general, the gradient region may be formed by combining the conductive ink and the adhesive before either one is completely dried, allowing them to combine to form the transition zone having the appropriate thickness. The composition of the ink (e.g., between about 40-60% conductive particles, between about 30-50% binder; between about 3-7% solvent; and between about 3-7% thickener) may determine the formation parameters of this overlapping (gradient) region. FIG. 29A-29D shows an example of the compositional distribution of an example of a stretchable conductive ink pattern (composite). In FIG. 29A, carbon is shown, and is ubiquitous throughout the layers, as expected for organic materials. In FIG. 29C, the distribution of silicon is concentrated on the surfaces of the substrate (a plastic substrate onto which the conductive ink pattern is made), and diffuse in the conductive ink pattern. Similarly in FIG. 29D the oxygen is diffused everywhere. In contrast, as shown in FIG. 29B, sulfur is concentrated in the ink but not the glue. The gradient of sulfur therefore indicates a gradual transition from the ink to the glue in the area morphologically similar to the glue. This region is the gradient zone or region, where non-homogenous mixing has occurred.

In FIGS. 28A-28B and 29A-29C, the stretchable conductive ink pattern is formed on a substrate of polyester paper onto which the ink and adhesive are printed (along with an outer insulating resin). This pattern may then be applied to the garment so that it sticks to the garment and the substrate (paper) can be peeled off that that the ink remains. The adhesive is highly elastic, and allows stretching. The conductive ink, alone, may be somewhat stretchable, but is not nearly as stretchable as the adhesive, perhaps because of the rigid metallic particles. The intermediate region (where the adhesive and the conductive ink are overlapping) is important. Complete mixing in this zone would homogenize this region, and likely reduce the conductivity (as the adhesive is insualtive); the partial mixing may preserve the stretchability while preserving conductivity.

Figure 30:
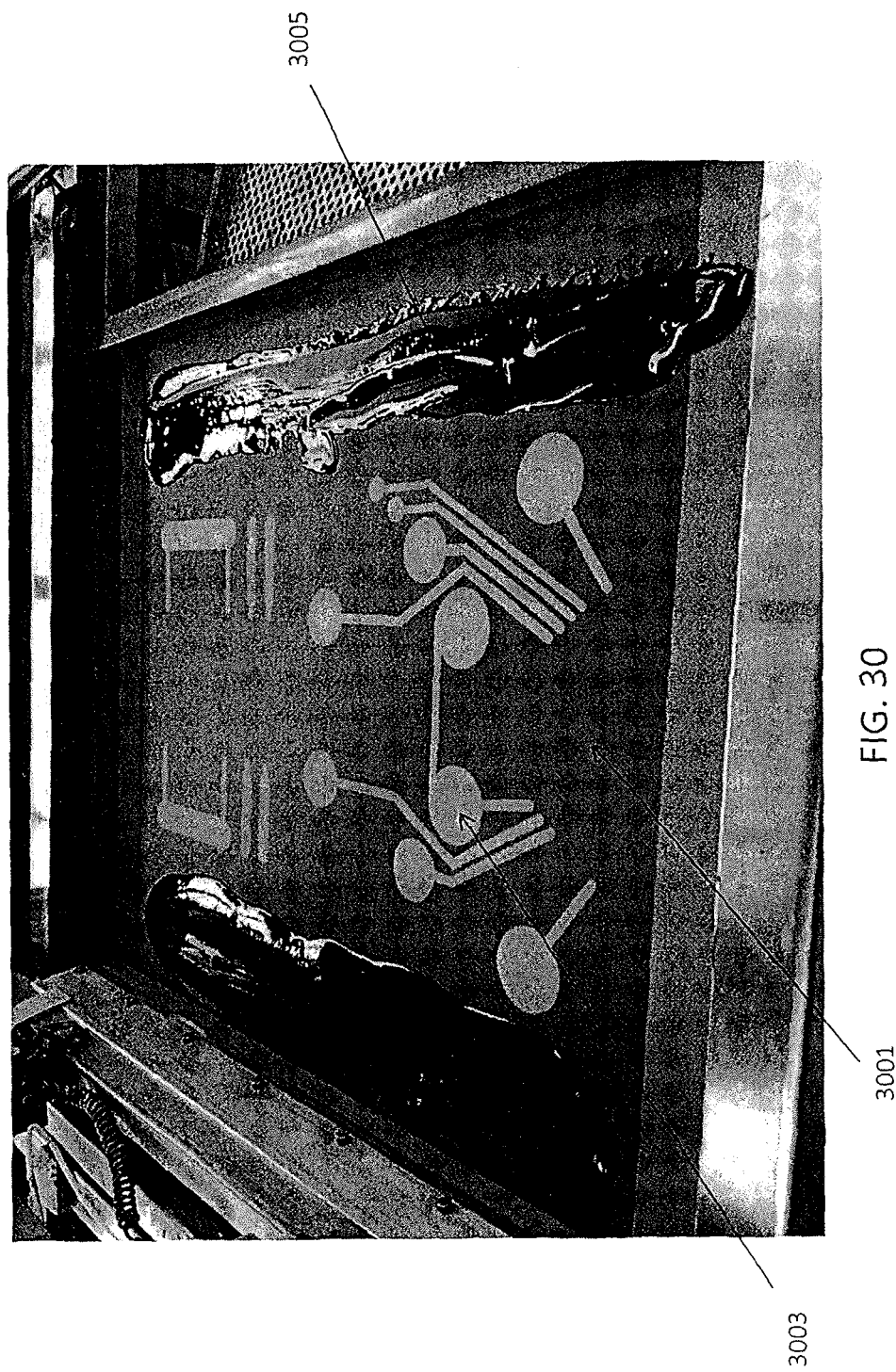
FIG. 30 illustrates on method of printing a stretchable conductive ink pattern onto a substrate.

An outer protective layer that insulates the conductive ink may be included when desired, e.g., when forming conductive traces, or patterning a sensor or electrode, though it may be left off contract regions of an electrode, for example. The resin ("primer") may be one or more layers of insulating material that does not link with or mix with the conductive ink. For example, the resin material may be insulating and may also help protect from detergents and fluids (water) used for washing, as well as protecting from scratching, etc. In some variations the resin is an acrylate (e.g., acrylic resin). Aldehyde or acrylic (synthetic resins) may also be used. Any of the components (e.g., conductive ink, adhesive, and resin) may be applied by printing. For example, FIG. 30 illustrates one example of method used to print the stretchable conductive ink pattern onto a substrate. In FIG. 30, a first mask ("screen") 3001 is used to form the pattern of adhesive (electrically insulative glue) to be applied to the substrate, beneath the screen 3001 (not visible). For example, when applying directly onto a fabric, the adhesive may be applied in a screening process by pulling the 'wet' adhesive 3005 across the screen so that it forms the pattern shown. Multiple applications of adhesive may be applied, or the thickness may otherwise be adjusted (e.g., by the application force, viscosity and/or screen opening size). Thereafter a second screen (or the same screen) may be used to apply the pattern of electrically conductive ink. Multiple applications of conductive ink may be applied to achieve the desired thickness (typically less than the thickness of the adhesive. The second screen may have openings that are slightly smaller than the pattern used for the adhesive, or they may be the same size (or in some variations, larger). The adhesive and the conductive ink may be co-extensive. When applying to a transfer substrate the order may be reversed, so that the conductive ink is applied to the substrate before the adhesive. As mentioned an insulating resin (e.g., protective layer) may be applied adjacent to the conductive ink layer.

As mentioned above, the conductive ink patterns described herein may be any appropriate pattern, including traces (e.g., connecting various elements on the garment). sensors (e.g., touch point sensors, stretch/respiration sensors) or electrodes (EEG sensors, ECG sensors, EMG sensors, etc.). When used as a connector it may be combined with additional conductive connector elements, including, but not limited to conductive threads, conductive traces formed on a substrate such as Kapton, etc. Such combinations of conductive ink patterns and additional highly conductive materials may be particularly useful over longer lengths. In some variations the stretchable conductive ink material may be used as a trace or connector in regions where the garment will be stretched a lot.

Figure 31A:
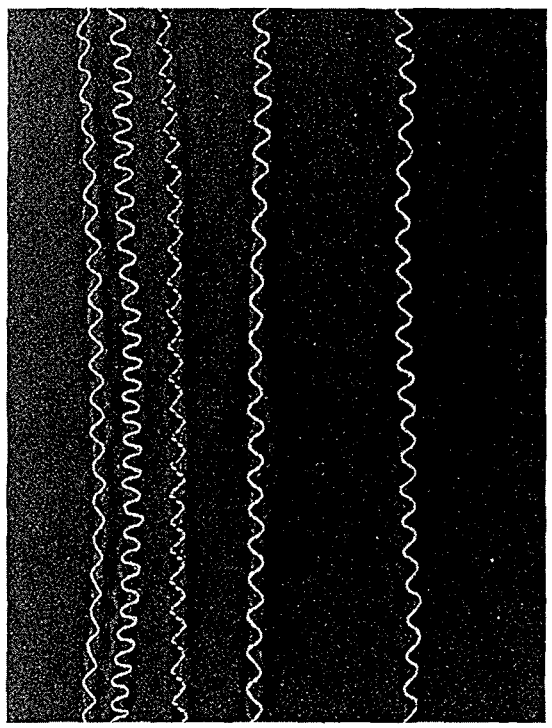
FIGS. 31A-31C illustrate examples of conductive thread sewn into a substrate (e.g., fabric)
Figure 31C:
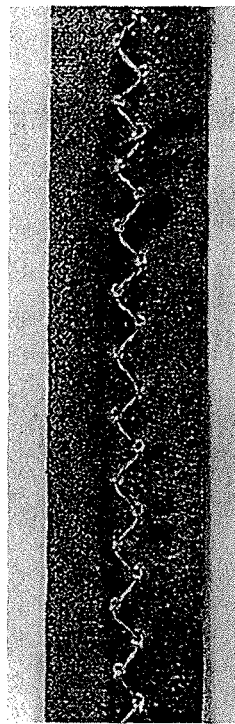
Figure 31B:
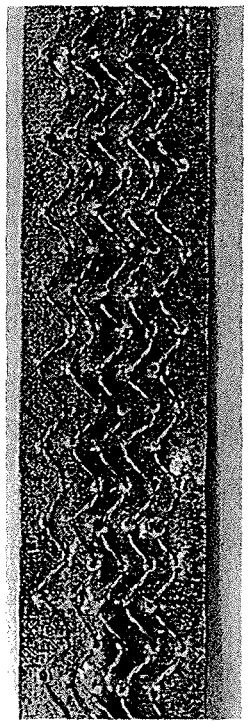

For example, FIGS. 31A-31C show example of conductive threads that are stitched onto a fabric forming a garment that may be used to connect an electrode, sensor or trace formed of a stretchable conductive ink pattern (having an adhesive, gradient region and conductive ink) to a power supply and/or sensing module.

For example in FIGS. 1A, 4, 6A-6C, 13A-13B, 19A and 20A, the touchpoints and the traces connecting them to a sensor module (sensor manager) may be formed of a stretchable conducive ink composite including a layer of adhesive, an intermediate gradient region and a layer of conductive ink; the trace portion may be insulated, e.g., using a protective resin. The electrode forming the touchpoint portion may be relatively large with the connecting trace being smaller. The trace only needs to extend a short distance. Touchpoint sensors are also somewhat insensitive to stretch of the garment/trace that might change the resistivity of the trace, because the signal from the sensor is a binary signal—e.g., touch or no touch. Similarly, a stretchable conductive ink trace (composite formed into a trace) may be used to connect to EKG electrodes. Typically a conductive ink pattern used as a trace may extend up to 30 cm or less (e.g., 25 cm or less, etc.), although longer traces may be used. Thus, for example, a conductive trace formed of a stretchable conductive ink pattern may be as long as or longer than 25 cm, with a width between 2 mm and up to 10 mm (an average of between about 0.6 to 0.5 mm). The length could be extended while remaining within a target conductivity/resistivity by increasing the thickness of the conductive ink pattern. In some variations it may be desirable to keep the length short. Respiratory sensors may be substantially longer, however, and may up to 22 mm wide, for example.

In some variations it may be useful to use conductive threads or other high-conductivity connectors, such as those shown in FIG. 31A-31C. In this example, the conductive thread is stitched onto the garment in a wavy (e.g., zig-zag, sigmoidal, etc.) pattern that allows some stretching in the net direction of the stitching. As described above, respiration (sensors) traces may be formed of stretchable conductive ink patterns to take advantage of the change in conductivity with the change in resistivity with stretching of the conductive ink pattern. In this example, the sewn pattern of threads includes an approximately 35-40 degree zig-zag pattern allowed the stitch to elongate slightly with the fabric. In some example, the conductive thread is a metallic conductive thread. The angle formed at each turning point (in the wavy pattern) and the width of the pattern may depend upon the textile used. In general, the higher the stretchability of the textile, the smaller the angle. The number of threads may vary; in general, any number of threads may be used depending, for example, on the number of sensors and their pins that need to be connected. The threads are typically sewn directly on the garment. The electrical insulation of the thread may be obtained by an external coating on the thread (e.g. silicone, polyester, cotton, etc.) and/or by a layer of insulating adhesive, as described above. The thread connectors may also be used as part of a transfer as described above. For example, a conductive thread may be sewn on a band made on the same fabric of the garment and then transferred by a thermal process to the garment, e.g., using a layer of adhesive.

One or more conductive threads may be applied directly to a fabric (such as a compression garment) or to a transfer (e.g., patch of fabric or other material that is then attached to the garment). Conductive threads may be insulated (e.g., enameled) before being sewn. In some variations the conductive thread may be grouped prior to sewing onto a fabric or other substrate. For example, a plurality (e.g., 2, 3, 4, 5, etc.) of threads may be insulated and wound together, then stitched into a substrate, such as the compression fabric. For example, in one variation, an apparatus includes a garment having an IMU and two EMGs with inputs fed into circuitry (e.g., microchip) on the apparatus, including on a sensor module/manager. The components may be operated on the same electronic 'line', where the line is a plurality of electrical conductive threads that are combined together for stitching through the substrate. In one example, two microchips can be operated by the same 'line' made of 4 wires, where each wire is electrically isolated from each other. In stitching a material, the stitch may be formed of two sets of wires; one on top of the substrate and one beneath the substrate, as is understood from mechanical sewing devices; in some variations a stitch formed of conductive thread may include an upper conductive thread (or group of conductive threads) and a lower conductive thread (or group of conductive threads), where the upper conductive thread(s) is primarily on the upper surface and the lower conductive thread(s) are primarily on the lower surface (but one or either may pass through the substrate to engage with the other).

For example, a conductive thread may include a very fine (e.g., 0.7 millimeters gauge/thickness) 'wire' made of 4 twisted and enameled (thus electrically isolated from each other) wires covered with a binding solution (that is silicon or water based) or protected by a jacket, having a total diameter of about 0.9 millimeters. A conductive wire may be sewn in a wavy (e.g., zig-zag) pattern, such as a pattern having 45 to 90 degrees angles between the legs of the zig-zag, directly on a fabric or substrate. In some example, the pattern is formed on a substrate of material (e.g., fabric) and attached to the garment. For example, the substrate may be a 1 cm to 3 cm self-adhesive strip of fabric.

Sensor Manager/Module

Figure 32A:
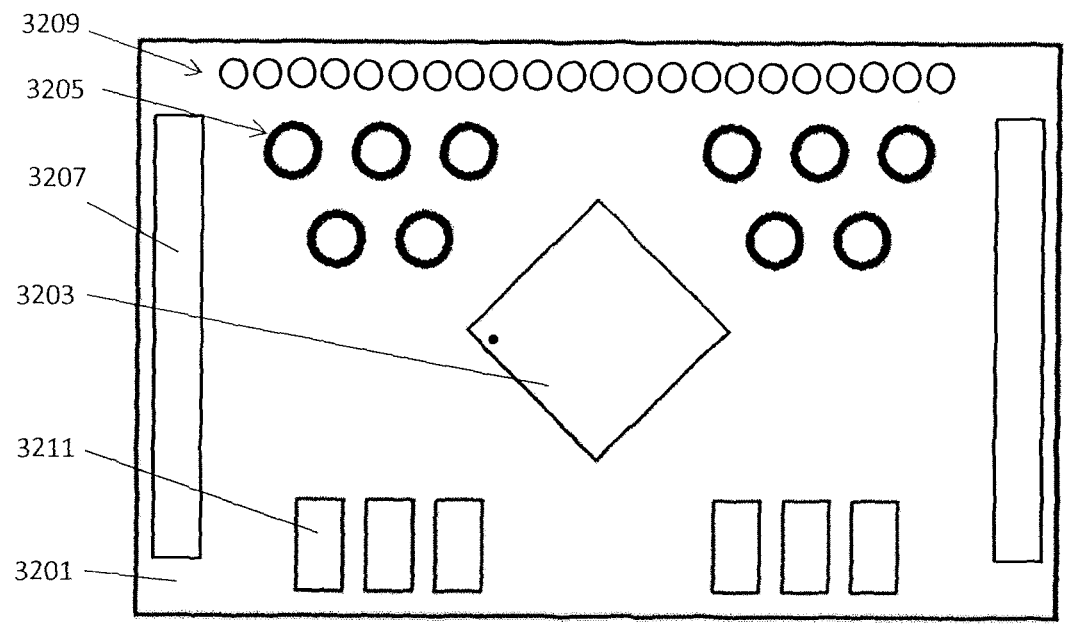
FIG. 32A is a schematic illustration of a SMS module that may be integrated into any of the garments described herein.
Figure 32B:
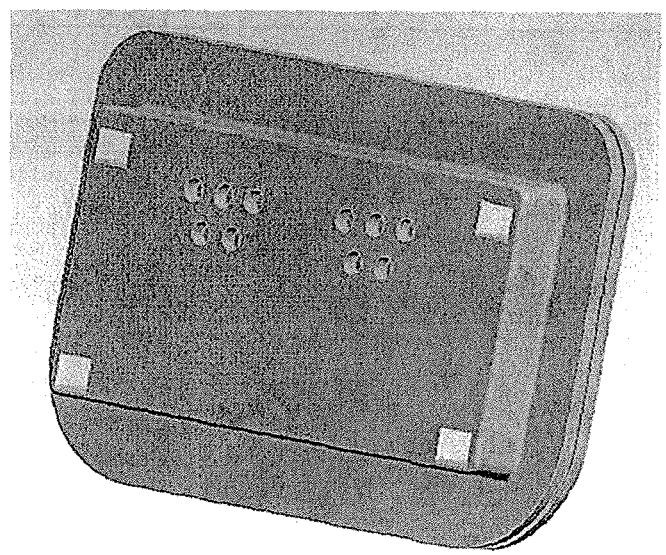
FIG. 32B is an example of a housing for an SMS module such as the one shown in FIG. 32A.

Any of the apparatuses (e.g., garments) described herein may include a sensor manager (SM or SMS), shown schematically in FIG. 32A, that connects the sensors (including electrodes, etc.) on the garment to a processor, including in some variations a smartphone or other mobile device. The sensor manager may be a printed circuit board (PCB) that is part of the sensorized compression garment (e.g., shirt) and may be embedded into a rigid case (as shown in FIG. 32B) placed on the shirt back, e.g., just under the neck as illustrated in FIGS. 1B, 8B, 19C, 20B, 21D and 22C. It is mainly responsible for collecting and elaborating the data coming from the sensors placed all around the shirt.

As shown in FIG. 32A, the PCB forming the sensor module 3201 may include different elements arranged on the PCB, such as a microcontroller 3203 (e.g., CY8C5 microcontroller (68 pin)) and all the connections with a phone module 3205 (metallized drill), tights 3211 (exposed solderable metal area) and sensors 3207, 3209 (connection with threads).

For example, electrical signals coming from the sensors may be carried by conductive threads sewed onto the shirt fabric or onto a tape (e.g., patch) made of the same material. All of these threads may arrive to the SM PCB and can be connected to it using connectors, or sewed/soldered around metallized drills. In contrast to the SMS illustrated here, an SM architecture in which sensors are connected directly to the Phone module would involve a relatively high number of pins 3205 (e.g., one for each trace/thread coming from the sensors). This may limit the number and type of sensors and could compromise the system stability. The architecture described herein allows connection of traces (e.g., threads) coming from the sensors directly to a microcontroller, using different types of connections (e.g., 3207, 3209) that can be placed on the SM PCB. This way, all the sensors signals may be collected (aggregated) by the microcontroller, which will then communicate the processed data to the mobile processor (e.g., a smartphone) module by using only two pins 3205, for holding a digital UART communication. This solution does not limit the type of number of sensors.

As shown in FIG. 32A above, this schematic shows the female connector for the mobile processor (e.g., smartphone) that may be used. In this example, the Sensor Management System (SMS) may be located in the garment rather than on the module/phone. Thus, the number of pins remains constant even if the number of sensors varies between garments or accessories. For example the numbers of pins may remain constant (e.g., at 10-15) by adapting the specific SMS to generically work with different mobile processors (phones).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wearable electronics device, the device comprising:
   a garment comprising a fabric; and
   at least one conductive ink pattern on the garment, wherein the conductive ink pattern comprises:
   a layer of conductive ink having: between about 40-60% conductive particles, between about 30-50% binder; between about 3-7% solvent; and between about 3-7% thickener;
   a layer of an elastic adhesive on the garment; and
   a gradient region between the conductive ink and the adhesive having a thickness of greater than about 10 μm, the gradient region comprising a nonhomogeneous mixture of the conductive ink and the adhesive wherein the concentration of conductive ink decreases from a region closer to the layer of conductive ink to the layer of elastic adhesive.

2. The device of claim 1, wherein the thickness of the layer of elastic adhesive is greater than the thickness of the gradient region and the thickness of the layer of conductive ink is less than the thickness of the elastic layer.

3. The device of claim 1, wherein the garment is a compression garment.

4. The device of claim 1, wherein the conductive particles comprise particles of carbon black.

5. The device of claim 1, wherein the conductive particles comprise particles of one or more of: carbon black, mica, graphene, graphite, silver metal powder, copper metal powder, or iron metal powder.

6. The device of claim 1, wherein the binder comprises acrylic binder.

7. The device of claim 1, wherein the solvent comprises propylenyc glycol.

8. The device of claim 1, wherein the thickener comprises polyurethanic thickener.

9. The device of claim 1, wherein the elastic adhesive comprises a thermo-adhesive water-based glue that is electrically insulative.

10. The device of claim 1, further comprising an insulating resin at least partially over the layer of conductive ink.

11. The device of claim 1, wherein the conductive ink pattern comprises a plurality of layers of the conductive ink.

12. The device of claim 1, wherein a resistivity of the conductive trace is less than about 10 Kohms/square.

13. The device of claim 1, wherein a resistivity of the conductive pattern varies with applied stretch.

14. The device of claim 1, wherein the conductive ink pattern is configured to stretch up to 500% of a resting length without breaking.

15. The device of claim 1, wherein conductive ink pattern is formed as a sensor.

16. The device of claim 1, wherein the conductive ink pattern is formed as a trace.

17. The device of claim 1, wherein the conductive ink pattern is configured as an electrode.

18. The device of claim 1, further comprising a conductive wire coupled to the garment and connected at one end to the conductive ink pattern.

19. A wearable electronics device, the device comprising:
a garment comprising a compression fabric; and
at least one stretchable and conductive ink pattern on the garment having a sheet resistivity of less than about 10 Kohms/square, wherein the conductive ink pattern is stretchable up to at least about 100% without breaking, and comprises:
   a layer of conductive ink having: between about 40-60% conductive particles, between about 30-50% binder; between about 3-7% solvent; and between about 3-7% thickener;
   a layer of an elastic adhesive on the garment;
   a gradient region greater than about 10 µm between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive; and
   an insulating resin over at least a portion of the layer of conductive ink.

20. The device of claim 19, wherein the conductive particles comprise particles of one or more of: carbon black, graphene, graphite, silver metal powder, copper metal powder, or iron metal powder.

21. The device of claim 19, wherein the binder comprises acrylic binder.

22. The device of claim 19, wherein the solvent comprises propylenyc glycol.

23. The device of claim 19, wherein the thickener comprises polyurethanic thickener.

24. The device of claim 19, wherein the elastic adhesive comprises a thermo-adhesive water-based glue that is electrically insulative.

25. The device of claim 19, wherein the conductive ink pattern is configured as an electrode.

26. The device of claim 19, further comprising a conductive wire coupled to the garment and connected at one end to the conductive ink pattern.

27. A wearable electronics device, the device comprising:
a garment comprising a fabric;
at least one conductive ink pattern on the garment, wherein the conductive ink pattern comprises:
   a layer of conductive ink having: between about 40-60% conductive particles, between about 30-50% binder; between about 3-7% solvent; and between about 3-7% thickener;
   a layer of an elastic adhesive on the garment; and
   a gradient region between the conductive ink and the adhesive, the gradient region comprising a nonhomogeneous mixture of the conductive ink and the adhesive wherein the concentration of conductive ink decreases from a region closer to the layer of conductive ink to the layer of elastic adhesive; and
a conductive wire coupled to the fabric and electrically connected at one end region to the conductive ink, wherein the conductive wire extends along garment in a sinusoidal or zig-zag pattern.

28. The device of claim 27, wherein the conductive thread is stitched onto the compression fabric.

29. The device of claim 27, wherein the conductive thread is glued onto the compression fabric.

* * * * *